United States Patent
Stern et al.

(10) Patent No.: US 11,253,594 B2
(45) Date of Patent: Feb. 22, 2022

(54) DRUG COMBINATIONS FOR PROTECTING AGAINST NEURONAL CELL DEATH

(71) Applicant: UNIVERSITY OF PITTSBURGH-OF THE COMMONWEALTH SYSTEM OF HIGHER EDUCATION, Pittsburgh, PA (US)

(72) Inventors: Andrew Michael Stern, Pittsburgh, PA (US); Mark E. Schurdak, Warrendale, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/629,055

(22) PCT Filed: Jul. 9, 2018

(86) PCT No.: PCT/US2018/041292
§ 371 (c)(1),
(2) Date: Jan. 7, 2020

(87) PCT Pub. No.: WO2019/010491
PCT Pub. Date: Jan. 10, 2019

(65) Prior Publication Data
US 2020/0129621 A1    Apr. 30, 2020

Related U.S. Application Data

(60) Provisional application No. 62/530,089, filed on Jul. 7, 2017.

(51) Int. Cl.
*A61K 45/06* (2006.01)
*A61P 25/28* (2006.01)

(52) U.S. Cl.
CPC .............. *A61K 45/06* (2013.01); *A61P 25/28* (2018.01)

(58) Field of Classification Search
CPC .... A61K 45/06; A61K 31/137; A61K 31/352; A61K 31/428; A61K 31/454; A61K 31/46; A61K 31/472; A61K 31/55; A61K 31/553; A61K 33/26; A61P 25/28; G16B 5/00; G16C 20/50; G16C 20/00
See application file for complete search history.

(56) References Cited

U.S. PATENT DOCUMENTS

| 2006/0078533 A1* | 4/2006 | Omoigui ............... A61K 36/899 424/78.14 |
| --- | --- | --- |
| 2007/0117834 A1 | 5/2007 | Hung |
| 2011/0083984 A1* | 4/2011 | Hentemann ............... A61P 3/00 206/438 |
| 2011/0092464 A1 | 4/2011 | Barlow et al. |
| 2011/0230513 A1 | 9/2011 | Lamensdorf et al. |
| 2012/0129834 A1 | 5/2012 | Hughes et al. |
| 2013/0267552 A1 | 10/2013 | Waters et al. |
| 2014/0088140 A1 | 3/2014 | Hayden et al. |
| 2014/0377285 A1* | 12/2014 | Liu ........................ A61K 45/06 424/174.1 |

FOREIGN PATENT DOCUMENTS

| WO | 2008021210 | 2/2008 | |
| --- | --- | --- | --- |
| WO | WO-2014140279 A1 * | 9/2014 | ........... C07D 413/14 |

OTHER PUBLICATIONS

International Search Report and Written Opinion dated Nov. 5, 2018, from International Application No. PCT/US2018/041292, 12 pages.
Willard et al. "Glutamate, Glutamate Receptors, and Downstream Signaling Pathways", Int J Biol Sci. 2013, 9(9):948-959.
Allen, M. D. & Zhang, J. Subcellular dynamics of protein kinase A activity visualized by FRET-based reporters. Biochemical and biophysical research communications 348, 716-721, doi:10.1016/j.bbrc.2006.07.136 (2006).
Barone, J. A. Domperidone: a peripherally acting dopamine2-receptor antagonist. The Annals of pharmacotherapy 33, 429-440 (1999).
Bliss, C. The toxicity of poisons applied jointly. Ann Appl Biol 26, 585-615 (1939).
Chakravarti, A., Clark, A. G. & Mootha, V. K. Distilling Pathophysiology from Complex Disease Genetics. Cell 155, 21-26, doi:10.1016/j.cell.2013.09.001 (2013).
ChEMBL—Benztropine, (2016). Available on-line at:https://www.ebi.ac.uk/chembl/compound_report_card/CHEMBL1201203/.
ChEMBL—Isoetarine, (2016). Available on-line at: https://www.ebi.ac.uk/chembl/compound_report_card/CHEMBL1201213/.
Chen, M. et al. Minocycline inhibits caspase-1 and caspase-3 expression and delays mortality in a transgenic mouse model of Huntington disease. Nature medicine 6, 797-801, doi: 10.1038/77528 (2000).
Chou, T. C. & Talalay, P. Generalized equations for the analysis of inhibitions of Michaelis-Menten and higher-order kinetic systems with two or more mutually exclusive and nonexclusive inhibitors. European journal of biochemistry / FEBS 115, 207-216 (1981).
Chou, T. C. & Talalay, P. Quantitative analysis of dose-effect relationships: the combined effects of multiple drugs or enzyme inhibitors. Advances in enzyme regulation 22, 27-55 (1984).
Clabough, E. B. Huntington's disease: the past, present, and future search for disease modifiers. Yale J Biol Med 86, 217-233 (2013).
Cobanoglu, M. C., Liu, C., Hu, F., Oltvai, Z. N. & Bahar, I. Predicting drug-target interactions using probabilistic matrix factorization. Journal of chemical information and modeling 53, 3399-3409, doi:10.1021/ci400219z (2013).

(Continued)

*Primary Examiner* — Quanglong N Truong
(74) *Attorney, Agent, or Firm* — Meunier Carlin & Curfman LLC

(57) ABSTRACT

Disclosed are compositions and methods for screening drugs that treat neurodegenerative disorders and methods of treating neurodegenerative orders with combinations of said drugs.

15 Claims, 13 Drawing Sheets

(56) References Cited

OTHER PUBLICATIONS

Figure 2A:
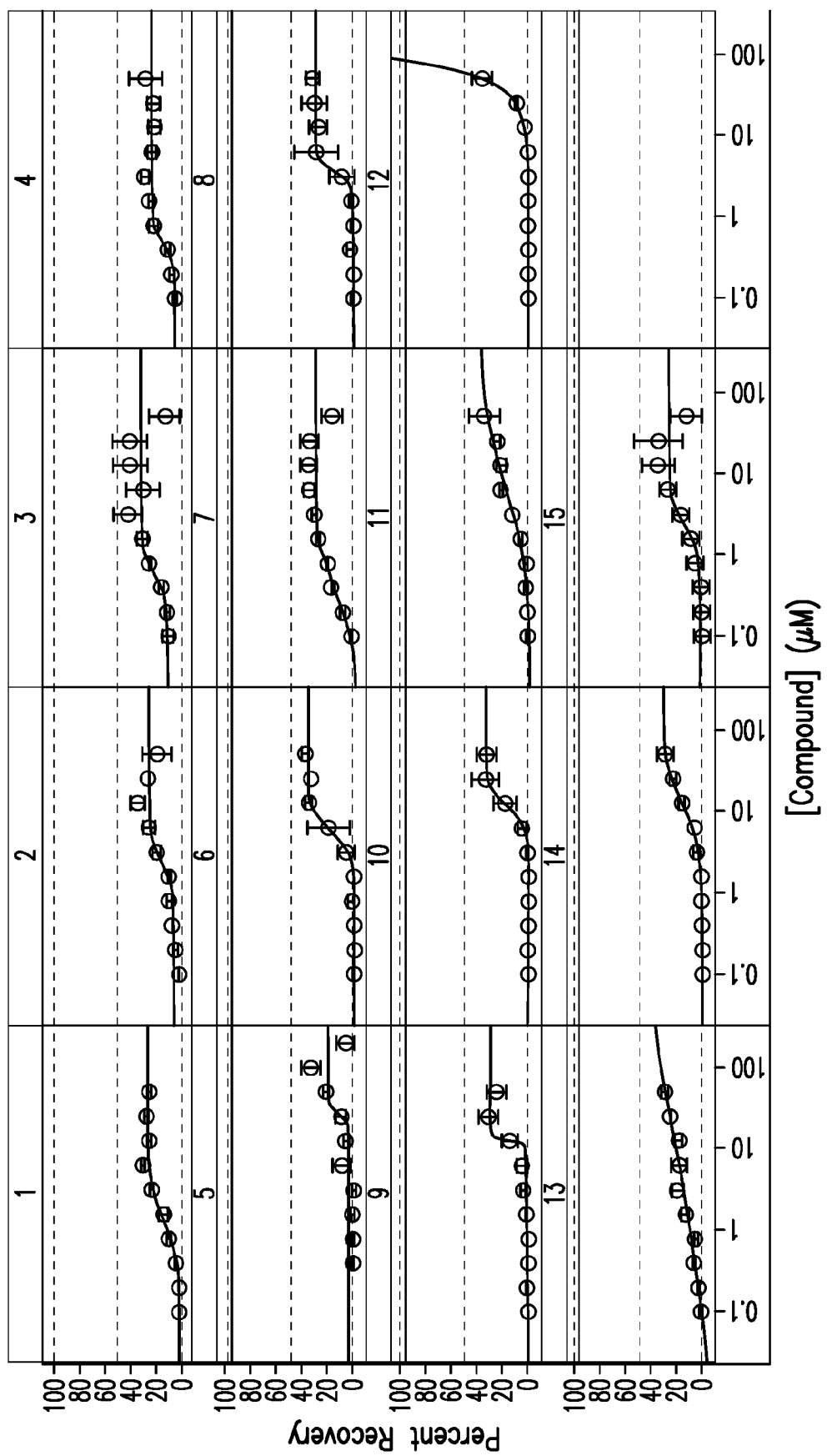

Cobanoglu, M. C., Oltvai, Z. N., Taylor, D. L. & Bahar, I. BalestraWeb: efficient online evaluation of drug-target interactions. Bioinformatics 31, 131-133, doi:DOI 10.1093/bioinformatics/btu599 (2015).
DiPilato, L. M., Cheng, X. & Zhang, J. Fluorescent indicators of cAMP and Epac activation reveal differential dynamics of cAMP signaling within discrete subcellular compartments. Proceedings of the National Academy of Sciences of the United States of America 101, 16513-16518, doi:10.1073/pnas.04Q5973101 (2004).
Gough, A. et al. Biologically Relevant Heterogeneity: Metrics and Practical Insights. J. Biomol Screen In Press (2016).
Gough, A. H. et al. Identifying and quantifying heterogeneity in high content analysis: application of heterogeneity indices to drug discovery. PLoS One 9, e102678, doi:10.1371/journal.pone.0102678 (2014).
Gough, A., Shun, T. Y., Taylor, D. L. & Schurdak, M. A. metric and workflow for quality control in the analysis of heterogeneity in phenotypic profiles and screens. Methods 96, 12-26, doi:10.1016/j.ymeth.2015.10.007 (2016).
Greco, W. R., Bravo, G. & Parsons, J. C. The search for synergy: a critical review from a response surface perspective. Pharmacological reviews 47, 331-385 (1995).
Hawkins, P. C., Skillman, A. G. & Nicholls, A. Comparison of shape-matching and docking as virtual screening tools. Journal of medicinal chemistry 50, 74-82 (2007).
Huang, R. et al. The NCGC pharmaceutical collection: a comprehensive resource of clinically approved drugs enabling repurposing and chemical genomics. Sci Transl Med 3, 80ps16, doi:10.1126/scitranslmed.3001862 (2011).
Inglese, J. et al. Quantitative high-throughput screening: a titration-based approach that efficiently identifies biological activities in large chemical libraries. Proceedings of the National Academy of Sciences of the United States of America 103, 11473-11478, doi:10.1073/pnas.0604348103 (2006).
Kell, D. B., Dobson, P. D., Bilsland, E. & Oliver, S. G. The promiscuous binding of pharmaceutical drugs and their transporter-mediated uptake into cells: what we (need to) know and how we can do so. Drug discovery today 18, 218-239, doi:10.1016/j.drudis.2012.11.008 (2013).
Kroemer, G. et al. Classification of cell death: recommendations of the Nomenclature Committee on Cell Death 2009. Cell death and differentiation 16, 3-11, doi:10.1038/cdd.2008.150 (2009).
Lin, J. T. et al. Regulation of feedback between protein kinase A and the proteasome system worsens Huntington's disease. Molecular and cellular biology 33, 1073-1084, doi:10.1128/MCB.01434-12 (2013).
Lu, B. et al. Identification of NUB 1 as a suppressor of mutant Huntington toxicity via enhanced protein clearance. Nature neuroscience 16, 562-570, doi:10.1038/nn.3367 (2013).
Martz, C. A. et al. Systematic identification of signaling pathways with potential to confer anticancer drug resistance. Sci Signal 7, ra121, doi:10.1126/scisignal.aaa1877 (2014).
Morris, D. I., Robbins, J. D., Ruoho, A. E., Sutkowski, E. M. & Seamon, K. B. Forskolin photoaffinity labels with specificity for adenylyl cyclase and the glucose transporter. The Journal of biological chemistry 266, 13377-13384 (1991).
Myeku, N. et al. Tau-driven 26S proteasome impairment and cognitive dysfunction can be prevented early in disease by activating cAMP-PKA signaling. Nat Med 22, 46-53, doi:10.1038/nm.4011 (2016).
Ona, V. O. et al. Inhibition of caspase-1 slows disease progression in a mouse model of Huntington's disease. Nature 399, 263-267 (1999).
Pamies, D. et al. A human brain microphysiological system derived from induced pluripotent stem cells to study neurological diseases and toxicity. Altex, doi: 10.14573/altex.1609122 (2016).
Poch, G. & Kukovetz, W. R. Papaverine-induced inhibition of phosphodiesterase activity in various mammalian tissues. Life sciences. Pt. 1: Physiology and pharmacology 10, 133-144 (1971).
Rosen, D. S. et al. Pesticidal Cyanine Dye Derivatives. (2003).
Sample, V. et al. Regulation of nuclear PKA revealed by spatiotemporal manipulation of cyclic AMP. Nat Chem Biol 8, 375-382, doi:10.1038/nchembio.799 (2012).
Stern, A. M., Schurdak, M. E., Bahar, I., Berg, J. M. & Taylor, D. L. A Perspective on Implementing a Quantitative Systems Pharmacology Platform for Drug Discovery and the Advancement of Personalized Medicine. J Biomol Screen 21, 521-534, doi:10.1177/1087057116635818 (2016).
Supuran, C. T., Scozzafava, A. & Casini, A. Carbonic anhydrase inhibitors. Medicinal research reviews 23, 146-189, doi: 10.1002/med.10025 (2003).
Trettel, F. Dominant phenotypes produced by the HD mutation in STHdhQ111 striatal cells. Human molecular genetics 9, 2799-2809, doi: 10.1093/hmg/9.19.2799 (2000).
Tsvetkov, A. S. et al. Proteostasis of polyglutamine varies among neurons and predicts neurodegeneration. Nature Chemical Biology 9, 586-592, doi: 10.1038/nchembio.1308(2013).
Wagner, B. K. & Schreiber, S. L. The Power of Sophisticated Phenotypic Screening and Modem Mechanism-of-Action Methods. Cell chemical biology 23, 3-9, doi:10.1016/j.chembiol.2015.11.008 (2016).
Wang, X. et al. Inhibitors of Cytochrome c Release with Therapeutic Potential for Huntington's Disease. Journal of Neuroscience 28, 9473-9485, doi: 10.1523/jneurosci.1867-08.2008 (2008).
Wang, X. et al. Minocycline inhibits caspase-independent and -dependent mitochondrial cell death pathways in models of Huntington's disease. Proceedings of the National Academy of Sciences 100, 10483-10487, doi:10.1073/pnas.1832501100 (2003).
Yano, H. et al. Inhibition of mitochondrial protein import by mutant huntingtin. Nature neuroscience 17, 822-831, doi:10.1038/nn.3721 (2014).
Zhao, W. et al. A New Bliss Independence Model to Analyze Drug Combination Data. J Biomol Screen 19, 817-821, doi:10.1177/1087057114521867 (2014).
Zuccato, C., Valenza, M. & Cattaneo, E. Molecular mechanisms and potential therapeutical targets in Huntington's disease. Physiological reviews 90, 905-981, doi:10.1152/physrev.00041.2009 (2010).
International Preliminary Report on Patentability issued for Application No. PCT/US2018/041292, dated Jan. 16, 2020.

\* cited by examiner

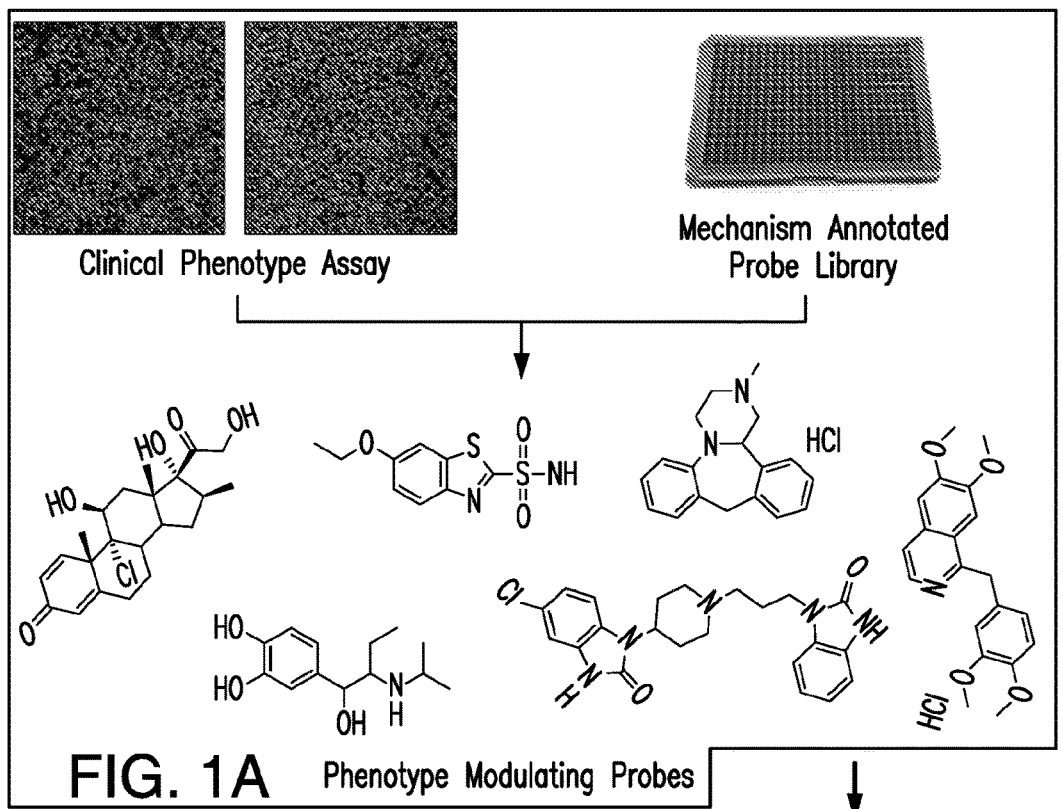
FIG. 1A Phenotype Modulating Probes
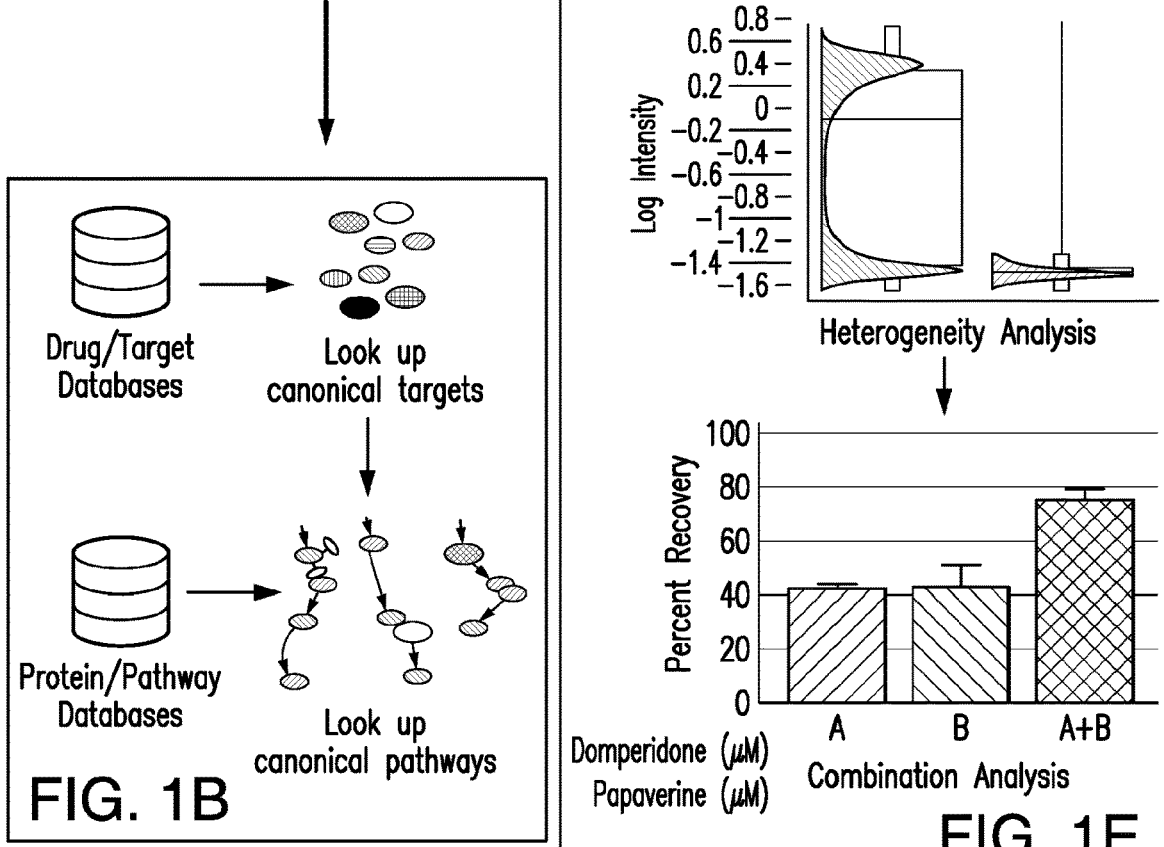
FIG. 1B
FIG. 1E
To FIG.1C
To FIG.1C

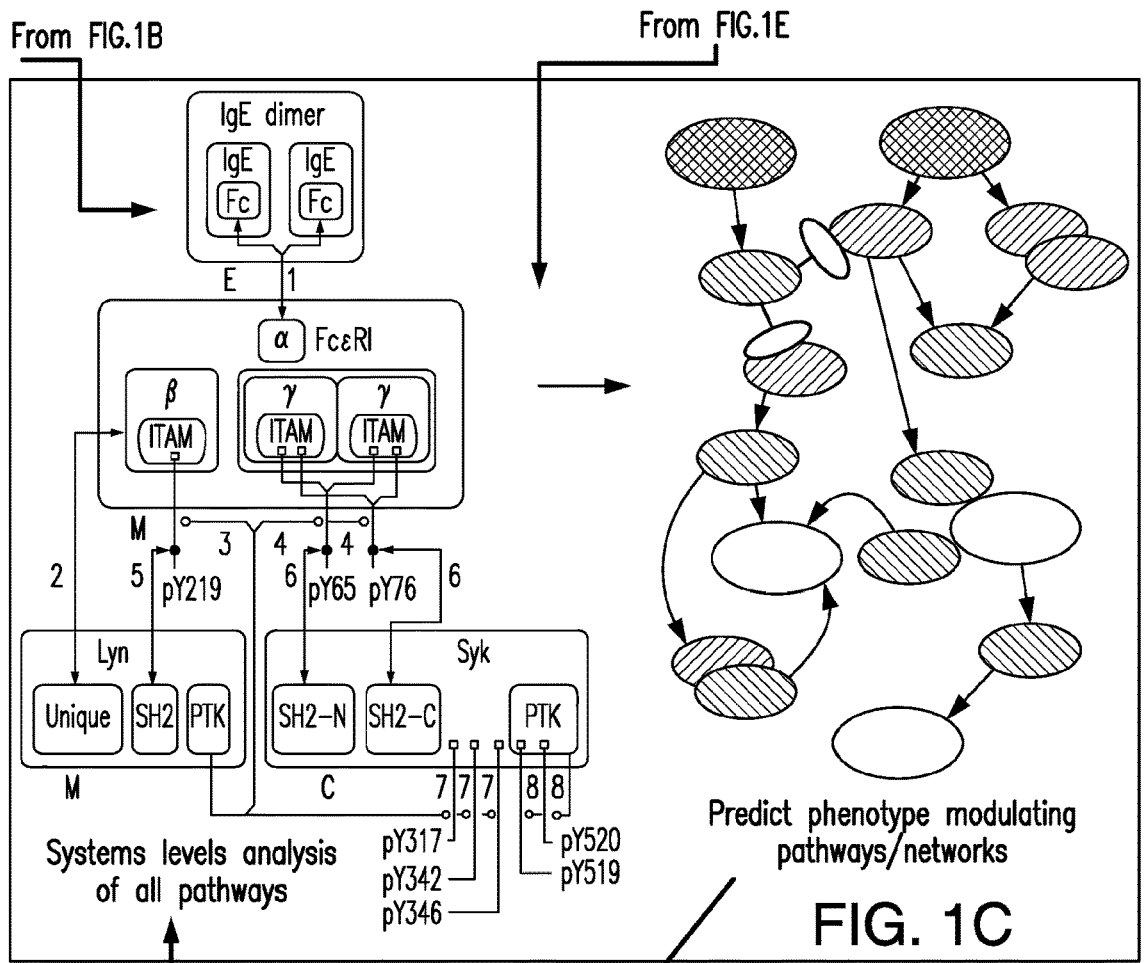
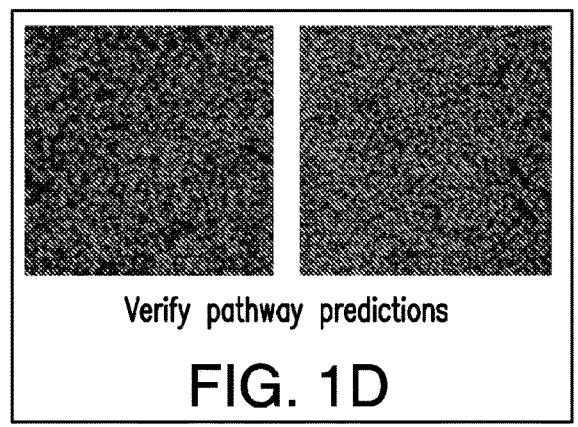
Verify pathway predictions
FIG. 1D
Predict phenotype modulating pathways/networks
FIG. 1C
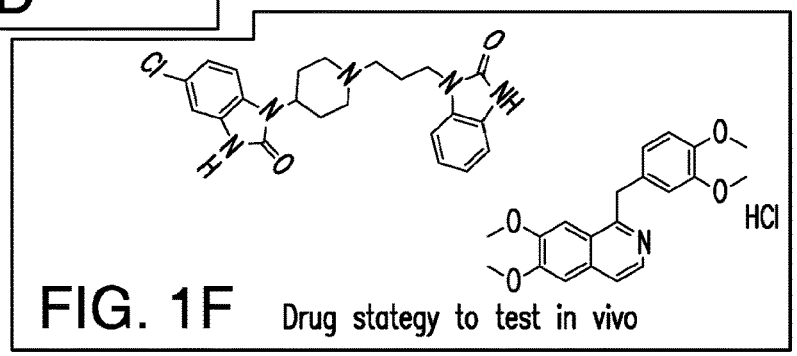
FIG. 1F  Drug stategy to test in vivo

DRUG COMBINATIONS FOR PROTECTING AGAINST NEURONAL CELL DEATH

This application claims the benefit of U.S. Provisional Application No. 62/530,089, filed on Jul. 7, 2017, which is incorporated herein by reference in its entirety.

I. BACKGROUND

Huntington's disease (HD) is a neurodegenerative disease characterized by personality changes, generalized motor dysfunction, and mental deterioration. Symptoms generally develop in the third to fifth decade of life, and the disease ends in dementia and death. HD is rare, affecting 4 to 10 cases in 100,000 people, yet its pathology is strikingly similar to other more common and complex neurodegenerative diseases including Parkinson's and Alzheimer's disease. HD displays an autosomal-dominant inheritance and an abnormal extension of the number of glutamine repeats at the N-terminus of a single protein (huntingtin, HTT). See Zuccato, et al., *Physiological Reviews*, 90:905-981 (2010). Mutant HTT (mHTT) has been shown to satisfy Koch's postulates for causing this devastating neurological disorder in which striatal neuronal subtypes exhibit particular but not exclusive vulnerability. See id.

HTT (and mHTT) is a large protein that interacts with many binding partners (see Clabough, *Yale J. Biol. Med.*, 86:217-233 (2013)), and a number of key pathogenic mechanisms have been described in HD, including aberrant caspase activation, mitochondrial dysfunction (see Ona, et al., *Nature*, 399:263-267 (1999); Chen, et al., *Nature Med.*, 6:797-801, (2000); Wang, et al., *Proc. Nat. Acad. Sci.*, 100:10483-10487 (2003); Wang, et al. *J. Neurosci.*, 28:9473-9485 (2008); and Yano, et al., *Nature Neurosci.*, 17:822-831 (2014)), ER stress, transcriptional dysregulation, altered calcium signaling, proteasome inhibition, defects in vesicle transport, and altered neurotransmitter release and activity (see Zuccato, 90:905 (2010); Ona, 399:263 (1999); and Chen, 6:797, (2000)). However, despite knowledge of the causal gene, and the existence of multiple rodent models that recapitulate key molecular, cellular, and behavioral phenotypes of the human disease (see Zuccato, 90:905 (2010)), drug-like molecules that can reduce mHTT protein expression, increase its clearance, or prevent mutant HTT-induced cell death have yet to be successfully identified in clinical trials. The slow progress toward effective therapy has been attributed to an insufficient knowledge of those biological functions of the mHTT protein that are critical in HD. Furthermore, resulting pleiotropic effects have made it difficult to distinguish whether particular aspects of mHTT-associated dysregulation are actually mechanistically linked to disease progression (i.e., pathogenic), epiphenomena, or disease-ameliorating compensatory effects.

II. SUMMARY

Disclosed are methods and compositions related to identification of neurodegenerative disease treatments and methods of using the same.

In one aspect, disclosed herein are methods of treating a neurodegenerative disorder (such as, for example Huntington's disease) in a subject comprising administering to the subject a first therapeutic agent and a second therapeutic agent; wherein the first therapeutic agent and the second therapeutic agent each bind to one or more targets thereby modulating the activity of at least one target pathway; wherein at least one of the one or more targets bound by the first therapeutic agent is different than the one or more targets bound by the second therapeutic agent; and wherein the combination of therapeutic agents has a synergistic protective effect on the neurodegenerative disorder.

Also disclosed herein are methods of screening for a synergistic combination therapy to a neurodegenerative disease comprising, assaying two or more prospective therapeutic agents for the ability to modulate a disease phenotype using a clinically relevant phenotypic assay; populating from a database targets known to bind the prospective therapeutic agents; selecting at least two prospective therapeutic agents, a first therapeutic agent and a second therapeutic agent; wherein at least one target bound by the first therapeutic agent is different than the targets bound by the second therapeutic agent; and measuring the combinations of prospective therapeutic agents for synergistic protective effect relative to their individual effect using the phenotypic assay.

In one aspect, disclosed herein are methods of any preceding aspect, wherein the neurodegenerative disease is Huntington's Disease, Creutzfeldt-Jakob disease; Primary progressive aphasia; Frontotemporal lobar degeneration; Progressive supranuclear palsy; Friedreich's Ataxia, Alzheimer's Disease, Parkinson's Disease, Sinocerebellar ataxia, prion disease, age related dementia, Amyotrophic lateral sclerosis, or Batten disease.

Also disclosed are methods of any preceding aspect, wherein the clinically relevant assay is a propidium iodide assay comprising contacting serum deprived STHdh$^{111}$ cells with a compound and staining the cells for viability with propidium iodide; wherein an increase in viable cells indicate a protective compound.

Also disclosed are methods of any preceding aspect, wherein the first therapeutic agent and second therapeutic agent are selected from the group consisting of (Z)-Gugglesterone; 3-tropanyl-indole-3-carboxylate hydrochloride; Beclomethasone; Benztropine mesylate; Betamethasone; Budesonide; Cyproheptadine hydrochloride; Domperidone; Ethoxzolamide; Flutamide; Hydrocortisone; Isotharine mesylate; JWH-015; JWH-133; HU-308; L-759,656; CGS 21680; ATL 146e; ATL 313; UK-432,097; TC-E 5005; SA-57; SA-47; JNJ 1661010; URB-597; TAK 21d; JZL 195; PF 750; PF-2545920 hydrochloride; TAK-063; AMG 579; L-741,626; Remoxipride; Raclopride; Nemonapride; LGD-5552; AZD 9567; Mapracorat; LGD-5552; AL-438; Lansoprazole; Lonidamine; Loxapine succinate; Meclizine; Mianserin hydrochloride; m-Iodobenzylguanidine hemisulfate; Papaverine hydrochloride; PD 168,077 maleate; Quipazine, N-methyl-, dimaleate; Ruthenium red; SB 203186; Sodium Nitroprusside; Tetradecylthioacetic acid; Triamcinolone; Triprolidine hydrochloride; U-83836 dihydrochloride; and Vinpocetine.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, 1C, 1D, 1E, and 1F shows the chemogenomics component of the QSP platform. FIG. 1A shows libraries of mechanism annotated probe compounds are screened in a clinically relevant phenotypic assay to identify phenotype modulating probes. FIG. 1B shows targets for the active probes are identified from various drug-target databases and then are associated with biological pathways using information from protein-pathway databases. FIG. 1C shows that using a systems level analysis of all pathways identified, computational analysis is performed to predict the optimal modulating pathways/networks based on the activity of the respective probes (i.e., activation or inhibition of pathways in relation to the known effects of the pathway on the phenotype). FIG. 1D shows that the predicted pathway/network hypotheses are tested in phenotypic assays by i) testing additional compounds known modulated the pathways, ii) testing compounds predicted by advanced machine learning methods that will modulated the pathway, iii) modulate pathways by knock-down and knock-in approaches, and/or iv) evaluate probes in pathway specific phenotypic assays. If pathways are not confirmed, then the hypothesis is refined with the new information gained from the testing, additional probes are identified, and the new hypothesis is tested. If pathways are confirmed, then the active probes are advanced to in vivo testing. FIG. 1E shows that at the initial screening analysis stage, the heterogeneity of phenotype modulating response is assessed. If no heterogeneity is detected, then proceed as above. However, if heterogeneity is detected, then hypotheses are developed and tested to characterize the basis of the heterogeneity (e.g., effects of combinations of different compounds). The information gained from the heterogeneity analysis is used to inform the prediction of the phenotype modulating pathways/networks. FIG. 1F shows the outputs of this strategy are i) a systems level understanding of the pathways/networks involved in the clinically relevant phenotype which enables the design of optimal therapeutic strategies, and ii) probes/drugs that can be advanced to in vivo and clinical testing.

Figure 2B:
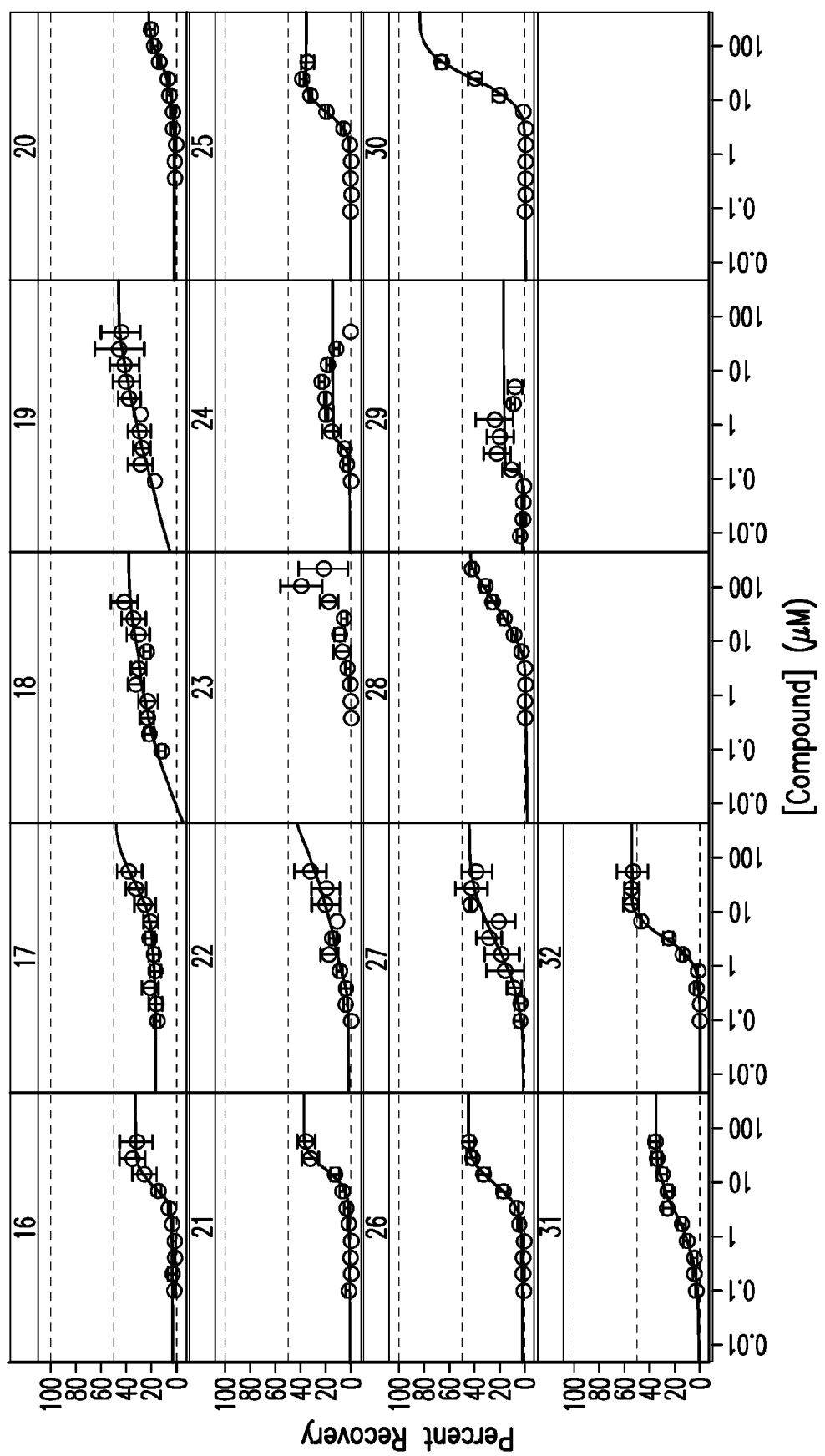

FIGS. 2A and 2B show compounds with confirmed neuroprotective activity in the STHdh$^{Q111}$ model. Compound titrations were tested for neuroprotective activity in the 384-well PI assay. Results are from technical triplicates run on at least 2 different days. Compounds representing a diverse set of canonical mechanisms show only partial efficacy in protecting STHdh$^{Q111}$ cells from mHTT induced cell death. FIG. 2A shows compounds reported in the literature to be associated with central nervous system (CNS) activity: 1) 3-tropanyl-indole-3-carboxylate hydrochloride; 2) Benztropine mesylate; 3) Cyproheptadine hydrochloride; 4) Domperidone; 5) Isotharine mesylate; 6) JWH-015; 7) Loxapine succinate; 8) Meclizine; 9) Mianserin hydrochloride; 10) PD 168,077 maleate; 11) Quipazine, N-methyl-, dimaleate; 12) Ruthenium red; 13) SB 203186; 14) Triprolidine hydrochloride; 15) Vinpocetine. FIG. 2B shows compounds reported to be associated with non-CNS activity: 16) (Z)-Gugglesterone; 17) Beclomethasone; 18) Betamethasone; 19) Budesonide; 20) Ethoxzolamide; 21) Flutamide; 22) Hydrocortisone; 23) Lansoprazole; 24) Lonidamine; 25) m-Iodobenzylguanidine hemisulfate; 26) Papaverine hydrochloride; 27) Prednisolone; 28) Sodium Nitroprusside; 29) Vorinostat; 30) Tetradecylthioacetic acid; 31) Triamcinolone; 32) U-83836 dihydrochloride. Analysis is from triplicate samples run in at least two independent experiments (Error bars are +/−SE).

Figure 3A:
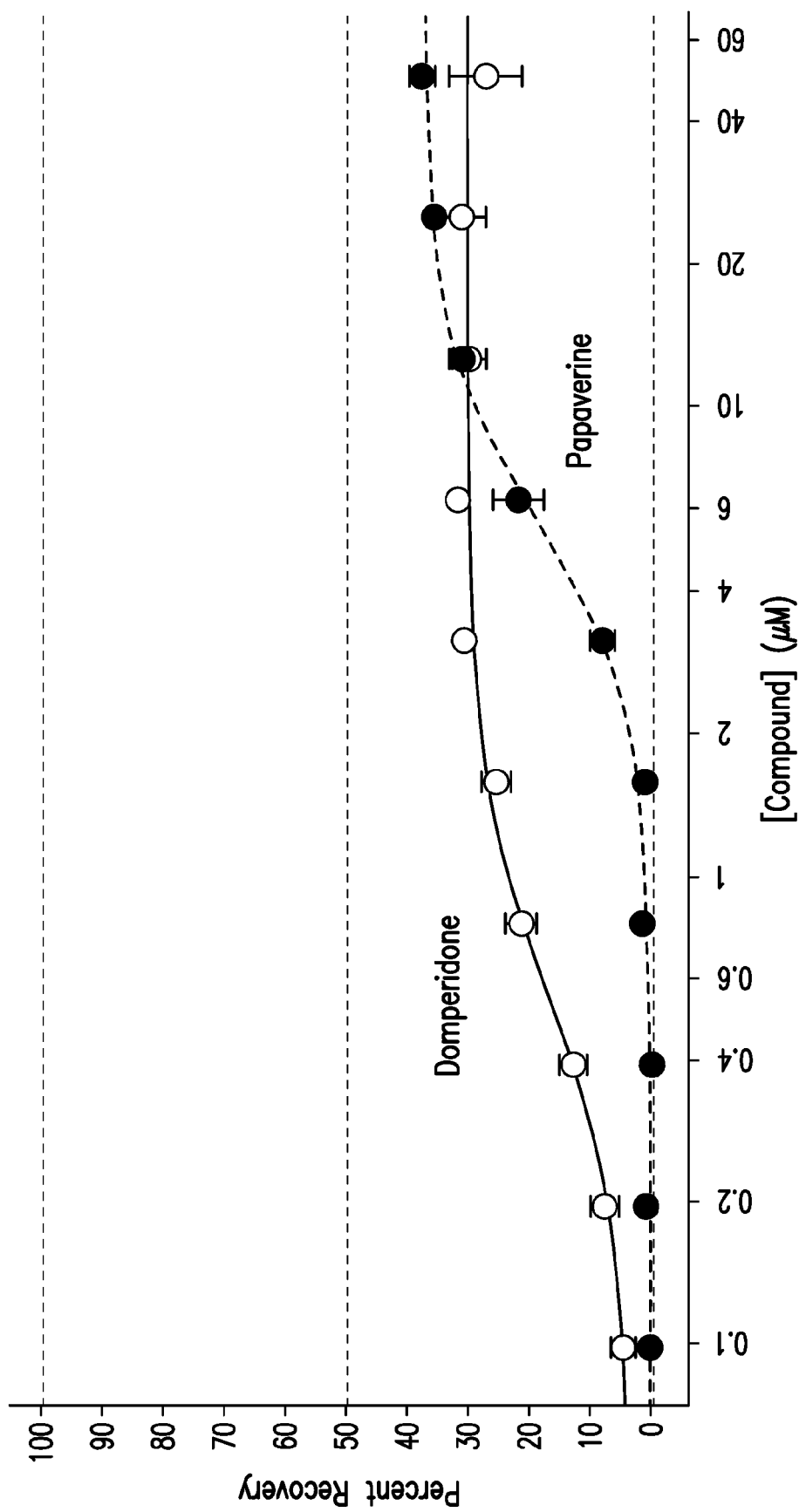
Figure 3B:
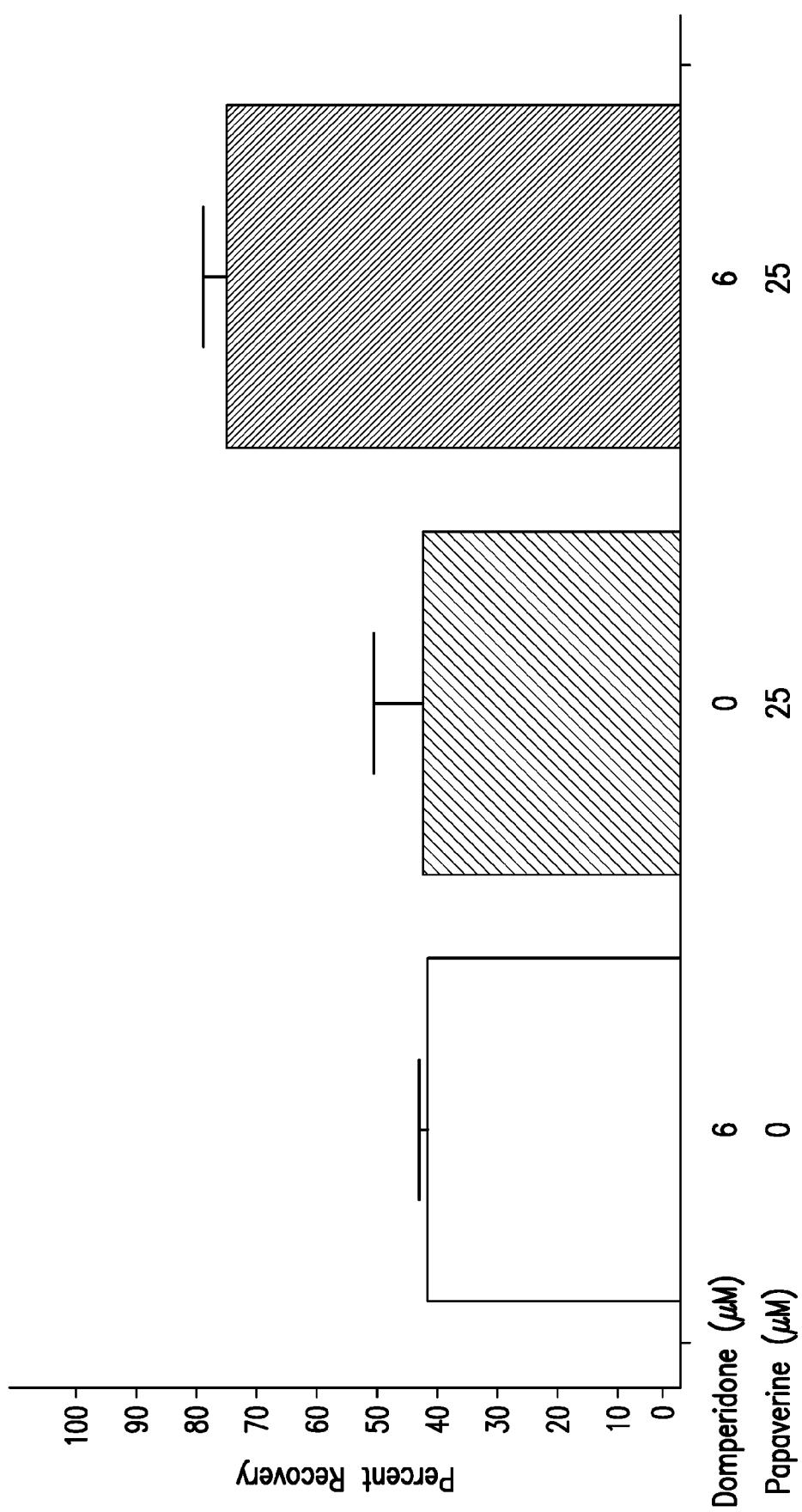

FIGS. 3A and 3B show combinations of probes with different canonical mechanisms provide enhanced protection of STHdh$^{Q111}$ cells. FIG. 3A shows that using domperidone and papaverine as an example, concentrations of compounds that were on the plateau of the activity curve were chosen for combination experiments. In this example, 6 μM domperidone and 25 μM papaverine were selected. FIG. 3B shows that compounds were combined and tested in the 384-well PI assay. The percent activity of the combination was compared with the activity of the single compounds run in parallel, and the ratio of the combined activity to that of the single compound with the highest activity is taken as the combination ratio. For domperidone and papaverine the combination ratio shown here is 1.74 (n=3 independent experiments, error bars are +/−SE). The combination experiments in 3B were run independently from the titration experiments in 3A.

Figure 4A:
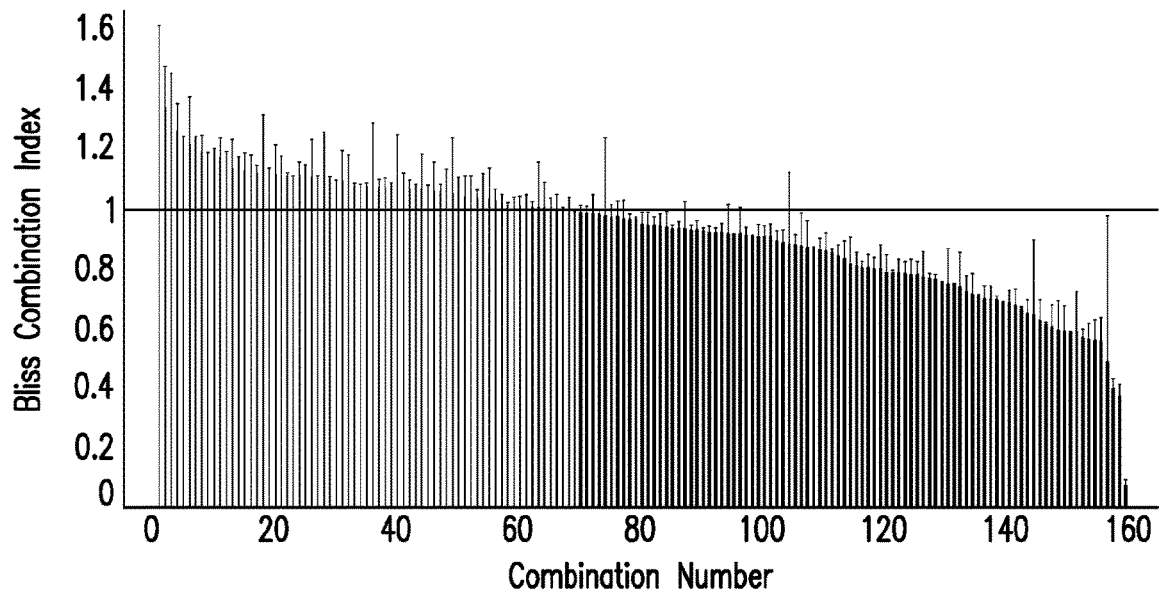
Figure 4B:
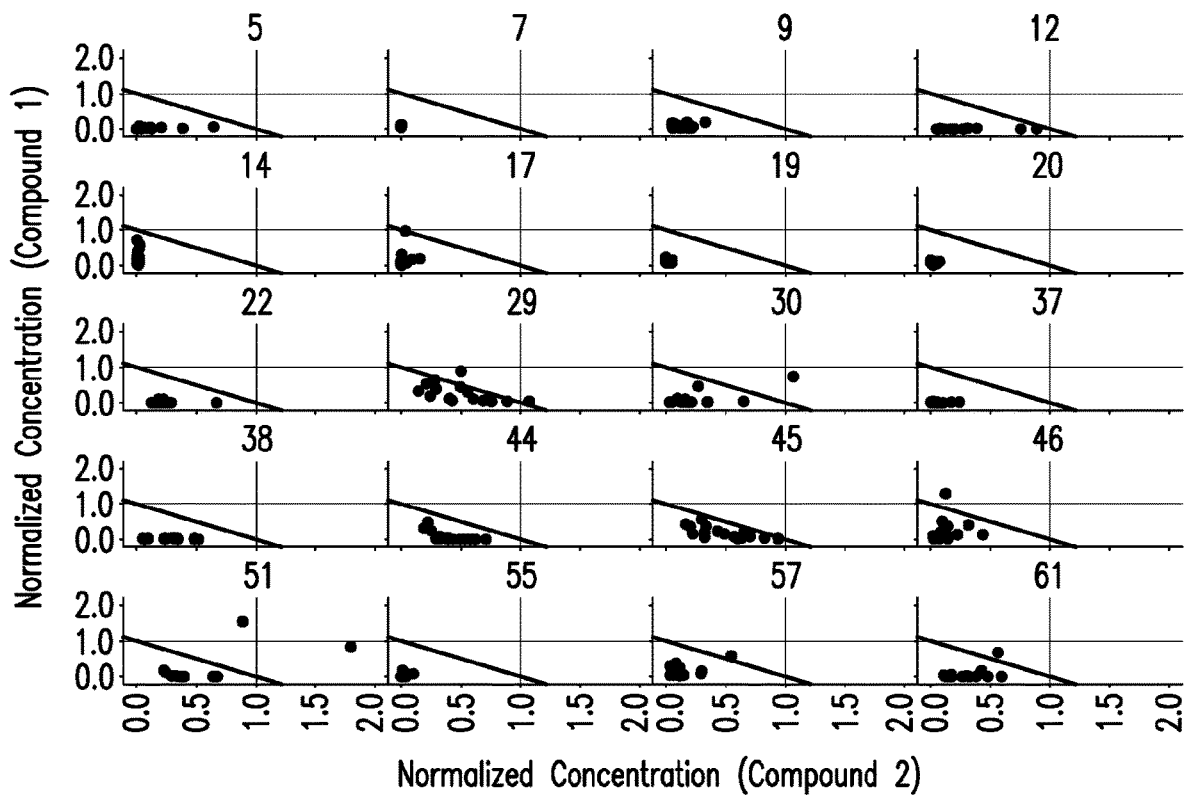

FIGS. 4A and 4B show combinations of probes with synergistic protection in STHdh$^{Q111}$ cells. FIG. 4A shows active LOPAC probes were screened in combinations using a single concentration of each probe. Combination numbers refer to the combinations listed in Table 1. Bliss Independence Model analysis indicated 61 combinations to be synergistic in the single concentration combination screen. The Bliss Independence Model compares the predicted activity of probe combinations determined using the complete additivity of probability theory to the experimentally observed activity of the combination. The Bliss Combination Index (BCI) is the ratio of the observed combination activity to the predicted combination activity based on the activity of the individual compounds. A BCI>1 indicates synergy and a BCI<1 indicates antagonism, while BCI=1 indicates additivity. To accommodate additive BCI calculations not equaling 1 exactly, a cutoff of 0.99-1.01 was assigned to classify synergy and antagonism. (Results from at least 2 independent runs, error bars are the Median Absolute Deviation). FIG. 4B shows 20 probe pairs were selected and tested using 4 different concentrations, 2 each from the plateau and linear portions of the single compound concentrations curves. Curves were analyzed by the method of Chou and Talalay, and the isobolograms are plotted. Points below the diagonal line represent synergistic activity of the two compounds (n=2 independent runs). The panel numbers are the Combination Numbers for the combinations tested listed in Table 3.

Figure 5:
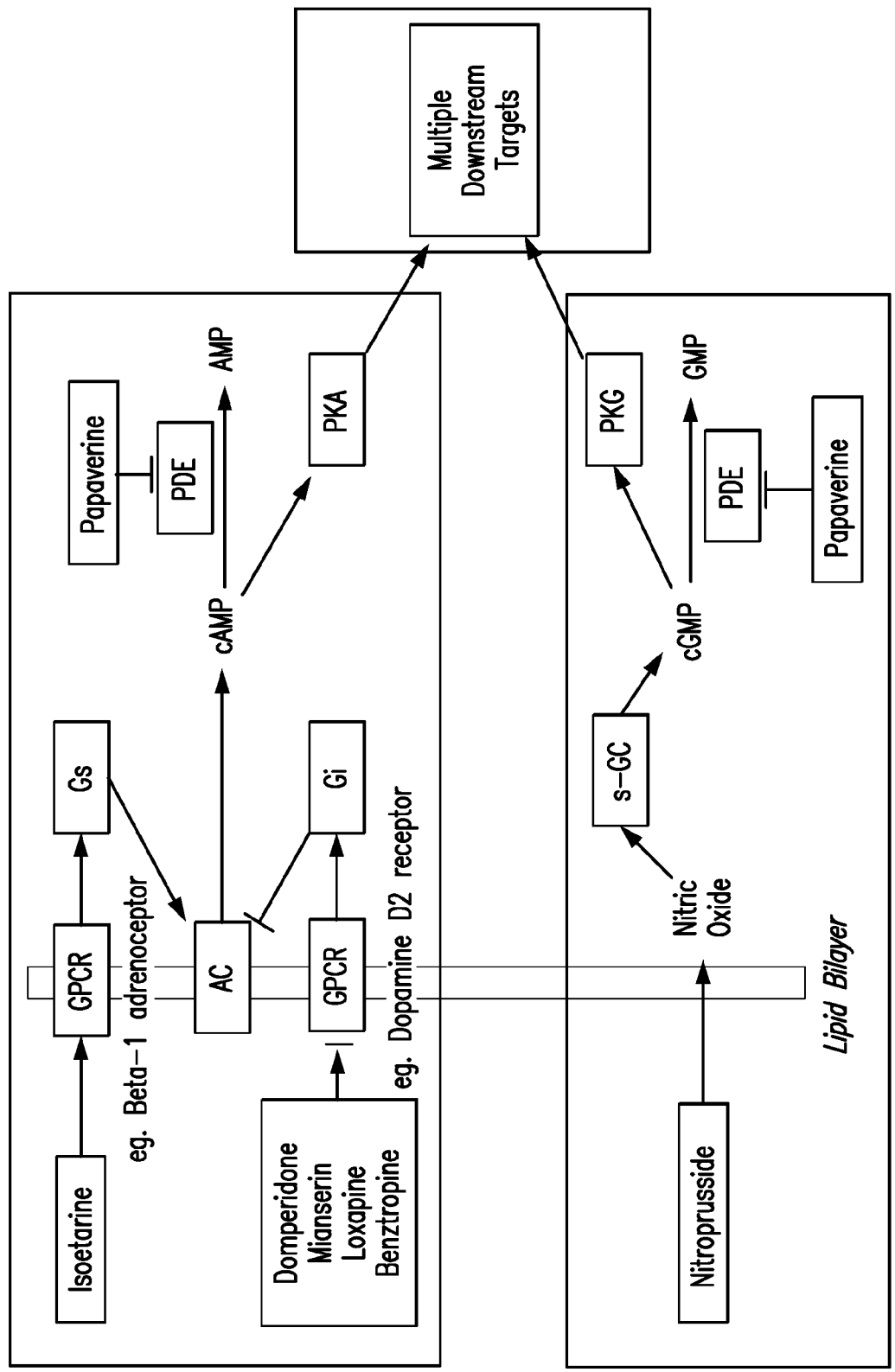

FIG. 5 shows the neuroprotective pathway hypothesized using the canonical targets of compounds that showed synergistic activity.

Figure 6:
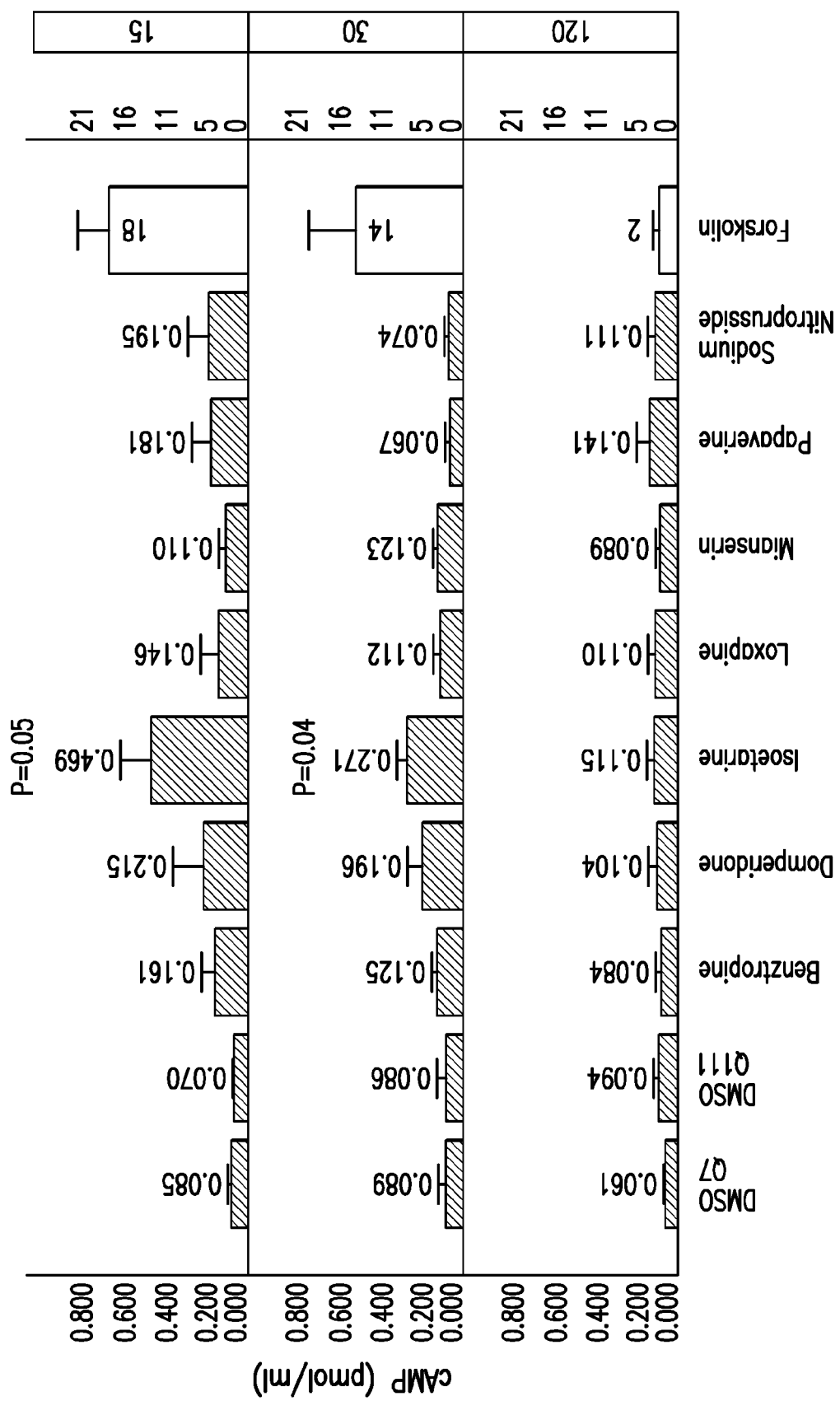

FIG. 6 shows that protective compounds can induce cAMP. cAMP levels were determined in STHdh$^{Q111}$ cells after incubation with benztropine (25 μM), domperidone (6 μM), Isotharine (50 μM), loxapine (6 μM), mianserin (25 μM), papaverine (25 μM), and sodium nitroprusside (66 μM) for 15, 30, and 120 minutes. Numbers on the bars are the average cAMP concentration from three independent experiments. Though isotharine was the only compound to show a statistically significant change at 15 and 30 minutes (Student t-test), except for mianserin, the other compounds showed at least a two-fold increase in cAMP levels at 15 mins. Over time the induced levels of cAMP decreased back to the control levels. Forskolin significantly induced cAMP levels at 15 and 30 minutes with the highest levels seen at 15 minutes. The values are the average from three independent experiments (+/−S.E.) except papaverine where n=2. All compounds except forskolin are plotted on the blue scale on the left, while forskolin is plotted on the grey scale on the right. The three panel rows are 15, 30, and 120 minutes. T-test was used to assess changes in cAMP levels relative to the STHdh$^{Q111}$ cells treated with DMSO.

Figure 7A:
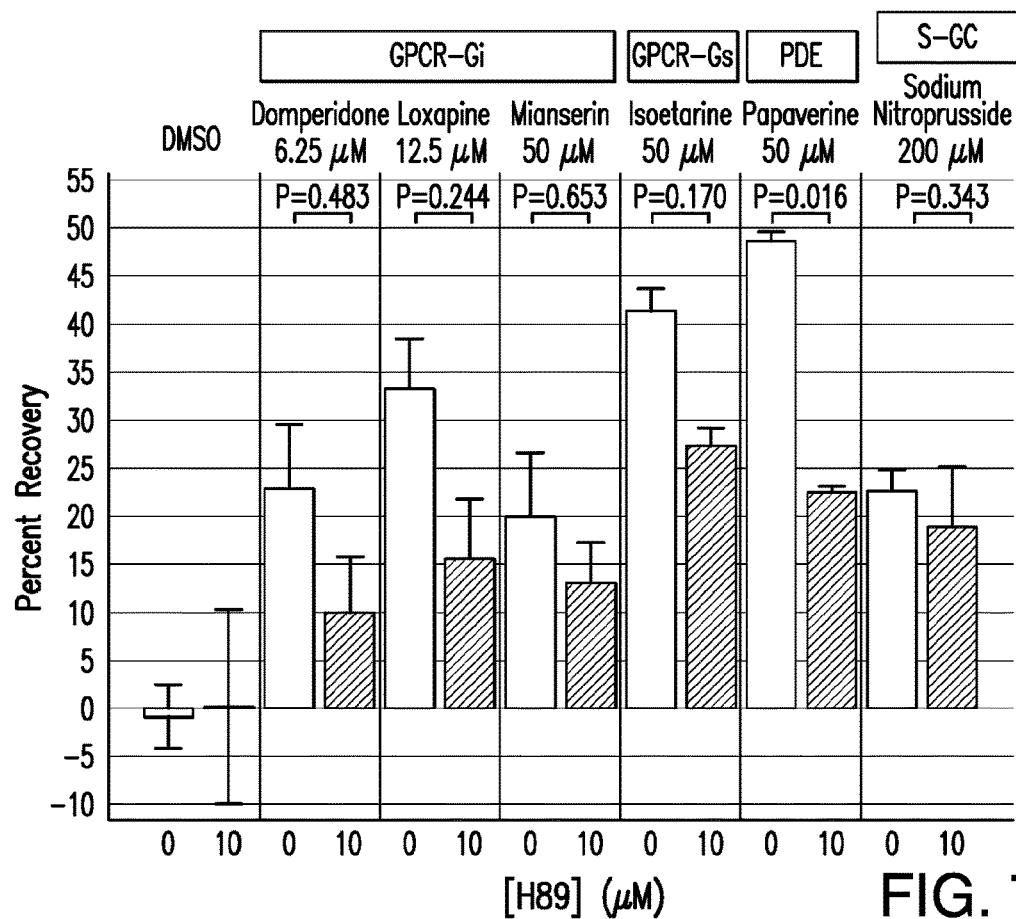
Figure 7B:
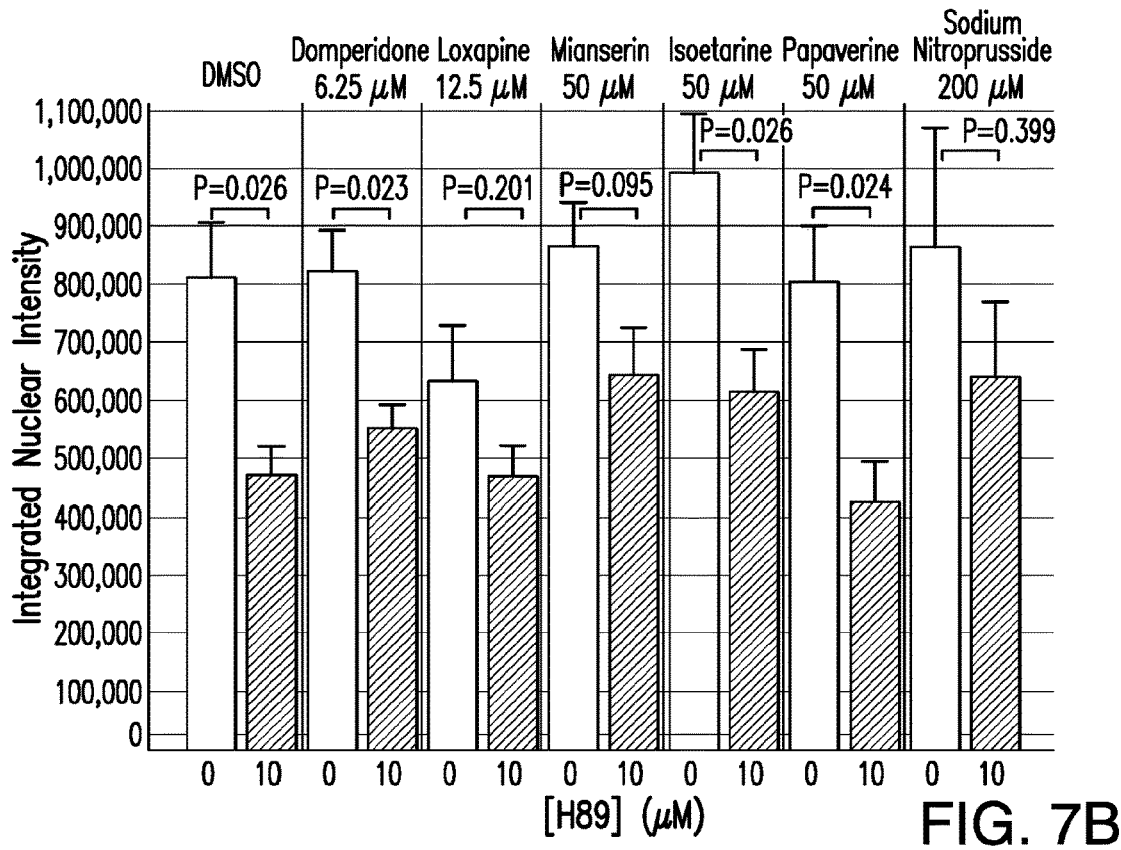

FIGS. 7A and 7B show that the PKA inhibitor H89 inhibits the protective effects of several probes. FIG. 7A shows the protection of STHdh$^{Q111}$ cells from mHTT induced cell death by domperidone (6 μM), isoetarine (50 μM), loxapine (12.5 μM), mianserin (50 μM), papaverine (50 μM), and sodium nitroprusside (200 μM) co-incubated with the PKA inhibitor H89 (10 μM) assessed in the 384- well PI assay. Benztropine (50 µM) was also tested, however, combination with H89 resulted in increased toxicity over the cell death seen in the DMSO control. The concentrations used were chosen to be on plateau of their respective activity curves (see FIG. 3). DMSO is H89 alone which showed no significant protection or toxicity. Analysis is from triplicate samples run in four independent experiments (Error bars are +/−SE). T-test was used to assess changes in the percent recovery levels relative to the STHdh$^{Q111}$ cells treated with compound without H89. While only papaverine showed a statistically significant decrease, the other compounds showed a trend for H89 inhibition of the protective effects. FIG. 7B shows the integrated intensity of the pCREB signal was measured in the nucleus of the STHdh$^{Q111}$ cells treated as above. CREB is a substrate for PKA and was used here as a surrogate marker for PKA activity to demonstrate inhibition of PKA activity by H89. Analysis was from triplicate samples run in four independent experiments (Error bars are +/−SE). T-test was used to assess changes in the pCREB intensity relative to the STHdhQ111 cells treated with compound without H89.

Figure 8:
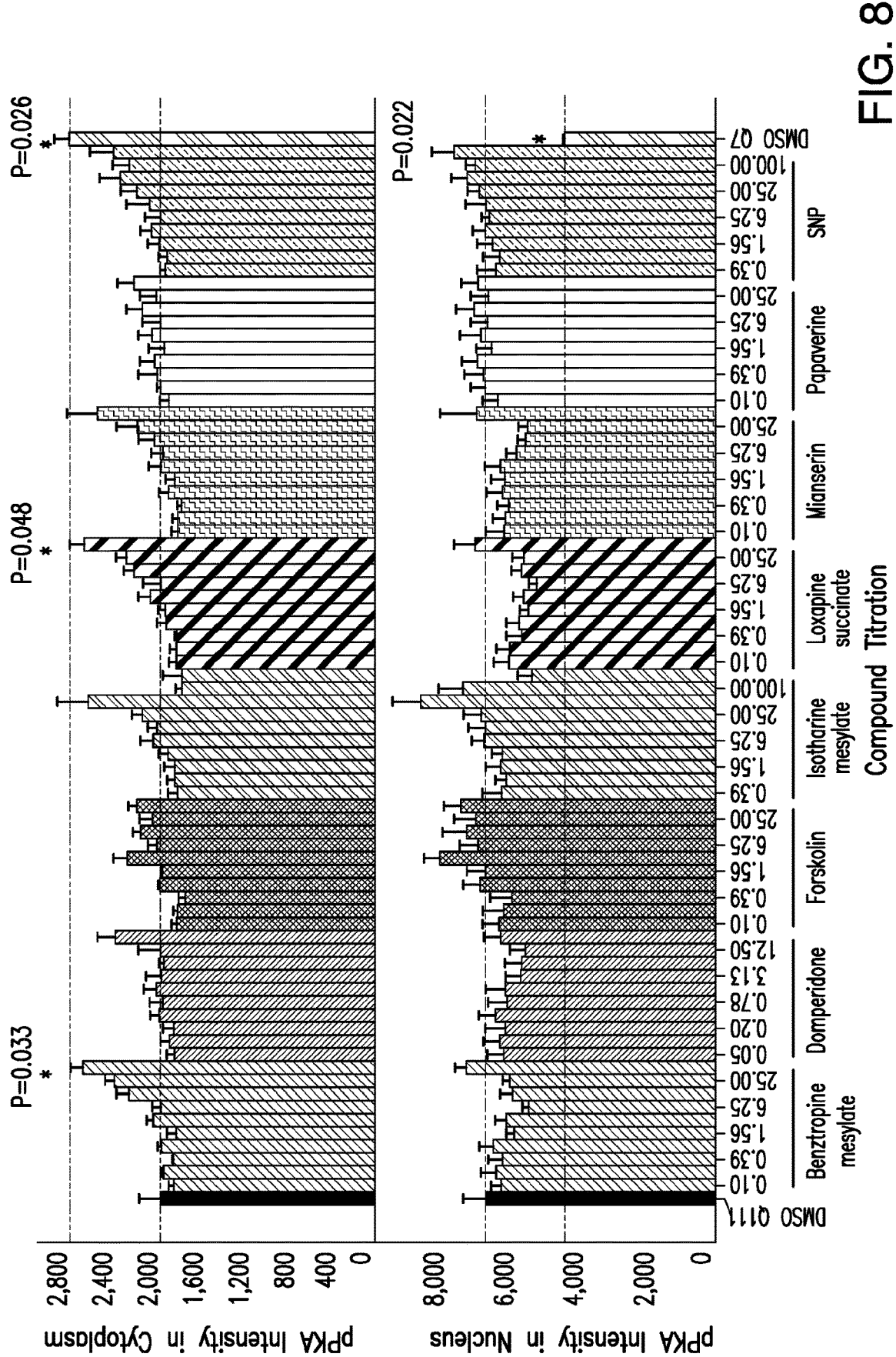

FIG. 8 shows that protective compounds can activate PKA. Cytoplasmic and nuclear pPKA levels were measured in STHdh$^{Q111}$ cells after incubation with benztropine, domperidone, isoetarine, loxapine, mianserin, papaverine, and sodium nitroprusside for 24 h under serum free conditions following the protocol used for the PI protection assay. For cytoplasm levels the upper and lower dotted lines are the average level of STHdh$^{Q7}$ and STHdh$^{Q111}$ cells, respectively. For nuclear levels the upper and lower dotted lines are the average level of STHdh111 and STHdh$^{Q7}$ cells, respectively. Data are the average from three independent experiments (+/−S.E.). T-test was used to assess changes in pPKA levels relative to the STHdh$^{Q111}$ cells treated with DMSO.

Figure 9:
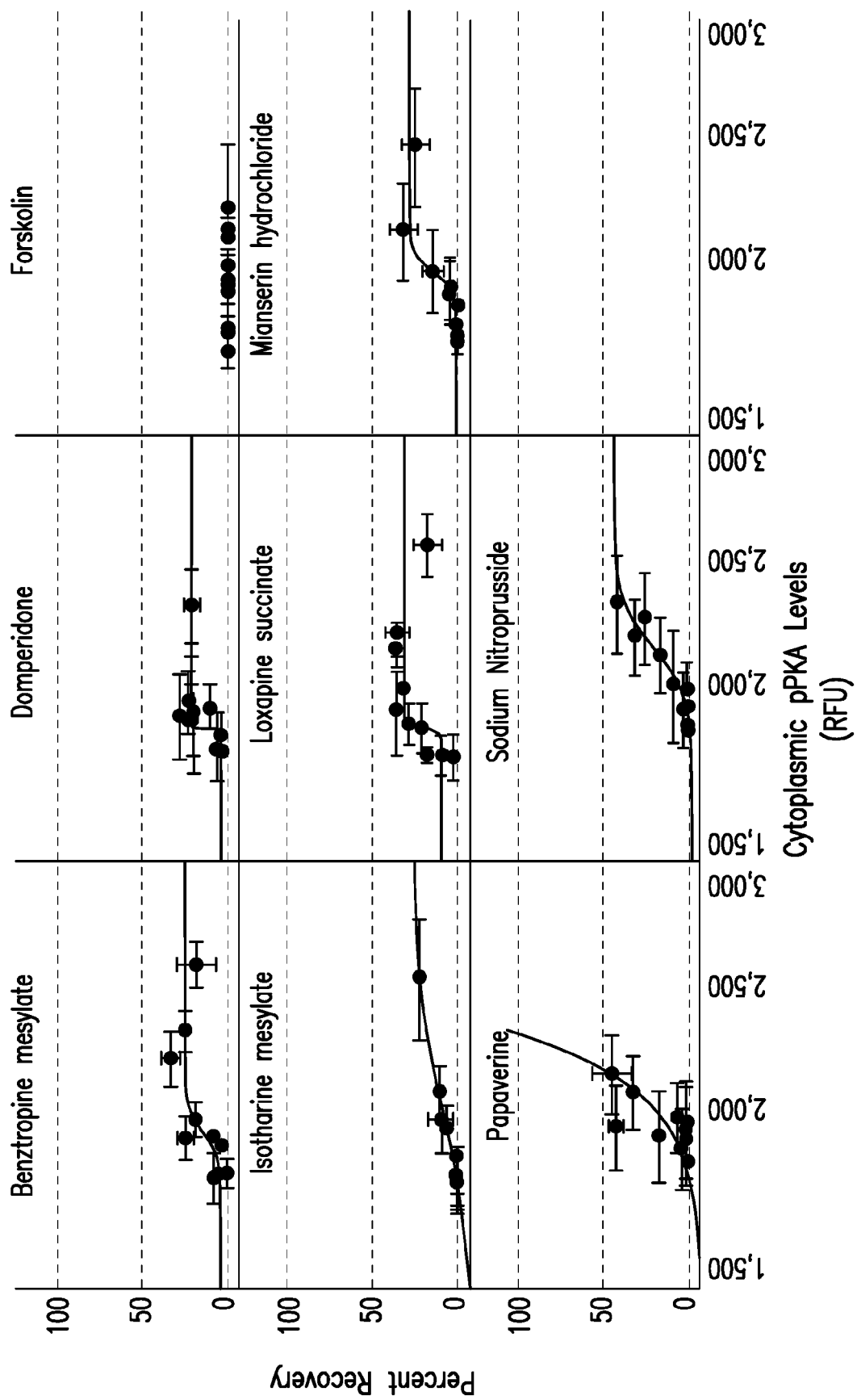

FIG. 9 shows the correlation of Percent Recovery from mHTT toxicity and pPKA levels. The Percent Recovery assessed in the PI assay is plotted against the relative levels of pPKA induced by the compounds measured in the High Content assay. All compounds increased pPKA though some were more effective and showed a robust concentration response (see FIG. 8). Different response curves were observed among the protective compounds. Forskolin was not protective, but did show pPKA levels in the range where protection was seen for the other compounds. The Percent Recovery analysis is from triplicate samples run in least two independent runs, and the pPKA analysis is from triplicate samples run in three independent runs (+/−S.E.).

Figure 10:
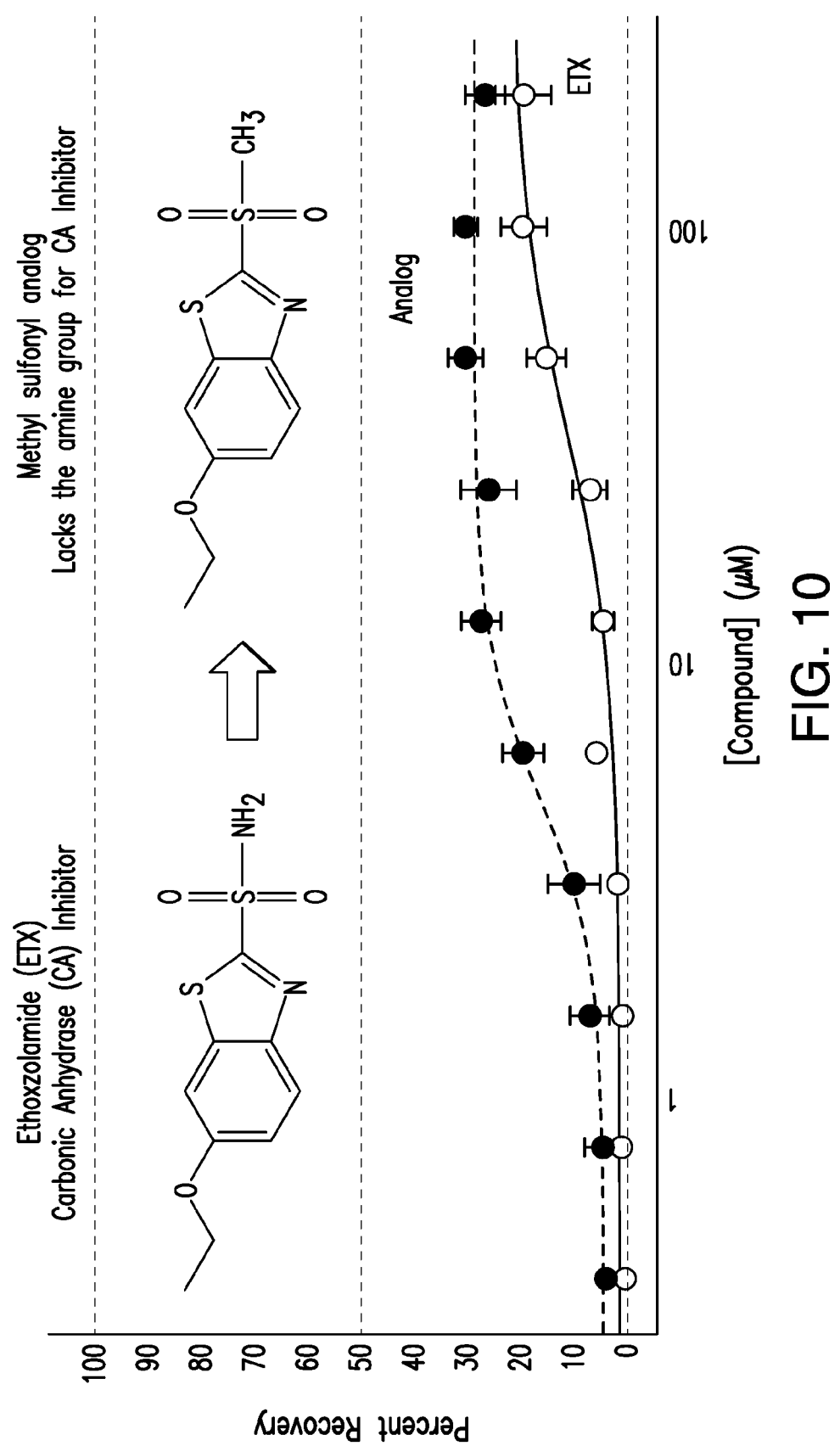

FIG. 10 shows that ethoxzolamide may not work through the canonical carbonic anhydrase mechanism. The methyl sulfonyl analog of ETX does not contain the sulfonamide group of ETX and it is not expected to inhibit carbonic anhydrase. This analog is 7-fold more potent than ETX in protecting STHdh$^{Q111}$ cells from stress induced cell death in the propidium iodide assay indicating that the mechanism of protection of ETX is not through carbonic anhydrase inhibition. Acetazolamide, Brinzolamide and Dorzolamide, all reported carbonic anhydride inhibitors, did not protect STHdh$^{Q111}$ cells further supporting the idea that inhibition of carbonic anhydrase is not a protective mechanism. Interestingly, the methyl sulfonyl analog only protected ~50% of the STHdh$^{Q111}$ cells consistent with the existence of distinct protection mechanisms in different subpopulations of cells.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that these data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, antibodies, small molecules, peptide, polypeptide, peptide mimetic, or nucleic acid (including, but not limited to siRNA and RNAi), salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active antibodies, small molecules, peptide, polypeptide, peptide mimetic, or nucleic acid (including, but not limited to siRNA and RNAi), salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. METHODS OF TREATING A NEURODEGENERATIVE DISORDER AND SCREENING FOR SYNERGISTIC THERAPIES FOR USE IN SAID TREATMENTS

Currently, there is no effective treatment for most neurodegenerative diseases, including, Huntington's Disease (HD). The most cutting-edge experimental treatments undergoing clinical trials use single agent therapies and have failed to identify effective drugs to prevent cell death. Treating HD, or any complex disease, requires a thorough understanding of its mechanisms of progression. Identifying disease mechanisms is hindered by epistasis, pleiotropy and heterogeneity, all of which are intrinsic and often confounding characteristics in complex diseases. An attractive path to systematically understanding mechanisms of disease progression is Quantitative Systems Pharmacology (QSP), an approach that integrates and iterates computational and experimental methods to determine molecular pathogenesis. A chemogenomics component of QSP involves perturbing disease phenotypes in clinically relevant assays with mechanistically annotated compounds, and using the known mode-of-action of active compounds to infer cellular pathways that are related to the disease and its modulation (see FIG. 1). Concordance in the perturbation of a disease phenotype among a set of structurally diverse chemical probes sharing an annotated common mechanism can provide compelling evidence for the role of a particular target/pathway in the molecular etiology. In turn, a discordance with such a probe set can lead to the identification of a novel disease-specific mechanism. This finely tunable pharmacological approach is complementary to genetic approaches.

Accordingly, in one aspect, disclosed herein are methods of screening for synergistic combination therapies to a neurodegenerative disease (such as, for example, Huntington's Disease, Creutzfeldt-Jakob disease; Primary progressive aphasia; Frontotemporal lobar degeneration; Progressive supranuclear palsy; Friedreich's Ataxia, Alzheimer's Disease, Parkinson's Disease, Sinocerebellar ataxia, prion disease, age related dementia, Amyotrophic lateral sclerosis, and/or Batten disease) assaying two or more prospective therapeutic agents for the ability to modulate a disease phenotype using a clinically relevant phenotypic assay; populating from a database targets known to bind the prospective therapeutic agents; selecting at least two prospective therapeutic agents, a first therapeutic agent and a second therapeutic agent; wherein at least one target bound by the first therapeutic agent is different than the targets bound by the second therapeutic agent; and measuring the combinations of prospective therapeutic agents for synergistic protective effect relative to their individual effect using a phenotypic assay. In one aspect, the methods of screening can further comprise pairing prospective therapeutic agents by selecting the optimal modulating pathways/networks based on the activity of the respective therapeutic agents (i.e., activation or inhibition of pathways in relation to the known effects of the pathway on the phenotype).

The predicted pathways/networks are tested in phenotypic assays by i) testing additional compounds known to be modulated by the pathways, ii) testing compounds predicted by advanced machine learning methods that will modulate the pathway, iii) modulating pathways by knock-down and knock-in approaches, and/or iv) evaluating probes in pathway specific phenotypic assays. When pathways are not confirmed, then the phenotypic mechanism is refined with the new information gained from the testing, additional probes are identified, and the new mechanism is tested. When the pathways are confirmed, then the active probes are advanced to in vivo testing. At the initial screening analysis stage, the heterogeneity of phenotype modulating response is assessed. If no heterogeneity is detected, then proceed as above. However, if heterogeneity is detected, then hypotheses are developed and tested to characterize the basis of the heterogeneity (e.g., effects of combinations of different compounds). The information gained from the heterogeneity analysis is used to inform the identification of the phenotype modulating pathways/networks. The outputs of this strategy are i) a systems level understanding of the pathways/networks involved in the clinically relevant phenotype which enables the design of optimal therapeutic strategies, and ii) probes/drugs that can be advanced to in vivo and clinical testing.

As noted above, the disclosed methods can be used to screen for combination therapies to treat any known neurodegenerative disease, including, but not limited to Huntington's Disease, Creutzfeldt-Jakob disease; Primary progressive aphasia; Frontotemporal lobar degeneration; Progressive supranuclear palsy; Friedreich's Ataxia, Alzheimer's Disease, Parkinson's Disease, Sinocerebellar ataxia, prion disease, age related dementia, Amyotrophic lateral sclerosis, and/or Batten disease. In one aspect, disclosed herein are methods of screening for therapeutic agent combination therapies to a Huntington's Disease comprising, screening for a synergistic combination therapy to a neurodegenerative disease comprising, assaying two or more prospective therapeutic agents for the ability to modulate a disease phenotype using a clinically relevant phenotypic assay; populating from a database targets known to bind the prospective therapeutic agents; selecting at least two prospective therapeutic agents, a first therapeutic agent and a second therapeutic agent; wherein at least one target bound by the first therapeutic agent is different than the targets bound by the second therapeutic agent; and measuring the combinations of prospective therapeutic agents for synergistic protective effect relative to their individual effect using a phenotypic assay.

It is understood and herein contemplated that any clinically relevant source for therapeutic agents can be used in the disclosed methods including therapeutic agents probe libraries. For example, where the neurodegenerative disease is Huntington's disease, a LOPAC library can be screened using a clinically relevant assay to identify therapeutic agents (such as, for example, small molecules).

In one aspect, the clinically relevant phenotypic assays for use in the disclosed screen can comprise any phenotypic assay that has been previously established to reflect a clinically relevant phenotypic state. For example, the phenotypic assays can comprise cell viability assays such as propidium iodide assays that measure a clinically relevant end such as point of cell death. For example, in one aspect, it is understood and herein contemplated that the propidium iodide assay can comprise contacting serum deprived STHdh[111] cells (which express mutant HTT (mHTT) and unchecked develop mHTT-dependent cell death) with a compound and staining the cells for viability with propidium iodide; wherein in viable cells indicate a protective compound. Combinations of compounds known to affect different cellular pathways are tested in combination and evaluated for synergistic, additive, or antagonistic responses. Compound combinations (i.e., small molecule combinations) having a synergistic effect are combination therapies for the treatment of neurodegenerative disease (such as, for example, Huntington's disease Creutzfeldt-Jakob disease; Primary progressive aphasia; Frontotemporal lobar degeneration; Progressive supranuclear palsy; Friedreich's Ataxia, Alzheimer's disease, Parkinson's disease, Sinocerebellar ataxia, prion disease, age related dementia, Amyotrophic lateral sclerosis, and/or Batten disease).

As disclosed herein, for Huntington's disease, the QSP approach was initiated and implemented the chemogenomic strategy to investigate the protective effects of small molecule probes with diverse canonical molecular mechanisms of action in a well-established striatal neuronal model (STHdh$^{Q111}$) for HD. A number of small molecule probes were identified with a range of distinct canonical mechanisms that protect the STHdh$^{Q111}$ cells from mHTT-induced death. The response of the cell population to most of the compounds was heterogeneous, i.e., not all of the cells within a population were protected by the compounds.

Interestingly, testing of combinations of moderately active compounds identified specific combinations that synergistically increased the efficacy of protection. Analysis of the canonical mechanisms of 10 compound pairs that synergistically protected STHdh$^{Q111}$ cells showed a convergence of pathways leading to the activation of PKA and PKG. Cytoplasmic phospho-PKA levels were lower in STHdh$^{Q111}$ than in the wild type STHdh$^{Q7}$ cells under stress conditions, and these levels were increased by several of the protective compounds. The results indicate that active PKA has a role in the protective effects of these compounds. The information gained from the annotated compounds and combination analysis provided input for inference of neuronal cell protective pathways.

In other words, using a combination of drugs identified via a novel chemogenomic approach, the present disclosure demonstrates that synergy in neuroprotective drug activity can be a more effective therapy for HD than any single drug therapy in clinical trials. Accordingly, in one aspect, disclosed herein are methods of treating a neurodegenerative disorder (such as, for example, Huntington's Disease, Alzheimer's Disease, Parkinson's Disease, Sinocerebellar ataxia, prion disease, age related dementia, Amyotrophic lateral sclerosis, and/or Batten disease) in a subject comprising administering to the subject a first therapeutic agent and a second therapeutic agent; wherein the first therapeutic agent and the second therapeutic agent each binds to one or more targets thereby modulating the activity of at least one target pathway; wherein at least one of the one or more targets bound by the first therapeutic agent is different than the one or more targets bound by the second therapeutic agent; and wherein the combination of therapeutic agents has a synergistic protective effect on the neurodegenerative disorder.

In one aspect, the combination of two or more therapeutic agents (including the first therapeutic agent and the second therapeutic agent) for treating a neurodegenerative disease can comprise any combination of 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 58 of the compounds identified herein, including, but not limited to (Z)-Gugglesterone; 3-tropanyl-indole-3-carboxylate hydrochloride; Beclomethasone; Benztropine mesylate; Betamethasone; Budesonide; Cyproheptadine hydrochloride; Domperidone; Ethoxzolamide; Flutamide; Hydrocortisone; Isotharine mesylate; JWH-015; JWH-133; HU-308; L-759,656; CGS 21680; ATL 146e; ATL 313; UK-432,097; TC-E 5005; SA-57; SA-47; JNJ 1661010; URB-597; TAK 21d; JZL 195; PF 750; PF-2545920 hydrochloride; TAK-063; AMG 579; L-741,626; Remoxipride; Raclopride; Nemonapride; LGD-5552; AZD 9567; Mapracorat; LGD-5552; AL-438; Lansoprazole; Lonidamine; Loxapine succinate; Meclizine; Mianserin hydrochloride; m-Iodobenzylguanidine hemisulfate; Papaverine hydrochloride; PD 168,077 maleate; Quipazine, N-methyl-, dimaleate; Ruthenium red; SB 203186; Sodium Nitroprusside; Tetradecylthioacetic acid; Triamcinolone; Triprolidine hydrochloride; U-83836 dihydrochloride; Vinpocetine and/or any combination listed in Tables 4, 5, or 6. For example, in one aspect, the two or more therapeutic agents are selected from the group consisting of (Z)-Gugglesterone; 3-tropanyl-indole-3-carboxylate hydrochloride; Beclomethasone; Benztropine mesylate; Betamethasone; Budesonide; Cyproheptadine hydrochloride; Domperidone; Ethoxzolamide; Flutamide; Hydrocortisone; Isotharine mesylate; JWH-015; JWH-133; HU-308; L-759,656; CGS 21680; ATL 146e; ATL 313; UK-432,097; TC-E 5005; SA-57; SA-47; JNJ 1661010; URB-597; TAK 21d; JZL 195; PF 750; PF-2545920 hydrochloride; TAK-063; AMG 579; L-741,626; Remoxipride; Raclopride; Nemonapride; LGD-5552; AZD 9567; Mapracorat; LGD-5552; AL-438; Lansoprazole; Lonidamine; Loxapine succinate; Meclizine; Mianserin hydrochloride; m-Iodobenzylguanidine hemisulfate; Papaverine hydrochloride; PD 168,077 maleate; Quipazine, N-methyl-, dimaleate; Ruthenium red; SB 203186; Sodium Nitroprusside; Tetradecylthioacetic acid; Triamcinolone; Triprolidine hydrochloride; U-83836 dihydrochloride; and Vinpocetine. Thus, in one aspect disclosed herein are methods of treating a neurodegenerative disorder (such as, for example, Huntington's disease) in a subject comprising administering to the subject a first therapeutic agent and a second therapeutic agent wherein the first and second therapeutic agents are selected from the group consisting of (Z)-Gugglesterone; 3-tropanyl-indole-3-carboxylate hydrochloride; Beclomethasone; Benztropine mesylate; Betamethasone; Budesonide; Cyproheptadine hydrochloride; Domperidone; Ethoxzolamide; Flutamide; Hydrocortisone; Isotharine mesylate; JWH-015; JWH-133; HU-308; L-759,656; CGS 21680; ATL 146e; ATL 313; UK-432,097; TC-E 5005; SA-57; SA-47; JNJ 1661010; URB-597; TAK 21d; JZL 195; PF 750; PF-2545920 hydrochloride; TAK-063; AMG 579; L-741,626; Remoxipride; Raclopride; Nemonapride; LGD-5552; AZD 9567; Mapracorat; LGD-5552; AL-438; Lansoprazole; Lonidamine; Loxapine succinate; Meclizine; Mianserin hydrochloride; m-Iodobenzylguanidine hemisulfate; Papaverine hydrochloride; PD 168,077 maleate; Quipazine, N-methyl-, dimaleate; Ruthenium red; SB 203186; Sodium Nitroprusside; Tetradecylthioacetic acid; Triamcinolone; Triprolidine hydrochloride; U-83836 dihydrochloride; and Vinpocetine. For example, in one aspect, disclosed herein are methods of treating a neurodegenerative disorder (such as Huntington's disease) in a subject comprising administering to the subject, a first therapeutic agent and a second therapeutic agent; wherein the combination of first and second therapeutic agents has a synergistic protective effect on the neurodegenerative disorder; and wherein the first and second therapeutic agents comprise any combination of therapeutic agents from Table 3 or Table 6, such as, for example, Betamethasone and Lonidamine; Ruthenium red and Budesonide; Sodium Nitroprusside and Triamcinolone; Ruthenium red and 3-tropanyl-indole-3-carboxylate hydrochloride; Sodium Nitroprusside and Betamethasone; Triprolidine hydrochloride and 3-tropanyl-indole-3-carboxylate hydrochloride; Sodium Nitroprusside and Beclomethasone; Beclomethasone and Budesonide; Ethoxzolamide and Beclomethasone; Ethoxzolamide and JWH-015; Triprolidine hydrochloride and Betamethasone; Triprolidine hydrochloride and Domperidone; Domperidone and Isotharine mesylate; Triprolidine hydrochloride and Quipazine, N-methyl-, dimaleate; Sodium Nitroprusside and Budesonide; Triamcinolone and 3-tropanyl-indole-3-carboxylate hydrochloride; Isotharine mesylate and m-iodobenzylguanidine hemisulfate; Ethoxzolamide and Lansoprazole; Sodium Nitroprusside and Isotharine mesylate; Beclomethasone and Betamethasone; Sodium Nitroprusside and Lansoprazole; Ethoxzolamide and Mianserin hydrochloride; Ethoxzolamide and Betamethasone; Ethoxzolamide and m-iodobenzylguanidine hemisulfate; Sodium Nitroprusside and Mianserin hydrochloride; Budesonide and 3-tropanyl-indole-3-carboxylate hydrochloride; Beclomethasone and Quipazine, N-methyl-, dimaleate; Ruthenium red and Lonidamine; Sodium Nitroprusside and Loxapine succinate; Triprolidine hydrochloride and Budesonide; Ethoxzolamide and Loxapine succinate; Triamcinolone and Cyproheptadine hydrochloride; Ethoxzolamide and Domperidone; 3-tropanyl-indole-3-carboxylate hydrochloride and PD168,077 maleate; Ruthenium red and Betamethasone; Ethoxzolamide and PD168,077 maleate; 3-tropanyl-indole-3-carboxylate hydrochloride and Isotharine mesylate; Budesonide and Isotharine mesylate; Benztropine mesylate and Isotharine mesylate; Triamcinolone and Quipazine, N-methyl-, dimaleate; Isotharine mesylate and Loxapine succinate; Ruthenium red and Benztropine mesylate; Domperidone and m-iodobenzylguanidine hemisulfate; Triamcinolone and Budesonide; Sodium Nitroprusside and U-83836 dihydrochloride; Ruthenium red and Triprolidine hydrochloride;

Tetradecylthioacetic acid and Budesonide; Sodium Nitroprusside and Cyproheptadine hydrochloride; Betamethasone and Quipazine, N-methyl-, dimaleate; 3-tropanyl-indole-3-carboxylate hydrochloride and Papaverine hydrochloride; Tetradecylthioacetic acid and Betamethasone; Ethoxzolamide and Isotharine mesylate; Tetradecylthioacetic acid and Isotharine mesylate; Lonidamine and Benztropine mesylate; Isotharine mesylate and Mianserin hydrochloride; 3-tropanyl-indole-3-carboxylate hydrochloride and Mianserin hydrochloride; Isotharine mesylate and Papaverine hydrochloride; Sodium Nitroprusside and Ethoxzolamide; Betamethasone and Isotharine mesylate; Lansoprazole and Loxapine succinate; Triamcinolone and Benztropine mesylate; Ethoxzolamide and Papaverine hydrochloride; Domperidone and Lansoprazole; Ruthenium red and Quipazine, N-methyl-, dimaleate; Beclomethasone and Isotharine mesylate; Mianserin hydrochloride and Papaverine hydrochloride; Sodium Nitroprusside and Lonidamine; Tetradecylthioacetic acid and Flutamide; Triprolidine hydrochloride and Beclomethasone; Mianserin hydrochloride and PD168,077 maleate; Triamcinolone and Lonidamine; Domperidone and Loxapine succinate; Beclomethasone and 3-tropanyl-indole-3-carboxylate hydrochloride; Lonidamine and Domperidone; Betamethasone and 3-tropanyl-indole-3-carboxylate hydrochloride; Benztropine mesylate and m-iodobenzylguanidine hemisulfate; Beclomethasone and Domperidone; Flutamide and Loxapine succinate; Tetradecylthioacetic acid and Triamcinolone; Tetradecylthioacetic acid and Quipazine, N-methyl-, dimaleate; Sodium Nitroprusside and Triprolidine hydrochloride; Ruthenium red and Isotharine mesylate; Triamcinolone and Domperidone; Tetradecylthioacetic acid and 3-tropanyl-indole-3-carboxylate hydrochloride; Ethoxzolamide and Budesonide; Tetradecylthioacetic acid and Lonidamine; Domperidone and Papaverine hydrochloride; Domperidone and Mianserin hydrochloride; Isotharine mesylate and PD168,077 maleate; Triprolidine hydrochloride and Benztropine mesylate; Ethoxzolamide and Triamcinolone; Ethoxzolamide and Ruthenium red; Sodium Nitroprusside and 3-tropanyl-indole-3-carboxylate hydrochloride; Lansoprazole and m-iodobenzylguanidine hemisulfate; Betamethasone and Benztropine mesylate; Loxapine succinate and Mianserin hydrochloride; Ethoxzolamide and Lonidamine; Benztropine mesylate and Papaverine hydrochloride; Triamcinolone and Isotharine mesylate; Ruthenium red and Triamcinolone; Domperidone and PD168,077 maleate; Triamcinolone and Beclomethasone; Ethoxzolamide and Triprolidine hydrochloride; Domperidone and Flutamide; Loxapine succinate and m-iodobenzylguanidine hemisulfate; 3-tropanyl-indole-3-carboxylate hydrochloride and Loxapine succinate; Budesonide and Quipazine, N-methyl-, dimaleate; Lonidamine and Quipazine, N-methyl-, dimaleate; Beclomethasone and Lonidamine; Tetradecylthioacetic acid and Benztropine mesylate; Sodium Nitroprusside and Domperidone; Cyproheptadine hydrochloride and Lonidamine; Ethoxzolamide and Benztropine mesylate; Tetradecylthioacetic acid and Triprolidine hydrochloride; Ruthenium red and Domperidone; Tetradecylthioacetic acid and Domperidone; Ethoxzolamide and Quipazine, N-methyl-, dimaleate; Budesonide and Benztropine mesylate; Loxapine succinate and PD168,077 maleate; Cyproheptadine hydrochloride and Quipazine, N-methyl-, dimaleate; 3-tropanyl-indole-3-carboxylate hydrochloride and m-iodobenzylguanidine hemisulfate; Beclomethasone and Cyproheptadine hydrochloride; Budesonide and Lonidamine; Benztropine mesylate and Loxapine succinate; Triamcinolone and Triprolidine hydrochloride; Papaverine hydrochloride and PD168,077 maleate; Sodium Nitroprusside and Benztropine mesylate; Betamethasone and Cyproheptadine hydrochloride; Triprolidine hydrochloride and Isotharine mesylate; Triprolidine hydrochloride and Flutamide; Triprolidine hydrochloride and Lonidamine; m-iodobenzylguanidine hemisulfate and PD168,077 maleate; Tetradecylthioacetic acid and (Z)-Gugglesterone; Lonidamine and 3-tropanyl-indole-3-carboxylate hydrochloride; Ethoxzolamide and 3-tropanyl-indole-3-carboxylate hydrochloride; Ethoxzolamide and Cyproheptadine hydrochloride; Beclomethasone and Benztropine mesylate; Tetradecylthioacetic acid and Cyproheptadine hydrochloride; Loxapine succinate and Papaverine hydrochloride; m-iodobenzylguanidine hemisulfate and Papaverine hydrochloride; Ruthenium red and Beclomethasone; Ruthenium red and Cyproheptadine hydrochloride; Ethoxzolamide and Tetradecylthioacetic acid; Benztropine mesylate and Domperidone; Lonidamine and Isotharine mesylate; Sodium Nitroprusside and Tetradecylthioacetic acid; Triamcinolone and Betamethasone; Triprolidine hydrochloride and Cyproheptadine hydrochloride; Betamethasone and Budesonide; Sodium Nitroprusside and Ruthenium red; Lonidamine and Flutamide; Isotharine mesylate and Lansoprazole; Triamcinolone and Flutamide; Flutamide and m-iodobenzylguanidine hemisulfate; Budesonide and Domperidone; 3-tropanyl-indole-3-carboxylate hydrochloride and Benztropine mesylate; Tetradecylthioacetic acid and Beclomethasone; Ruthenium red and Tetradecylthioacetic acid; Ethoxzolamide and Flutamide; JWH-015 and SA-57; JWH-015 and SA-47; JWH-133 and SA-57; JWH-015 and JNJ 1661010; JWH-133 and SA-47; HU-308 and SA-57; JWH-015 and URB-597; JWH-133 and JNJ 1661010; HU-308 and SA-47; L-759,656 and SA-57; JWH-015 and TAK 21d; JWH-133 and URB-597; HU-308 and JNJ 1661010; L-759,656 and SA-47; CGS 21680 and SA-57; JWH-015 and JZL 195; JWH-133 and TAK 21d; HU-308 and URB-597; L-759,656 and JNJ 1661010; CGS 21680 and SA-47; ATL 146e and SA-57; JWH-015 and PF 750; JWH-133 and JZL 195; HU-308 and TAK 21d; L-759,656 and URB-597; CGS 21680 and JNJ 1661010; ATL 146e and SA-47; ATL 313 and SA-57; JWH-133 and PF 750; HU-308 and JZL 195; L-759,656 and TAK 21d; CGS 21680 and URB-597; ATL 146e and JNJ 1661010; ATL 313 and SA-47; UK-432,097 and SA-57; HU-308 and PF 750; L-759,656 and JZL 195; CGS 21680 and TAK 21d; ATL 146e and URB-597; ATL 313 and JNJ 1661010; UK-432,097 and SA-47; TC-E 5005 and SA-57; L-759,656 and PF 750; CGS 21680 and JZL 195; ATL 146e and TAK 21d; ATL 313 and URB-597; UK-432,097 and JNJ 1661010; TC-E 5005 and SA-47; PF-2545920 hydrochloride and SA-57; CGS 21680 and PF 750; ATL 146e and JZL 195; ATL 313 and TAK 21d; UK-432,097 and URB-597; TC-E 5005 and JNJ 1661010; PF-2545920 hydrochloride and SA-47; TAK-063 and SA-57; ATL 313 and JZL 195; UK-432,097 and TAK 21d; TC-E 5005 and URB-597; PF-2545920 hydrochloride and JNJ 1661010; TAK-063 and SA-47; AMG 579 and SA-57; UK-432,097 and JZL 195; TC-E 5005 and TAK 21d; PF-2545920 hydrochloride and URB-597; TAK-063 and JNJ 1661010; AMG 579 and SA-47; L-741,626 and SA-57; TC-E 5005 and JZL 195; PF-2545920 hydrochloride and TAK 21d; TAK-063 and URB-597; AMG 579 and JNJ 1661010; L-741,626 and SA-47; Remoxipride and SA-57; PF-2545920 hydrochloride and JZL 195; TAK-063 and TAK 21d; AMG 579 and URB-597; L-741,626 and JNJ 1661010; Remoxipride and SA-47; Raclopride and SA-57; TAK-063 and JZL 195; AMG 579 and TAK 21d; L-741,626 and URB-597; Remoxipride and JNJ 1661010; Raclopride and SA-47; Nemonapride and SA-57; AMG 579 and JZL 195; L-741,626 and TAK 21d; Remoxipride and URB-597; Raclopride and JNJ 1661010; Nemonapride and SA-47; Fluticasone and SA-57; L-741,626 and JZL 195; Remoxipride and TAK 21d; Raclopride and URB-597; Nemonapride and JNJ 1661010; Fluticasone and SA-47; AZD 9567 and SA-57; Remoxipride and JZL 195; Raclopride and TAK 21d; Nemonapride and URB-597; Fluticasone and JNJ 1661010; AZD 9567 and SA-47; AL-438 and SA-57; Raclopride and JZL 195; Nemonapride and TAK 21d; Fluticasone and URB-597; AZD 9567 and JNJ 1661010; AL-438 and SA-47; Mapracorat and SA-57; Nemonapride and JZL 195; Fluticasone and TAK 21d; AZD 9567 and URB-597; AL-438 and JNJ 1661010; Mapracorat and SA-47; LGD-5552 and SA-57; Fluticasone and JZL 195; AZD 9567 and TAK 21d; AL-438 and URB-597; Mapracorat and JNJ 1661010; LGD-5552 and SA-47; AZD 9567 and JZL 195; AL-438 and TAK 21d; Mapracorat and URB-597; LGD-5552 and JNJ 1661010; AZD 9567 and PF 750; AL-438 and JZL 195; Mapracorat and TAK 21d; LGD-5552 and URB-597; AL-438 and PF 750; AZD 9567 and JWH-015; LGD-5552 and TAK 21d; Mapracorat and PF 750; AL-438 and JWH-015; LGD-5552 and PF 750; Mapracorat and JWH-015; AL-438 and JWH-133; AZD 9567 and HU-308, LGD-5552 and JWH-015; Mapracorat and JWH-133; AL-438 and HU-308; AZD 9567 and L-759,656; LGD-5552 and JWH-133; Mapracorat and HU-308; AL-438 and L-759,656; AZD 9567 and CGS 21680; LGD-5552 and HU-308; Mapracorat and L-759,656; AL-438 and CGS 21680; AZD 9567 and ATL 146e; LGD-5552 and L-759,656; Mapracorat and CGS 21680; AL-438 and ATL 146e; AZD 9567 and ATL 313; LGD-5552 and CGS 21680; Mapracorat and ATL 146e; AL-438 and ATL 313; AZD 9567 and UK-432,097; LGD-5552 and ATL 146e; Mapracorat and ATL 313; AL-438 and UK-432,097; AZD 9567 and TC-E 5005; LGD-5552 and ATL 313; Mapracorat and UK-432,097; AL-438 and TC-E 5005; AZD 9567 and PF-2545920 hydrochloride; LGD-5552 and UK-432,097; Mapracorat and TC-E 5005; AL-438 and PF-2545920 hydrochloride; AZD 9567 and TAK-063; Fluticasone and AMG 579; LGD-5552 and TC-E 5005; Mapracorat and PF-2545920 hydrochloride; AL-438 and TAK-063; AZD 9567 and AMG 579; Fluticasone and L-741,626; LGD-5552 and PF-2545920 hydrochloride; Mapracorat and TAK-063; AL-438 and AMG 579; AZD 9567 and L-741,626; Fluticasone and Remoxipride; LGD-5552 and TAK-063; Mapracorat and AMG 579; AL-438 and L-741,626; AZD 9567 and Remoxipride; Fluticasone and Raclopride; LGD-5552 and AMG 579; Mapracorat and L-741,626; AL-438 and Remoxipride; AZD 9567 and Raclopride; Fluticasone and Nemonapride; LGD-5552 and L-741,626; Mapracorat and Remoxipride; AL-438 and Raclopride; AZD 9567 and Nemonapride; LGD-5552 and Remoxipride; Mapracorat and Raclopride; AL-438 and Nemonapride; LGD-5552 and Raclopride; Mapracorat and Nemonapride; LGD-5552 and Nemonapride; ATL 146e and PF 750; CGS 21680 and JWH-015; LGD-5552 and JZL 195; AZD 9567 and JWH-133; Fluticasone and TAK-063; Nemonapride and AMG 579; ATL 313 and PF 750; ATL 146e and JWH-015; CGS 21680 and NTH-133; Fluticasone and PF-2545920 hydrochloride; Nemonapride and TAK-063; Raclopride and AMG 579; UK-432,097 and PF 750; ATL 313 and JWH-015; ATL 146e and JWH-133; CGS 21680 and HU-308; Fluticasone and TC-E 5005; Nemonapride and PF-2545920 hydrochloride; Raclopride and TAK-063; Remoxipride and AMG 579; TC-E 5005 and PF 750; UK-432,097 and JWH-015; ATL 313 and JWH-133; ATL 146e and HU-308; CGS 21680 and L-759,656; PF-2545920 hydrochloride and PF 750; TC-E 5005 and JWH-015; UK-432,097 and JWH-133; ATL 313 and HU-308; ATL 146e and L-759,656; TAK-063 and PF 750; PF-2545920 hydrochloride and JWH-015, TC-E 5005 and JWH-133; UK-432,097 and HU-308; ATL 313 and L-759,656; AMG 579 and PF 750; TAK-063 and JWH-015; PF-2545920 hydrochloride and JWH-133; TC-E 5005 and HU-308; UK-432,097 and L-759,656; L-741,626 and PF 750; AMG 579 and JWH-015; TAK-063 and JWH-133; PF-2545920 hydrochloride and HU-308; TC-E 5005 and L-759,656; Fluticasone and L-759,656; Nemonapride and CGS 21680; Raclopride and ATL 146e; Remoxipride and ATL 313; L-741,626 and UK-432,097; Fluticasone and CGS 21680; Nemonapride and ATL 146e; Raclopride and ATL 313; Remoxipride and UK-432,097; L-741,626 and TC-E 5005; Fluticasone and ATL 146e; Nemonapride and ATL 313; Raclopride and UK-432,097; Remoxipride and TC-E 5005; L-741,626 and PF-2545920 hydrochloride; Fluticasone and ATL 313; Nemonapride and UK-432,097; Raclopride and TC-E 5005; Remoxipride and PF-2545920 hydrochloride; L-741,626 and TAK-063; Fluticasone and UK-432,097; Nemonapride and TC-E 5005; Raclopride and PF-2545920 hydrochloride; Remoxipride and TAK-063; L-741,626 and AMG 579; Remoxipride and PF 750; L-741,626 and JWH-015; AMG 579 and JWH-133; TAK-063 and HU-308; PF-2545920 hydrochloride and L-759,656; TC-E 5005 and CGS 21680; Fluticasone and HU-308; Nemonapride and L-759,656; Raclopride and CGS 21680; Remoxipride and ATL 146e; L-741,626 and ATL 313; AMG 579 and UK-432,097; Raclopride and PF 750; Remoxipride and JWH-015; L-741,626 and JWH-133; AMG 579 and HU-308; TAK-063 and L-759,656; PF-2545920 hydrochloride and CGS 21680; TC-E 5005 and ATL 146e; Nemonapride and PF 750; Raclopride and JWH-015; Remoxipride and JWH-133; L-741,626 and HU-308; AMG 579 and L-759,656; TAK-063 and CGS 21680; PF-2545920 hydrochloride and ATL 146e; TC-E 5005 and ATL 313; Fluticasone and JWH-015; Nemonapride and JWH-133; Raclopride and HU-308; Remoxipride and L-759,656; L-741,626 and CGS 21680; AMG 579 and ATL 146e; TAK-063 and ATL 313; PF-2545920 hydrochloride and UK-432,097; Mapracorat and JZL 195; Fluticasone and JWH-133; Nemonapride and HU-308; Raclopride and L-759,656; Remoxipride and CGS 21680; L-741,626 and ATL 146e; AMG 579 and ATL 313; TAK-063 and UK-432,097; Fluticasone and PF 750; Nemonapride and JWH-015; Raclopride and JWH-133; Remoxipride and HU-308; L-741,626 and L-759,656; AMG 579 and CGS 21680; TAK-063 and ATL 146e; PF-2545920 hydrochloride and ATL 313; and/or TC-E 5005 and UK-432,097; or any other combination listed in Tables 4, 5, or 6.

As noted above, it is understood and herein contemplated the disclosed methods of treating a neurodegenerative order comprising administering a first therapeutic agent and a second therapeutic agent can further comprise the administration of additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 therapeutic agents (i.e., a third, fourth, fifth, sixth, seventh, eighth, ninth, tenth, etc. therapeutic agent). The addition therapeutic agent can be selected from any of the therapeutic agents disclosed herein including, but not limited to, (Z)-Gugglesterone; 3-tropanyl-indole-3-carboxylate hydrochloride; Beclomethasone; Benztropine mesylate; Betamethasone; Budesonide; Cyproheptadine hydrochloride; Domperidone; Ethoxzolamide; Flutamide; Hydrocortisone; Isotharine mesylate; JWH-015; JWH-133; HU-308; L-759,656; CGS 21680; ATL 146e; ATL 313; UK-432,097; TC-E 5005; SA-57; SA-47; JNJ 1661010; URB-597; TAK 21d; JZL 195; PF 750; PF-2545920 hydrochloride; TAK-063; AMG 579; L-741,626; Remoxipride; Raclopride; Nemonapride; LGD-5552; AZD 9567; Mapracorat; LGD-5552; AL-438; Lansoprazole; Lonidamine; Loxapine succinate; Meclizine; Mianserin hydrochloride; m-Iodobenzylguanidine hemisulfate; Papaverine hydrochloride; PD 168,077 maleate; Quipazine, N-methyl-, dimaleate; Ruthenium red; SB 203186; Sodium Nitroprusside; Tetradecylthioacetic acid; Triamcinolone; Triprolidine hydrochloride; U-83836 dihydrochloride; and Vinpocetine. It is understood and herein contemplated that one or more additional therapeutic agents can have an additive or synergistic therapeutic effect to the combination of the first and second therapeutic agents on the neurodegenerative disorder.

In one aspect, the screens disclosed herein identify compounds with known targets and pathways signaling pathways including said targets. By selecting compounds for use in combination that perturbate different targets or multiple target pathways, the effectiveness of the combination of therapeutic agents is synergistically enhanced. In one aspect, it is understood that multiple targets may modulate the activity of a given pathway. For example, as disclosed in Table 2 it is shown that the Muscarinic acetylcholine receptor M2, 5-hydroxytryptamine receptor 2A, Muscarinic acetylcholine receptor M1, D(1B) Dopamine Receptor, 5-hydroxytryptamine receptor 2A, 5-hydroxytryptamine receptor 2C, Histamine H2 Receptor, D(1A) Dopamine Receptor, 5-hydroxytryptamine receptor 7, 5-hydroxytryptamine receptor 6, Muscarinic acetylcholine receptor M5, Muscarinic acetylcholine receptor M3, Histamine H1 receptor, Alpha-1D adrenergic receptor, Alpha-1B adrenergic receptor, Alpha-1A adrenergic receptor, Beta-1 adrenergic receptor, 5-hydroxytryptamine receptor 5A, and Histone deacetylase 11 each modulate the calcium signaling pathway. Accordingly, it is contemplated herein that where a particular therapeutic agent modulates the activity of a particular target and that target is part of a particular pathway which is modulated by the modulated activity of the target; other therapeutic agents that bind to the same target or that bind targets that modulate the same pathway will have a similar therapeutic effect in the treatment of a neurodegenerative disease. It is further understood that the use of multiple therapeutic agents that bind to different targets within the same pathway can have a synergistic effect on the pathway.

Similarly, it is understood and herein contemplated that a modulation of a single target can modulate the activity of multiple pathways. For example as disclosed in Table 2, the 5-hydroxytryptamine receptor 2A is a component of the calcium signaling pathway, the inflammatory mediator regulation of TRP channels, gap junction pathway, and serotonergic synapse pathway. Thus, it is contemplated herein that where a particular therapeutic agent modulates the activity of a particular target (a first target) and that first target is part of multiple pathways which are modulated by the modulated activity of the first target; other therapeutic agents that bind to the same target or bind second targets that modulate the any of the same pathways as the first target will have a similar therapeutic effect in the treatment of a neurodegenerative disease.

Thus, in one aspect, disclosed herein are methods of treating a neurodegenerative disease comprising administering to a subject two or more therapeutic agents (for example, a first therapeutic agent and a second therapeutic agent), wherein the therapeutic agents perturbate one or more target pathways shown in Table 2, and wherein the combination of the first and second therapeutic agents has a synergistic protective effect on the neurodegenerative disorder. For example, in one aspect, disclosed herein are methods of treating a neurodegenerative disorder (such as Huntington's disease, Creutzfeldt-Jakob disease; Primary progressive aphasia; Frontotemporal lobar degeneration; Progressive supranuclear palsy; Friedreich's Ataxia, Alzheimer's disease, Parkinson's disease, Sinocerebellar ataxia, prion disease, age related dementia, Amyotrophic lateral sclerosis, and/or Batten disease) in a subject comprising administering to the subject a first therapeutic agent and a second therapeutic agent, wherein the first and second therapeutic agents (for example, a first and second small molecule) modulate the activity of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more pathways selected from the group consisting of Calcium signaling pathway, Inflammatory mediator regulation of TRP channels, cGMP-PKG signaling pathway, cAMP signaling pathway, Gap junction, Alcoholism., Rap1 signaling pathway, Serotonergic synapse, Amphetamine addiction, Dopaminergic synapse, Cocaine addiction, Parkinson's disease, Morphine addiction, Cholinergic synapse, PI3K-Akt signaling pathway, Ras signaling pathway, Purine metabolism, Endocytosis, AMPK signaling pathway, Pathways in cancer, Oxidative phosphorylation, Retrograde endocannabinoid signaling, Alzheimer's disease, Proximal tubule bicarbonate reclamation, Huntington's disease, Nitrogen metabolism, Oxytocin signaling pathway, Cell cycle, Transcriptional misregulation in cancer, Longevity regulating pathway-multiple species, MicroRNAs in cancer, Notch signaling pathway, MAPK signaling pathway, Epstein-Barr virus infection, and Viral carcinogenesis; and wherein the combination of therapeutic agents has a synergistic protective effect on the neurodegenerative disorder.

It is further understood and herein contemplated that multiple therapeutic agents are known in the art that have the same or similar effect on a given target. Therefore, where the modulation of a given target by a therapeutic agent is shown to have a protective effect, contemplated herein are other therapeutic agents that modulate the same target and can be substituted in a protective combination. In other words, where a therapeutic agent A has been identified to modulate a particular target Z, and where therapeutic agent A is shown to have a synergistic protective effect on a neurodegenerative disease when used in combination with therapeutic agent B, and wherein therapeutic agent C has been shown to modulate target Z in a similar way to molecule A, it is understood that the combination of molecules C and B will have the same synergistic protective effect for treating the same neurodegenerative disease as the combination of molecule A and B. Accordingly, substituting a therapeutic agent that binds to a given target with another therapeutic agent that binds the same target is contemplated herein.

Thus, in one aspect, disclosed herein are methods of treating a neurodegenerative disease comprising administering to a subject two or more therapeutic agents, wherein the therapeutic agents perturbate one or more of the targets listed in Table 1, and wherein the combination of therapeutic agents has a synergistic protective effect on the neurodegenerative disorder. For example, in one aspect, disclosed herein are methods of treating a neurodegenerative disorder (such as Huntington's disease, Creutzfeldt-Jakob disease; Primary progressive aphasia; Frontotemporal lobar degeneration; Progressive supranuclear palsy; Friedreich's Ataxia, Alzheimer's disease, Parkinson's disease, Sinocerebellar ataxia, prion disease, age related dementia, Amyotrophic lateral sclerosis, and/or Batten disease) in a subject comprising administering to the subject, two or more therapeutic agents, wherein the two or more therapeutic agents modulate the activity of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 3, 54, 55, 56, 57, 58, 59, 60, 61, 62, 63, 64, 65, 66, 67, 68, 69, 70, 71, 72, 73, 74, 75, or 76, or more targets selected from the group consisting of Adenosine receptor $A_{2A}$, Histamine H1 receptor, 5-hydroxytryptamine receptor 2A, Glucocorticoid receptor, Alpha-2C adrenergic receptor, D(3) dopamine receptor, D(2) dopamine receptor, 5-hydroxytryptamine receptor 2C, Muscarinic acetylcholine receptor M2, Muscarinic acetylcholine receptor M4, Muscarinic acetylcholine receptor M1, Alpha-2A adrenergic receptor, Alpha-2B adrenergic receptor, 5-hydroxytryptamine receptor 2B, Muscarinic acetylcholine receptor M5, Muscarinic acetylcholine receptor M3, 5-hydroxytryptamine receptor 7, Histamine H4 receptor, Sodium-dependent dopamine transporter, D(1A) dopamine receptor, Alpha-1D adrenergic receptor, 5-hydroxytryptamine receptor 6, 5-hydroxytryptamine receptor 1A, Sodium-dependent serotonin transporter, 5-hydroxytryptamine receptor 1D, Sodium-dependent noradrenaline transporter, Alpha-1B adrenergic receptor, D(1B) dopamine receptor, Alpha-1A adrenergic receptor, Histamine H2 receptor, Beta-1 adrenergic receptor, Integral membrane protein DGCR2/IDD, Histone deacetylase 6, Carbonic anhydrase 14, Annexin A1, Microtubule-associated protein tau, Kappa-type opioid receptor, Histone deacetylase 9, 5-hydroxytryptamine receptor 5A, Carbonic anhydrase 9, Carbonic anhydrase 5A, mitochondrial, Carbonic anhydrase 13, Histone deacetylase 1, 5-hydroxytryptamine receptor 3A, 5-hydroxytryptamine receptor 1E, Histone deacetylase 8, Sigma non-opioid intracellular receptor 1, Potassium voltage-gated channel subfamily H member 2, 5-hydroxytryptamine receptor 1F, Aryl hydrocarbon receptor, Carbonic anhydrase 7, cGMP-inhibited 3',5'-cyclic phosphodiesterase A, 5-hydroxytryptamine receptor 1B, Histone deacetylase 10, Atrial natriuretic peptide receptor 1, Carbonic anhydrase 6 (EC 4.2.1.1), Histone deacetylase 7, Histone deacetylase 4, Histone deacetylase 11, Corticosteroid-binding globulin, Carbonic anhydrase 12, Beta-2 adrenergic receptor, D(4) dopamine receptor, Carbonic anhydrase 5B, mitochondrial, Carbonic anhydrase 2, Carbonic anhydrase 4, Cannabinoid receptor 2, Histone deacetylase 5, Potassium-transporting ATPase alpha chain 1, Androgen receptor, cAMP and cAMP-inhibited cGMP 3',5'-cyclic phosphodiesterase 10A, Carbonic anhydrase 1, Cannabinoid receptor 1, Histone deacetylase 2, cAMP-specific 3',5'-cyclic phosphodiesterase 4B, and/or Histone deacetylase 3.

It is understood and herein contemplated that the disclosed therapeutic agent combinations can be effective for treating the neurodegenerative disease or symptoms associated with one neurodegenerative disease and not others (i.e., the combination has a synergistic protective effect for one neurodegenerative disease but does not have the same or similar synergistic protective effect for a second neurodegenerative disease). In one aspect, disclosed herein are methods of treating Huntington's disease in a subject comprising administering to the subject two or more therapeutic agents wherein the therapeutic agents comprise Betamethasone and Lonidamine; Sodium Nitroprusside and Triamcinolone; Sodium Nitroprusside and Betamethasone; Sodium Nitroprusside and Beclomethasone; Ethoxzolamide and Beclomethasone; Triprolidine hydrochloride and Betamethasone; Domperidone and Isotharine mesylate; Sodium Nitroprusside and Budesonide; Isotharine mesylate and m-iodobenzylguanidine hemisulfate; Sodium Nitroprusside and Isotharine mesylate; Sodium Nitroprusside and Lansoprazole; Ethoxzolamide and Betamethasone; Sodium Nitroprusside and Mianserin hydrochloride; Beclomethasone and Quipazine, N-methyl-, dimaleate; Sodium Nitroprusside and Loxapine succinate; Ethoxzolamide and Loxapine succinate; Ethoxzolamide and Domperidone; Ruthenium red and Betamethasone; 3-tropanyl-indole-3-carboxylate hydrochloride and Isotharine mesylate; Benztropine mesylate and Isotharine mesylate; Isotharine mesylate and Loxapine succinate; Domperidone and m-iodobenzylguanidine hemisulfate; Sodium Nitroprusside and U-83836 dihydrochloride; Tetradecylthioacetic acid and Budesonide; Betamethasone and Quipazine, N-methyl-, dimaleate; Tetradecylthioacetic acid and Betamethasone; Tetradecylthioacetic acid and Isotharine mesylate; Isotharine mesylate and Mianserin hydrochloride; Isotharine mesylate and Papaverine hydrochloride; Betamethasone and Isotharine mesylate; Triamcinolone and Benztropine mesylate; Domperidone and Lansoprazole; Beclomethasone and Isotharine mesylate; Sodium Nitroprusside and Lonidamine; Triprolidine hydrochloride and Beclomethasone; Triamcinolone and Lonidamine; Beclomethasone and 3-tropanyl-indole-3-carboxylate hydrochloride; Betamethasone and 3-tropanyl-indole-3-carboxylate hydrochloride; Beclomethasone and Domperidone; Tetradecylthioacetic acid and Triamcinolone; Sodium Nitroprusside and Triprolidine hydrochloride; Triamcinolone and Domperidone; Ethoxzolamide and Budesonide; Domperidone and Papaverine hydrochloride; Isotharine mesylate and PD168,077 maleate; Ethoxzolamide and Triamcinolone; Sodium Nitroprusside and 3-tropanyl-indole-3-carboxylate hydrochloride; Betamethasone and Benztropine mesylate; Ethoxzolamide and Lonidamine; Triamcinolone and Isotharine mesylate; Domperidone and PD168,077 maleate; Ethoxzolamide and Triprolidine hydrochloride; Loxapine succinate and m-iodobenzylguanidine hemisulfate; Budesonide and Quipazine, N-methyl-, dimaleate; Beclomethasone and Lonidamine; Sodium Nitroprusside and Domperidone; Ethoxzolamide and Benztropine mesylate; Ruthenium red and Domperidone; Ethoxzolamide and Quipazine, N-methyl-, dimaleate; Loxapine succinate and PD168,077 maleate; 3-tropanyl-indole-3-carboxylate hydrochloride and m-iodobenzylguanidine hemisulfate; and/or any of the combinations listed in Tables 3, 4, 5, and 6.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

In one aspect, it is contemplated herein that the disclosed compound combinations can be formulated as a single composition and administered simultaneously, or as separate compositions and administered simultaneously, concurrently, or as a first compound administration followed by a second compound administration 15, 20, 25, 30, 45 min, 1, 2, 3, 4, 5, 6, 7, 8, 9, 10, 11, 12, 13, 14, 15, 16, 17, 18, 19, 20, 21, 22, 23, 24, 36, 48, 60, 72, 84, or 96 hours after the first compound is administered. When administered concurrently or sequentially, the compounds can be administered via the same or different routes and at the same or different sites.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Connecting Neuronal Cell Protective Pathways and Drug Combinations in a Huntington's Disease Model Through the Application of Quantitative Systems Pharmacology a) Results (1) Characterization of Neuronal Cell Protective Compounds in the STHdh$^{Q111}$ Model The well-established STHdh$^{Q111}$ cell model for HD was employed to identify compounds that can protect neuronal cells from mHTT-dependent cell death. In this model, serum deprivation (which mimics the clinical stress of growth factor deprivation) of the STHdh$^{Q111}$ cells containing mHTT results in cell death, whereas under the same conditions the STHdh$^{Q7}$ wild type cells are resistant to cell death. The propidium iodide (PI) readout enables an unbiased assessment of cell death by measuring an irreversible step that is common to all cytotoxic mechanisms. Under serum-depleted conditions, ~50 percent of the STHdh$^{Q111}$ cells underwent cell death as evident by positive nuclear PI staining, compared to less than 10 percent of the wild type STHdh$^{Q7}$ cells. From screens of the LOPAC1280 library, the NCATS Pharmaceutical Collection, and a library of 83 compounds computationally predicted to be neuroprotective (see Methods), the activity of 32 compounds was confirmed (FIG. 2).

Interestingly, the level of protection afforded by the majority of the compounds did not reach 100%, exhibiting plateaus in the dose response curves between 30% and 50%. The neuronal cell protection observed was not an overestimate simply due to an undetectable loss of dead cells, and that partial protection was not simply due to limited solubility within the efficacious dose range. The spectral properties of PI are red shifted relative to the majority of small molecule compounds, thus avoiding compound interference (quenching). Analysis of the hit compounds in an LDH-based cell death assay with a format and readout distinct from that of PI showed similar curves for the hit compounds as seen in the PI assay. For a subset of compounds, the direct effect on quenching the PI signal was examined and found that quenching did not occur. These results indicate that the partial protection was an outcome of compound perturbation of mHTT-induced biology under these experimental conditions.

The DrugBank and STITCH databases were searched for the canonical targets of the 32 active compounds. Ten compounds had no known targets in either database; the remaining 23 displayed a diverse range of canonical mechanisms of action targeting 75 proteins on a number of pathways (Tables 1 and 2). Many of the canonical targets have known functions that are critical to CNS activity. For example, histamine receptors, the target of 7 hit compounds, are associated with multiple neuropsychiatric disorders. Receptors of the neurotransmitters serotonin and dopamine are also targets of several of the hit compounds. Nine active compounds did not share any targets with other hits in the screen, indicating that either multiple mechanisms are capable of conferring neuronal cell protection or some of the active compounds operate through shared non-canonical mechanisms.

TABLE 1

Targets from DrugBank and STITCH for 35 identified probes

| Target ID | Uniprot ID | Target name | Probes Count | Probes |
|---|---|---|---|---|
| T1 | P35367 | Histamine H1 receptor | 7 | Meclizine, Domperidone, Benzatropine, Loxapine, Cyproheptadine, Mianserin, Triprolidine |
| T2 | P28223 | 5-hydroxytryptamine receptor 2A | 6 | Loxapine, Benzatropine, Domperidone, Quipazine, N-methyl-, dimaleate, Mianserin, Cyproheptadine |
| T3 | P04150 | Glucocorticoid receptor | 6 | Triamcinolone, Budesonide, Betamethasone, Hydrocortisone, Beclomethasone, Prednisolone |
| T4 | P18825 | Alpha-2C adrenergic receptor | 5 | Mianserin, Benzatropine, Loxapine, Domperidone, Cyproheptadine |
| T5 | P35462 | D(3) dopamine receptor | 5 | Domperidone, Cyproheptadine, Benzatropine, Loxapine, Mianserin |
| T6 | P14416 | D(2) dopamine receptor | 5 | Benzatropine, Mianserin, Domperidone, Loxapine, Cyproheptadine |
| T7 | P28335 | 5-hydroxytryptamine receptor 2C | 5 | Mianserin, Loxapine, Benzatropine, Quipazine, N-methyl-, dimaleate, Cyproheptadine |
| T8 | P08172 | Muscarinic acetylcholine receptor M2 | 4 | Benzatropine, Loxapine, Cyproheptadine, Mianserin |
| T9 | P08173 | Muscarinic acetylcholine receptor M4 | 4 | Loxapine, Cyproheptadine, Benzatropine, Mianserin |
| T10 | P11229 | Muscarinic acetylcholine receptor M1 | 4 | Mianserin, Loxapine, Cyproheptadine, Benzatropine |
| T11 | P08913 | Alpha-2A adrenergic receptor | 4 | Benzatropine, Mianserin, Cyproheptadine, Loxapine |
| T12 | P18089 | Alpha-2B adrenergic receptor | 4 | Benzatropine, Cyproheptadine, Loxapine, Mianserin |
| T13 | P41595 | 5-hydroxytryptamine receptor 2B | 4 | Benzatropine, Quipazine, N-methyl-, dimaleate, Mianserin, Cyproheptadine |
| T14 | P08912 | Muscarinic acetylcholine receptor M5 | 4 | Cyproheptadine, Loxapine, Mianserin, Benzatropine |
| T15 | P20309 | Muscarinic acetylcholine receptor M3 | 4 | Cyproheptadine, Benzatropine, Loxapine, Mianserin |
| T16 | P34969 | 5-hydroxytryptamine receptor 7 | 3 | Loxapine, Cyproheptadine, Mianserin |

TABLE 1-continued

Targets from DrugBank and STITCH for 35 identified probes

| Target ID | Uniprot ID | Target name | Probes Count | Probes |
|---|---|---|---|---|
| T17 | Q9H3N8 | Histamine H4 receptor | 3 | Cyproheptadine, Mianserin, Loxapine |
| T18 | Q01959 | Sodium-dependent dopamine transporter | 3 | Loxapine, Benzatropine, Mianserin |
| T19 | P21728 | D(1A) dopamine receptor | 3 | Cyproheptadine, Loxapine, Mianserin |
| T20 | P25100 | Alpha-1D adrenergic receptor | 3 | Cyproheptadine, Mianserin, Benzatropine |
| T21 | P50406 | 5-hydroxytryptamine receptor 6 | 3 | Cyproheptadine, Mianserin, Loxapine |
| T22 | P08908 | 5-hydroxytryptamine receptor 1A | 3 | Mianserin, Loxapine, Cyproheptadine |
| T23 | P31645 | Sodium-dependent serotonin transporter | 3 | Quipazine, N-methyl-, dimaleate, Loxapine, Mianserin |
| T24 | P28221 | 5-hydroxytryptamine receptor ID | 2 | Mianserin, Loxapine |
| T25 | P23975 | Sodium-dependent noradrenaline transporter | 2 | Loxapine, Mianserin |
| T26 | P35368 | Alpha-1B adrenergic receptor | 2 | Loxapine, Mianserin |
| T27 | P21918 | D(1B) dopamine receptor | 2 | Loxapine, Mianserin |
| T28 | P35348 | Alpha-1A adrenergic receptor | 2 | Loxapine, Mianserin |
| T29 | P25021 | Histamine H2 receptor | 2 | Cyproheptadine, Loxapine |
| T30 | P08588 | Beta-1 adrenergic receptor | 2 | Loxapine, Isoetarine |
| T31 | P98153 | Integral membrane protein DGCR2/IDD | 1 | Ethoxzolamide |
| T32 | Q9UBN7 | Histone deacetylase 6 | 1 | Vorinostat |
| T33 | Q9ULX7 | Carbonic anhydrase 14 | 1 | Ethoxzolamide |
| T34 | P04083 | Annexin A1 | 1 | Hydrocortisone |
| T35 | P10636 | Microtubule-associated protein tau | 1 | Lansoprazole |
| T36 | P41145 | Kappa-type opioid receptor | 1 | Mianserin |
| T37 | Q9UKV0 | Histone deacetylase 9 | 1 | Vorinostat |
| T38 | P47898 | 5-hydroxytryptamine receptor 5A | 1 | Loxapine |
| T39 | Q16790 | Carbonic anhydrase 9 | 1 | Ethoxzolamide |
| T40 | P35218 | Carbonic anhydrase 5A, mitochondrial | 1 | Ethoxzolamide |
| T41 | Q8N1Q1 | Carbonic anhydrase 13 | 1 | Ethoxzolamide |
| T42 | Q13547 | Histone deacetylase 1 | 1 | Vorinostat |
| T43 | P46098 | 5-hydroxytryptamine receptor 3A | 1 | Loxapine |
| T44 | P28566 | 5-hydroxytryptamine receptor 1E | 1 | Loxapine |
| T45 | Q9BY41 | Histone deacetylase 8 | 1 | Vorinostat |
| T46 | Q99720 | Sigma non-opioid intracellular receptor 1 | 1 | Benzatropine |
| T47 | Q12809 | Potassium voltage-gated channel subfamily H member 2 | 1 | Domperidone |
| T48 | P30939 | 5-hydroxytryptamine receptor 1F | 1 | Mianserin |
| T49 | P35869 | Aryl hydrocarbon receptor | 1 | Flutamide |
| T50 | P43166 | Carbonic anhydrase 7 | 1 | Ethoxzolamide |
| T51 | Q14432 | cGMP-inhibited 3',5'-cyclic phosphodiesterase A | 1 | Papaverine |
| T52 | P28222 | 5-hydroxytryptamine receptor 1B | 1 | Loxapine |
| T53 | Q969S8 | Histone deacetylase 10 | 1 | Vorinostat |
| T54 | P16066 | Atrial natriuretic peptide receptor 1 | 1 | Nitroprusside |
| T55 | P23280 | Carbonic anhydrase 6 (EC 4.2.1.1) | 1 | Ethoxzolamide |
| T56 | Q8WUI4 | Histone deacetylase 7 | 1 | Vorinostat |
| T57 | P56524 | Histone deacetylase 4 | 1 | Vorinostat |
| T58 | Q96DB2 | Histone deacetylase 11 | 1 | Vorinostat |
| T59 | P08185 | Corticosteroid-binding globulin | 1 | Hydrocortisone |
| T60 | O43570 | Carbonic anhydrase 12 | 1 | Ethoxzolamide |
| T61 | P07550 | Beta-2 adrenergic receptor | 1 | Isoetarine |
| T62 | P21917 | D(4) dopamine receptor | 1 | Loxapine |
| T63 | Q9Y2D0 | Carbonic anhydrase 5B, mitochondrial | 1 | Ethoxzolamide |
| T64 | P00918 | Carbonic anhydrase 2 | 1 | Ethoxzolamide |
| T65 | P22748 | Carbonic anhydrase 4 | 1 | Ethoxzolamide |
| T66 | P34972 | Cannabinoid receptor 2 | 1 | JWH-015 |
| T67 | Q9UQL6 | Histone deacetylase 5 | 1 | Vorinostat |
| T68 | P20648 | Potassium-transporting ATPase alpha chain 1 | 1 | Lansoprazole |
| T69 | P10275 | Androgen receptor | 1 | Flutamide |
| T70 | Q9Y233 | cAMP and cAMP-inhibited cGMP 3',5'-cyclic phosphodiesterase 10A | 1 | Papaverine |
| T71 | P00915 | Carbonic anhydrase 1 | 1 | Ethoxzolamide |
| T72 | P21554 | Cannabinoid receptor 1 | 1 | JWH-015 |
| T73 | Q92769 | Histone deacetylase 2 | 1 | Vorinostat |

TABLE 1-continued

Targets from DrugBank and STITCH for 35 identified probes

| Target ID | Uniprot ID | Target name | Probes Count | Probes |
|---|---|---|---|---|
| T74 | Q07343 | cAMP-specific 3',5'-cyclic phosphodiesterase 4B | 1 | Papaverine |
| T75 | O15379 | Histone deacetylase 3 | 1 | Vorinostat |

Note:
Targets were ranked by the number of interacting probes, probes interact with each target were listed in the corresponding row.

TABLE 2

Mapping of 35 identified probes and targets in KEGG human pathways

| Index | Pathway Name | Probes count | Targets in this pathway | Probes in this pathway |
|---|---|---|---|---|
| 1 | Calcium signaling pathway | 9 | T8, T2, T10, T29, T7, T31, T20, T14, T17, T22, T15, T32, T21, T16, T28, T1, T64, T40, T30 | Mianserin, Domperidone, Benzatropine, Cyproheptadine, (Quipazine, N-methyl-, dimaleate), Loxapine, Isoetarine, Meclizine, Triprolidine |
| 2 | Inflammatory mediator regulation of TRP channels | 8 | T1, T7, T2, T14 | Mianserin, Domperidone, Benzatropine, Cyproheptadine, (Quipazine, N-methyl-, dimaleate), Loxapine, Meclizine, Triprolidine |
| 3 | cGMP-PKG signaling pathway | 8 | T56, T4, T53, T21, T32, T12, T13, T28, T64, T30 | Nitroprusside, Mianserin, Domperidone, Benzatropine, Cyproheptadine, Loxapine, Papaverine, Isoetarine |
| 4 | cAMP signaling pathway | 8 | T8, T56, T10, T29, T46, T54, T53, T25, T50, T22, T20, T32, T6, T23, T77, T64 | Nitroprusside, Mianserin, Domperidone, Benzatropine, Cyproheptadine, Loxapine, Papaverine, Isoetarine |
| 5 | Gap junction | 7 | T2, T7, T14, T20, T32, T6 | Mianserin, Domperidone, Benzatropine, Cyproheptadine, (Quipazine, N-methyl-, dimaleate), Loxapine, Isoetarine |
| 6 | Alcoholism | 6 | T34, T58, T78, T60, T19, T55, T44, T76, T47, T6, T70, T39, T20, T59 | Vorinostat, Mianserin, Domperidone, Benzatropine, Cyproheptadine, Loxapine |
| 7 | Rap1 signaling pathway | 6 | T75, T6 | Mianserin, Domperidone, Benzatropine, JWH- 015, Cyproheptadine, Loxapine |
| 8 | Serotonergic synapse | 6 | T45, T46, T2, T25, T54, T7, T14, T50, T22, T17, T23, T40, T24 | Mianserin, Domperidone, Benzatropine, Cyproheptadine, Quipazine, N-methyl-, dimaleate, Loxapine |
| 9 | Amphetamine addiction | 5 | T20, T19, T44 | Loxapine, Benzatropine, Vorinostat, Cyproheptadine, Mianserin |
| 10 | Dopaminergic synapse | 5 | T5, T19, T29, T20, T6, T65 | Loxapine, Domperidone, Benzatropine, Cyproheptadine, Mianserin |
| 11 | Cocaine addiction | 5 | T20, T19, T6 | Loxapine, Domperidone, Benzatropine, Cyproheptadine, Mianserin |
| 12 | Parkinson's disease | 5 | T20, T19, T6 | Loxapine, Domperidone, Benzatropine, Cyproheptadine, Mianserin |
| 13 | Morphine addiction | 4 | T77, T20, T53, T73 | Loxapine, Papaverine, Mianserin, Cyproheptadine |
| 14 | Cholinergic synapse | 4 | T8, T9, T15, T10, T16 | Loxapine, Benzatropine, Cyproheptadine, Mianserin |
| 15 | PI3K-Akt signaling pathway | 4 | T8, T10 | Loxapine, Benzatropine, Cyproheptadine, Mianserin |
| 16 | Ras signaling pathway | 3 | T17 | Loxapine, Mianserin, Cyproheptadine |
| 17 | Purine metabolism | 2 | T77, T56, T53, T73 | Papaverine, Nitroprusside |
| 18 | Endocytosis | 2 | T64, T32 | Loxapine, Isoetarine |
| 19 | AMPK signaling pathway | 2 | T30 | Loxapine, Mianserin |
| 20 | Pathways in cancer | 2 | T72, T76, T44 | Flutamide, Vorinostat |
| 21 | Oxidative phosphorylation | 1 | T71 | Lansoprazole |
| 22 | Retrograde endocannabinoid | 1 | T75 | JWH-015 |
| 23 | Alzheimer's disease | 1 | T37 | Lansoprazole |
| 24 | Proximal tubule bicarbonate | 1 | T67, T68 | Ethoxzolamide |
| 25 | Huntington's disease | 1 | T76, T44 | Vorinostat |

TABLE 2-continued

Mapping of 35 identified probes and targets in KEGG human pathways

| Index | Pathway Name | Probes count | Targets in this pathway | Probes in this pathway |
|---|---|---|---|---|
| 26 | Nitrogen metabolism | 1 | T67, T68, T66, T52, T57, T35, T74, T41, T63, T42, T43 | Ethoxzolamide |
| 27 | Oxytocin signaling pathway | 1 | T56 | Nitroprusside |
| 28 | Cell cycle | 1 | T76, T44 | Vorinostat |
| 29 | Transcriptional misregulation in cancer | 1 | T76, T44 | Vorinostat |
| 30 | Longevity regulating pathway - multiple species | 1 | T76, T44 | Vorinostat |
| 31 | MicroRNAs in cancer | 1 | T59, T44 | Vorinostat |
| 32 | Notch signaling pathway | 1 | T76, T44 | Vorinostat |
| 33 | MAPK signaling pathway | 1 | T37 | Lansoprazole |
| 34 | Epstein-Barr virus infection | 1 | T59, T70, T76, T44 | Vorinostat |
| 35 | Viral carcinogenesis | 1 | T34, T60, T78, T55, T44, T76, T47, T58, T70, T39, T59 | Vorinostat |

Note:
Pathways were ranked by the number of mapped probes, probe targets that mapped into each pathway and the corresponding probes were listed in the corresponding pathway row. Target information for each target ID is listed in Table 1.

(2) Combinations Show Enhanced Protective Effects.

The diversity of canonical mechanisms of the compounds exhibiting protection and the partial maximal protection for any one compound indicated the presence of more than one protective mechanism, where the sufficiency for any one mechanism to afford complete protection in an individual cell varied across the cell population. To explore this further, it was investigated whether the efficacy of neuronal cell protection could be enhanced with pairwise combinations of compounds with different canonical mechanisms. The combination screen was implemented using 25 of the confirmed LOPAC hits and ethoxzolamide, one of the computationally predicted hits. 268 compound pairs were screened with each compound at a single concentration that was on or near the plateau of the activity of the respective individual compound, and compared the percent recovery (i.e., protection from cell death) of compound combinations to that of the individual compounds (See FIG. 3 as an example). From the 268 pairs tested, 109 pairs showed enhanced toxicity as determined by the loss of cells from the well using the criteria of total cell number being below 3SD of the total number of cells in the DMSO controls. For the remaining 159 pairs of combinations (Table 3), it was determined if the combination effect was additive, synergistic, or antagonistic by calculating a combination index using the Bliss Independence Model. 61 combination pairs in this screen had synergistic interactions (FIG. 4a, Table 4) while 90 pairs were calculated to be antagonistic and 8 appeared to be additive. The synergistic assessment of the single point analysis was verified by selecting 20 pairs of compounds, testing them in concentration response experiments, and calculating the combination index. All of the pairs tested in this analysis were determined to be synergistic (FIG. 4b). This test gave provided the confidence in the assessment of the other combinations used in the single point experiments.

TABLE 3

Combination Pairs

| Combination Number | Combination |
|---|---|
| 1 | Betamethasone__Lonidamine |
| 2 | Sodium Nitroprusside__Triamcinolone |
| 3 | Sodium Nitroprusside__Betamethasone |
| 4 | Sodium Nitroprusside__Beclomethasone |
| 5 | Ethoxzolamide__Beclomethasone |
| 6 | Triprolidine hydrochloride__Betamethasone |
| 7 | Domperidone__Isotharine mesylate |
| 8 | Sodium Nitroprusside__Budesonide |
| 9 | Isotharine mesylate__m-Iodobenzylguanidine hemisulfate |
| 10 | Sodium Nitroprusside__Isotharine mesylate |
| 11 | Sodium Nitroprusside__Lansoprazole |
| 12 | Ethoxzolamide__Betamethasone |
| 13 | Sodium Nitroprusside__Mianserin hydrochloride |
| 14 | Beclomethasone__Quipazine, N-methyl-, dimaleate |
| 15 | Sodium Nitroprusside__Loxapine succinate |
| 16 | Ethoxzolamide__Loxapine succinate |
| 17 | Ethoxzolamide__Domperidone |
| 18 | Ruthenium red__Betamethasone |
| 19 | 3-tropanyl-indole-3-carboxylate hydrochloride__Isotharine mesylate |
| 20 | Benztropine mesylate__Isotharine mesylate |
| 21 | Isotharine mesylate__Loxapine succinate |
| 22 | Domperidone__m-Iodobenzylguanidine hemisulfate |
| 23 | Sodium Nitroprusside U-83836 dihydrochloride |
| 24 | Tetradecylthioacetic acid__Budesonide |
| 25 | Betamethasone__Quipazine, N-methyl-, dimaleate |
| 26 | Tetradecylthioacetic acid__Betamethasone |
| 27 | Tetradecylthioacetic acid__Isotharine mesylate |
| 28 | Isotharine mesylate__Mianserin hydrochloride |
| 29 | Isotharine mesylate__Papaverine hydrochloride |
| 30 | Betamethasone__Isotharine mesylate |
| 31 | Triamcinolone__Benztropine mesylate |
| 32 | Domperidone__Lansoprazole |
| 33 | Beclomethasone__Isotharine mesylate |
| 34 | Sodium Nitroprusside__Lonidamine |

TABLE 3-continued

Combination Pairs

| Combination Number | Combination |
|---|---|
| 35 | Triprolidine hydrochloride_Beclomethasone |
| 36 | Triamcinolone_Lonidamine |
| 37 | Beclomethasone_3-tropanyl-indole-3-carboxylate hydrochloride |
| 38 | Betamethasone_3-tropanyl-indole-3-carboxylate hydrochloride |
| 39 | Beclomethasone_Domperidone |
| 40 | Tetradecylthioacetic acid_Triamcinolone |
| 41 | Sodium Nitroprusside_Triprolidine hydrochloride |
| 42 | Triamcinolone_Domperidone |
| 43 | Ethoxzolamide_Budesonide |
| 44 | Domperidone_Papaverine hydrochloride |
| 45 | Isotharine mesylate_PD168,077 maleate |
| 46 | Ethoxzolamide_Triamcinolone |
| 47 | Sodium Nitroprusside_3-tropanyl-indole-3-carboxylate hydrochloride |
| 48 | Betamethasone_Benztropine mesylate |
| 49 | Ethoxzolamide_Lonidamine |
| 50 | Triamcinolone_Isotharine mesylate |
| 51 | Domperidone_PD168,077 maleate |
| 52 | Ethoxzolamide_Triprolidine hydrochloride |
| 53 | Loxapine succinate_m-Iodobenzylguanidine hemisulfate |
| 54 | Budesonide_Quipazine, N-methyl-dimaleate |
| 55 | Beclomethasone_Lonidamine |
| 56 | Sodium Nitroprusside_Domperidone |
| 57 | Ethoxzolamide_Benztropine mesylate |
| 58 | Ruthenium red_Domperidone |
| 59 | Ethoxzolamide_Quipazine, N-methyl-, dimaleate |
| 60 | Loxapine succinate_PD168,077 maleate |
| 61 | 3-tropanyl-indole-3-carboxylate hydrochloride_m-Iodobenzylguanidine hemisu |
| 62 | Budesonide_Lonidamine |
| 63 | Triamcinolone_Triprolidine hydrochloride |
| 64 | Sodium Nitroprusside_Benztropine mesylate |
| 65 | Triprolidine hydrochloride_Isotharine mesylate |
| 66 | Triprolidine hydrochloride_Lonidamine |
| 67 | Tetradecylthioacetic acid_(Z)-Gugglesterone |
| 68 | Ethoxzolamide_3-tropanyl-indole-3-carboxylate hydrochloride |
| 69 | Beclomethasone_Benztropine mesylate |
| 70 | Loxapine succinate_Papaverine hydrochloride |
| 71 | Ruthenium red_Beclomethasone |
| 72 | Ethoxzolamide_Tetradecylthioacetic acid |
| 73 | Lonidamine_Isotharine mesylate |
| 74 | Triamcinolone_Betamethasone |
| 75 | Betamethasone_Budesonide |
| 76 | Lonidamine_Flutamide |
| 77 | Triamcinolone_Flutamide |
| 78 | Budesonide_Domperidone |
| 79 | Tetradecylthioacetic acid + Beclomethasone |
| 80 | Ethoxzolamide_Flutamide |
| 81 | Ruthenium red_Budesonide |
| 82 | Ruthenium red_3-tropanyl-indole-3-carboxylate hydrochloride |
| 83 | Triprolidine hydrochloride_3-tropanyl-indole-3-carboxylate hydrochloride |
| 84 | Beclomethasone_Budesonide |
| 85 | Ethoxzolamide_JWH-015 |
| 86 | Triprolidine hydrochloride_Domperidone |
| 87 | Triprolidine hydrochloride_Quipazine, N-methyl-, dimaleate |
| 88 | Triamcinolone_3-tropanyl-indole-3-carboxylate hydrochloride |
| 89 | Ethoxzolamide_Lansoprazole |
| 90 | Beclomethasone_Betamethasone |
| 91 | Ethoxzolamide_Mianserin hydrochloride |
| 92 | Ethoxzolamide_m-Iodobenzylguanidine hemisulfate |
| 93 | Budesonide_3-tropanyl-indole-3-carboxylate hydrochloride |
| 94 | Ruthenium red_Lonidamine |
| 95 | Triprolidine hydrochloride_Budesonide |
| 96 | Triamcinolone_Cyproheptadine hydrochloride |
| 97 | 3-tropanyl-indole-3-carboxylate hydrochloride PD168, 077 maleate |
| 98 | Ethoxzolamide_PD168,077 maleate |
| 99 | Budesonide_Isotharine mesylate |
| 100 | Triamcinolone_Quipazine, N-methyl-, dimaleate |
| 101 | Ruthenium red_Benztropine mesylate |
| 102 | Triamcinolone_Budesonide |
| 103 | Ruthenium red_Triprolidine hydrochloride |
| 104 | Sodium Nitroprusside_Cyproheptadine hydrochloride |
| 105 | 3-tropanyl-indole-3-carboxylate hydrochloride_Papaverine hydrochloride |
| 106 | Ethoxzolamide_Isotharine mesylate |
| 107 | Lonidamine_Benztropine mesylate |
| 108 | 3-tropanyl-indole-3-carboxylate hydrochloride_Mianserin hydrochloride |
| 109 | Sodium Nitroprusside_Ethoxzolamide |
| 110 | Lansoprazole_Loxapine succinate |
| 111 | Ethoxzolamide Papaverine hydrochloride |
| 112 | Ruthenium red_Quipazine, N-methyl-, dimaleate |
| 113 | Mianserin hydrochloride_Papaverine hydrochloride |
| 114 | Tetradecylthioacetic acid_Flutamide |
| 115 | Mianserin hydrochloride_PD168,077 maleate |
| 116 | Domperidone_Loxapine succinate |
| 117 | Lonidamine_Domperidone |
| 118 | Benztropine mesylate_m-Iodobenzylguanidine hemisulfate |
| 119 | Flutamide_Loxapine succinate |
| 120 | Tetradecylthioacetic acid_Quipazine, N-methyl-, dimaleate |
| 121 | Ruthenium red_Isotharine mesylate |
| 122 | Tetradecylthioacetic acid_3-tropanyl-indole-3-carboxylate hydrochloride |
| 123 | Tetradecylthioacetic acid_Lonidamine |
| 124 | Domperidone_Mianserin hydrochloride |
| 125 | Triprolidine hydrochloride_Benztropine mesylate |
| 126 | Ethoxzolamide_Ruthenium red |
| 127 | Lansoprazole_m-Iodobenzylguanidine hemisulfate |
| 128 | Loxapine succinate_Mianserin hydrochloride |
| 129 | Benztropine mesylate_Papaverine hydrochloride |
| 130 | Ruthenium red_Triamcinolone |
| 131 | Triamcinolone_Beclomethasone |
| 132 | Domperidone_Flutamide |
| 133 | 3-tropanyl-indole-3-carboxylate hydrochloride_Loxapine succinate |
| 134 | Lonidamine_Quipazine, N-methyl-dimaleate |
| 135 | Tetradecylthioacetic acid_Benztropine mesylate |
| 136 | Cyproheptadine hydrochloride_Lonidamine |
| 137 | Tetradecylthioacetic acid_Triprolidine hydrochloride |
| 138 | Tetradecylthioacetic acid_Domperidone |
| 139 | Budesonide_Benztropine mesylate |
| 140 | Cyproheptadine hydrochloride_Quipazine,N-methyl- |

TABLE 3-continued

Combination Pairs

| Combination Number | Combination |
|---|---|
| 141 | Beclomethasone__Cyproheptadine hydrochloride |
| 142 | Benztropine mesylate__Loxapine succinate |
| 143 | Papaverine hydrochloride__PD168,077 maleate |
| 144 | Betamethasone__Cyproheptadine hydrochloride |
| 145 | Triprolidine hydrochloride__Flutamide |
| 146 | m-Iodobenzylguanidine hemisulfate__PD168,077 maleate |
| 147 | Lonidamine__3-tropanyl-indole-3-carboxylate hydrochloride |
| 148 | Ethoxzolamide__Cyproheptadine hydrochloride |
| 149 | Tetradecylthioacetic acid__Cyproheptadine hydrochloride |
| 150 | m-Iodobenzylguanidine hemisulfate__Papaverine hydrochloride |
| 151 | Ruthenium red__Cyproheptadine hydrochloride |
| 152 | Benztropine mesylate__Domperidone |
| 153 | Sodium Nitronprusside__Tetradecylthioacetic |
| 154 | Triprolidine hydrochloride__Cyproheptadine hydrochloride |
| 155 | Sodium Nitroprusside__Ruthenium red |
| 156 | Isotharine mesylate__Lansoprazole |
| 157 | Flutamide__m-Iodobenzylguanidine hemisulfate |
| 158 | 3-tropanyl-indole-3-carboxylate hydrochloride__Benztropine mesylate |
| 159 | Ruthenium red__Tetradecylthioacetic acid |

TABLE 4

Synergistic compounds

| Combination Number | Combination | Avg Percent Recovery | Std | n* | Avg Combi Ratio | Std | Median BCI |
|---|---|---|---|---|---|---|---|
| 1 | Betamethasone__Lonidamine | 84.68 | 6.12 | 4 | 1.98 | 0.62 | 1.39 |
| 2 | Sodium Nitroprusside__Triamcinolone | 89.08 | 4.62 | 5 | 1.89 | 0.34 | 1.34 |
| 3 | Sodium Nitroprusside__Betamethasone | 96.89 | 4.67 | 5 | 1.81 | 0.39 | 1.27 |
| 4 | Sodium Nitroprusside__Beclomethasone | 94.51 | 2.60 | 5 | 1.78 | 0.26 | 1.26 |
| 5 | Ethoxzolamide__Beclomethasone | 86.85 | 2.49 | 5 | 1.72 | 0.11 | 1.23 |
| 6 | Triprolidine hydrochloride__Betamethasone | 91.41 | 2.80 | 4 | 1.59 | 0.28 | 1.22 |
| 7 | Domperidone__Isotharine mesylate | 78.69 | 12.41 | 4 | 1.79 | 0.12 | 1.20 |
| 8 | Sodium Nitroprusside__Budesonide | 100.88 | 1.04 | 5 | 1.50 | 0.08 | 1.19 |
| 9 | Isotharine mesylate__m-Iodobenzylguanidine hemisulfate | 71.92 | 6.76 | 4 | 1.86 | 0.06 | 1.17 |
| 10 | Sodium Nitroprusside__Isotharine mesylate | 80.63 | 5.73 | 5 | 1.87 | 0.36 | 1.17 |
| 11 | Sodium Nitroprusside__Lansoprazole | 82.22 | 6.02 | 4 | 1.56 | 0.08 | 1.17 |
| 12 | Ethoxzolamide__Betamethasone | 77.30 | 33.72 | 6 | 1.55 | 0.02 | 1.15 |
| 13 | Sodium Nitroprusside__Mianserin hydrochloride | 75.42 | 8.10 | 4 | 1.63 | 0.20 | 1.14 |
| 14 | Beclomethasone__Quipazine, N-methyl-, dimaleate | 79.64 | 2.89 | 2 | 1.66 | 0.15 | 1.14 |
| 15 | Sodium Nitroprusside__Loxapine succinate | 80.46 | 2.19 | 4 | 1.49 | 0.03 | 1.13 |
| 16 | Ethoxzolamide__Loxapine succinate | 74.43 | 4.13 | 4 | 1.38 | 0.03 | 1.13 |
| 17 | Ethoxzolamide__Domperidone | 81.30 | 17.04 | 6 | 1.68 | 0.27 | 1.12 |
| 18 | Ruthenium red__Betamethasone | 79.17 | 7.01 | 4 | 1.51 | 0.34 | 1.12 |
| 19 | 3-tropanyl-indole-3-carboxylate hydrochloride Isotharine mesylate | 69.62 | 3.52 | 4 | 1.76 | 0.08 | 1.12 |
| 20 | Benztropine mesylate__Isotharine mesylate | 65.81 | 2.06 | 4 | 1.71 | 0.24 | 1.12 |
| 21 | Isotharine mesylate__Loxapine succinate | 80.01 | 4.50 | 4 | 1.48 | 0.06 | 1.11 |
| 22 | Domperidone__m-Iodobenzylguanidine hemisulfate | 72.00 | 3.99 | 4 | 1.64 | 0.04 | 1.11 |
| 23 | Sodium Nitroprusside__U-83836 dihydrochloride | 84.34 | 2.71 | 5 | 1.45 | 0.12 | 1.11 |
| 24 | Tetradecylthioacetic acid__Budesonide | 96.68 | 1.02 | 4 | 1.43 | 0.07 | 1.11 |
| 25 | Betamethasone__Quipazine,N-methyl-,dimaleate | 83.07 | 0.57 | 2 | 1.50 | 0.12 | 1.11 |
| 26 | Tetradecylthioacetic acid__Betamethasone | 85.04 | 3.50 | 4 | 1.42 | 0.19 | 1.11 |
| 27 | Tetradecylthioacetic acid__Isotharine mesylate | 88.66 | 4.19 | 2 | 1.39 | 0.08 | 1.10 |
| 28 | Isotharine mesylate__Mianserin hydrochloride | 73.47 | 5.54 | 4 | 1.60 | 0.34 | 1.10 |
| 29 | Isotharine mesylate__Papaverine hydrochloride | 74.95 | 6.28 | 4 | 1.57 | 0.02 | 1.10 |
| 30 | Betamethasone__Isotharine mesylate | 82.64 | 9.58 | 2 | 1.48 | 0.04 | 1.10 |
| 31 | Triamcinolone__Benztropine mesylate | 74.81 | 0.50 | 2 | 1.31 | 0.30 | 1.09 |
| 32 | Domperidone__Lansoprazole | 79.79 | 12.84 | 4 | 1.51 | 0.11 | 1.08 |
| 33 | Beclomethasone__Isotharine mesylate | 77.04 | 5.53 | 2 | 1.47 | 0.01 | 1.08 |
| 34 | Sodium Nitroprusside__Lonidamine | 66.90 | 22.35 | 5 | 1.39 | 0.09 | 1.08 |
| 35 | Triprolidine hydrochloride__Beclomethasone | 86.17 | 3.73 | 4 | 1.42 | 0.15 | 1.08 |
| 36 | Triamcinolone__Lonidamine | 58.55 | 8.25 | 4 | 1.72 | 0.49 | 1.07 |
| 37 | Beclomethasone__3-tropanyl-indole-3-carboxylate hydrochloride | 78.29 | 3.15 | 2 | 1.53 | 0.01 | 1.07 |
| 38 | Betamethasone__3-tropanyl-indole-3-carboxylate hydrochloride | 82.88 | 8.42 | 2 | 1.49 | 0.02 | 1.07 |
| 39 | Beclomethasone__Domperidone | 83.70 | 0.17 | 2 | 1.42 | 0.02 | 1.07 |
| 40 | Tetradecylthioacetic acid__Triamcinolone | 77.97 | 5.99 | 4 | 1.32 | 0.29 | 1.07 |
| 41 | Sodium Nitroprusside__Triprolidine hydrochloride | 86.41 | 5.97 | 5 | 1.46 | 0.25 | 1.07 |
| 42 | Triamcinolone__Domperidone | 73.41 | 1.45 | 2 | 1.25 | 0.01 | 1.07 |

TABLE 4-continued

Synergistic compounds

| Combination Number | Combination | Avg Percent Recovery | Std | n* | Avg Combi Ratio | Std | Median BCI |
|---|---|---|---|---|---|---|---|
| 43 | Ethoxzolamide_Budesonide | 87.19 | 3.45 | 6 | 1.29 | 0.03 | 1.07 |
| 44 | Domperidone_Papaverine hydrochloride | 75.42 | 11.88 | 4 | 1.58 | 0.19 | 1.07 |
| 45 | Isotharine mesylate_PD168,077 maleate | 71.38 | 2.48 | 4 | 1.57 | 0.15 | 1.07 |
| 46 | Ethoxzolamide_Triamcinolone | 61.43 | 7.36 | 6 | 1.54 | 0.33 | 1.06 |
| 47 | Sodium Nitroprusside_3-tropanyl-indole-3-carboxvlate hydrochloride | 68.86 | 12.35 | 5 | 1.53 | 0.13 | 1.06 |
| 48 | Betamethasone_Benztropine mesylate | 85.13 | 0.92 | 2 | 1.44 | 0.29 | 1.05 |
| 49 | Ethoxzolamide_Lonidamine | 64.69 | 6.30 | 6 | 1.61 | 0.37 | 1.05 |
| 50 | Triamcinolone_Isotharine mesylate | 61.87 | 12.97 | 2 | 1.39 | 0.12 | 1.05 |
| 51 | Domperidone_PD168,077 maleate | 72.46 | 5.13 | 4 | 1.55 | 0.17 | 1.04 |
| 52 | Ethoxzolamide_Triprolidine hydrochloride | 77.82 | 7.22 | 6 | 1.29 | 0.17 | 1.04 |
| 53 | Loxapine succinate_m-Iodobenzylguanidine hemisulfate | 73.76 | 2.68 | 4 | 1.36 | 0.00 | 1.04 |
| 54 | Budesonide_Quipazine, N-methyl-, dimaleate | 85.41 | 12.39 | 2 | 1.25 | 0.12 | 1.04 |
| 55 | Beclomethasone_Lonidamine | 69.30 | 21.92 | 4 | 1.37 | 0.03 | 1.03 |
| 56 | Sodium Nitroprusside_Domperidone | 61.74 | 25.78 | 5 | 1.26 | 0.37 | 1.03 |
| 57 | Ethoxzolamide_Benztropine mesylate | 58.69 | 10.99 | 6 | 1.46 | 0.23 | 1.02 |
| 58 | Ruthenium red Domperidone | 80.82 | 1.76 | 2 | 1.37 | 0.05 | 1.01 |
| 59 | Ethoxzolamide_Quipazine, N-methyl-, dimaleate | 60.16 | 7.97 | 4 | 1.59 | 0.17 | 1.01 |
| 60 | Loxapine succinate_PD168,077 maleate | 75.92 | 2.61 | 4 | 1.40 | 0.01 | 1.01 |
| 61 | 3-tropanyl-indole-3-carboxylate hydrochloride m-Iodobenzylguanidine hemisulfate | 61.79 | 2.27 | 4 | 1.57 | 0.07 | 1.01 |

*Compound combinations were run at least once on two different days. n = the total number of combination samples analyzed. An n = 2 indictes a combination was run only once on each of the two days.

Bliss independence (additivity) exists when the effects of compounds are statistically independent: applying one compound neither enhances nor diminishes the effects of the other. Whereas independence implies completely separate mechanisms, synergism and antagonism each imply a relationship between mechanisms, either within cells, across the population, or both. Antagonism at the population level can occur between compounds that share a therapeutic target and therefore compete with each other. Similarly, synergy can arise from mutually exclusive mechanisms manifested in non-overlapping cell subpopulations. Any given cell can respond to only one compound in the synergistic pair, minimizing the number of cells that are redundantly protected by both compounds. The results of the combination screens support these mechanisms. Forty-five of the 90 antagonistic pairs of compounds identified in the screen have known targets. Fifteen of these pairs (33%) are compounds that share at least one target. In contrast, target sharing is observed in only 2 of the 41 synergistic pairs (5%) with known targets.

(3) Inferring Protection-Relevant Pathways from the Compounds' Canonical Mechanisms.

The mechanistic diversity and synergistic effects of the compounds affording protection from mHTT-induced cell death indicated functional interrelationships among their targets. Synergy can arise from mechanistic interactions within the cell if two compounds affect distinct upstream effectors of a common mechanism. Each provides partial protection to the cell, and both, when combined, can confer sufficient protection to permit survival. Alternatively, targets on the same pathway can be heterogeneously expressed in a correlated fashion within the population, causing some cells to modulate the targeted pathway in response to one compound, and other cells to modulate the same pathway through an alternative mechanism. Assays with binary readouts, such as the PI assay used here, mask the mechanistic origins of synergy. Pathway analysis was turned to in order to investigate whether the observed synergy results from pathway convergence within cells, or from mutually exclusive modulation of pathways across a heterogeneous population.

Sixteen compounds were associated with the 41 synergistic pairs that had known targets. In 21 of these synergistic pairs, the compound targets shared at least one pathway as annotated in the KEGG database. The canonical targets for compounds in 10 of these 21 pairs converged on either the cAMP/PKA signaling pathway, the cGMP/PKG signaling pathway, or both (FIG. 5 and Table 5). No other pathway contained targets of more than four synergistic pairs, as was seen in both calcium signaling and Gap junction pathways.

TABLE 5

Synergistic compound pairs that converge on PKA/PKG signaling

| Combination | Compound 1 MOA | Compound 2 MOA |
|---|---|---|
| Sodium Nitroprusside_Loxapine succinate | Nitric oxide synthase | D2/3 receptor antagonist |
| Sodium Nitroprusside_Domperidone | Nitric oxide synthase | D2/3 receptor antagonist |
| Sodium Nitroprusside_Mianserin HCl | Nitric oxide synthase | 5HT and a-2C adrenergic antagonist |
| Isoetarine mesylate_Loxapine succinate | b-1/2 adrenergic receptor agonist | D2/3 receptor antagonist |

TABLE 5-continued

Synergistic compound pairs that converge on PKA/PKG signaling

| Combination | Compound 1 MOA | Compound 2 MOA |
|---|---|---|
| Isoetarine mesylate_Papaverine HCl | b-1/2 adrenergic receptor agonist | PDE10A inhibitor |
| Domperidone_Papaverine HCl | D2/3 receptor antagonist | PDE10A inhibitor |
| Isoetarine mesylate_Mianserin HCl | b-1/2 adrenergic receptor agonist | 5HT and a-2C adrenergic antagonist |
| Sodium Nitroprusside_Isoetarine mesylate | Nitric oxide synthase | b-1/2 adrenergic receptor agonist |
| Benztropine mesylate_Isoetarine mesylate | M1 receptor antagonist | b-1/2 adrenergic receptor agonist |
| Domperidone_Isoetarine mesylate | D2/3 receptor antagonist | b-1/2 adrenergic receptor agonist |

As disclosed herein, synergistic neuronal cell protection can arise in pairs of compounds that had the same effect on cAMP or cGMP signaling, but through distinct complementary mechanisms. For example, isotharine is an agonist of the β1 adrenergic receptor (($\beta_1$AR), which couples to Gs and stimulates conversion of ATP to cAMP by adenylate cyclase (AC). Benzatropine is an antagonist of the M1 muscarinic receptor, blocking the Gi-coupled inhibition of AC activity. Thus, both compounds have the potential to increase PKA activity, but through different mechanisms: Isoetarine stimulates AC, and benzatropine antagonizes an AC inhibitor. Another example is the synergistic combination of domperidone and papaverine. Similar to benzatropine, domperidone can elevate cAMP levels by antagonizing D2R. Papaverine inhibits the phosphodiesterases PDE4B and 10A, reducing the hydrolysis of cAMP into AMP. The net effect of this combination is to increase cAMP levels and PKA activity through two complementary mechanisms. Thus, increasing cAMP levels and correspondingly activated PKA levels or by analogy cGMP/PKG levels can lead to cytoprotection. Multiple compounds targeting the same pathway is distinct from multiple compounds interacting with the same target. Whereas in the latter compounds can compete for the same target site and thus do not lead to enhanced modulation of the target, modulating different points on a pathway can result in synergy enabling more control in regulating the output of the pathway.

Because cAMP/PKA signaling is a key pathway involved in cell survival and has been implicated in the pathophysiology of HD, it was tested whether these synergistic compounds can be working through augmenting cAMP and activating PKA. The ability of benztropine, domperidone, isoetarine, loxapine, mianserin, papaverine, and sodium nitroprusside to modulate cAMP and phospho-PKA levels in the STHdh$^{Q111}$ cells was assessed. cAMP levels were measured 15, 30, and 120 minutes after initial compound treatment in the presence of serum, which paralleled the pre-treatment stage of the PI assay, as it was anticipated that cAMP induction would be a relatively rapid response. All compounds, except for mianserin, showed at least a 2-fold increase in cAMP over the DMSO control at 15 minutes, which returned to control levels within 2 hours (FIG. 6). Though only isotharine showed a statistically significant increase in cAMP levels at 15 and 30 minutes, the overall profile of increased levels at 15 mins and the gradual decrease over time indicated that a transient induction of cAMP did occur shortly after initial compound treatment. Sodium nitroprusside, which primarily acts through stimulating cGMP, also produced an increase in cAMP. This 2-fold increase in cAMP by the protective compounds contrasted the 250-fold increase in cAMP levels induced by forskolin. Interestingly, forskolin did not show up as a hit in the LOPAC screen, nor did it show any protective effects when subsequently tested as a control in the PI assay run in parallel with the cAMP analysis.

To determine if PKA may be involved in the protective effect of these compounds, the STHdh$^{Q111}$ cells were incubated with benztropine, domperidone, isoetarine, loxapine, mianserin, papaverine, and sodium nitroprusside in the presence the PKA inhibitor H89 under the standard PI protection assay conditions. H89 has been used extensively in the literature as a selective and potent inhibitor of PKA. If the protection from cell death by these compounds involved activation of PKA, then the addition of an inhibitor of PKA would be expected to reverse the protective effects of the compounds. Co-incubation of 10 μM H89 with the Gi-coupled GPCR antagonists domperidone, loxapine, and mianserin resulted in 56, 52, and 35 percent reduction, respectively, in the level of protection, while the Gs-coupled agonist isoetarine resulted in a 34 percent reduction, the PDE inhibitor papaverine a 55 percent reduction, and the s-GC agonist sodium nitroprusside a 17 percent reduction compared to compound alone (FIG. 7a). Since the primary canonical mechanism of sodium nitroprusside is activation of PKG, and given that H89 is ~10-fold selective for PKA over PKG, the absence of a marked effect with sodium nitroprusside is not unexpected. The relatively lower effect of H89 on the PKG activator sodium nitroprusside compared to the PKA activators is consistent with the canonical mechanisms of these compounds. To confirm inhibition of PKA activity by H89 under the conditions of the PI assay, the levels of nuclear pCREB were measured using high content analysis. Consistent with the heterogeneity seen in the response of the STHdh$^{Q111}$ cells to protection by the compounds, a heterogeneous distribution of pCREB levels was also detected. The levels of pCREB were decreased in the presence of 10 μM H89 in all cases indicating inhibition of PKA activity (FIG. 7b). While H89 has been used extensively as a selective and potent inhibitor of PKA to understand the biology of PKA signal transduction, it has been reported that H89 has other effects as well. To address this, the effects of PKI, a reportedly more selective PKA inhibitor, were also tested on the activity of these compounds, however, PKI by itself was toxic to the STHdh$^{Q111}$ cells which overshadowed any potential effect in inhibiting protection.

To further assess PKA activation by these compounds, the levels of PKA phosphorylated at threonine 197 (pPKA) in the catalytic subunit were quantified using high-content analysis. The pPKA levels were examined at 24 hours after serum free conditions since this was the condition where the protection of the compounds was measured. The levels of cytoplasmic pPKA were lower in the STHdh$^{Q111}$ cells relative to the STHdh$^{Q7}$ (FIG. 8), consistent with the hypothesis that elevated pPKA was associated with neuronal cell survival. Benztropine, isoetarine, loxapine, mianserin, and sodium nitroprusside exhibited a concentration-dependent increase in cytoplasmic pPKA approaching the levels of the wild type STHdh$^{Q7}$ cells. The concentration response for domperidone, papaverine and forskolin was less pronounced. Interestingly, the nuclear pPKA levels in the STHdh$^{Q111}$ cells were higher than in the STHdh$^{Q7}$ cells (FIG. 8). None of the compounds showed a marked concentration-dependent decrease in the nuclear levels. The increase in pPKA correlated with the percent recovery for these compounds (FIG. 9); however, the concentration response curves between the compounds were distinct from each other. If pPKA were the only factor responsible for the protective effects of these compounds, then the concentration response curves for the pPKA effect on recovery would be expected to be the same indicating additional mechanisms were involved in the protection phenotype for these compounds.

(4) Some Compounds can be Protecting by Non-Canonical Mechanisms.

The pathway analysis was based on using canonical mechanisms of action for the identified compounds; however, it was hypothesized that the protective activity of some of the compounds might be through alternative mechanisms, as well. Several structurally distinct carbonic anhydrase inhibitors were present in the library of compounds, but only one of them, ethoxzolamide, showed protective activity in the PI assay. To determine if ethoxzolamide was acting through its canonical carbonic anhydrase inhibition mechanism, its methyl sulfonyl analog was synthesized in which the amine group that is critical for the carbonic anhydrase inhibition by this drug class was replaced by an isosteric methyl group. The methyl sulfonyl analog of ethoxzolamide was approximately 7-times more potent than ethoxzolamide itself and equally efficacious (FIG. 10). Though the methyl sulfonyl analog for inhibition of carbonic anhydrase was not tested directly, the activity of the methyl sulfonyl analog indicates that the protective activity observed with ethoxzolamide can be due to a distinct mechanism and not due to its canonical carbonic anhydrase inhibition.

b) Discussion

Despite major technological advances in genome editing, differentiation of patient-derived iPSCs, and recapitulation of complex disease phenotypes in human microphysiological models (i.e., organs-on-a-chip), the knowledge of disease mechanism is often the limiting factor for optimizing therapeutic strategies for patient cohorts. QSP has emerged as an approach to address this void. Commensurate with advances in the development of clinically relevant models, and complementary to systematic genetic approaches, an increased use of mechanistically diverse and well annotated chemical libraries was anticipated, especially those containing FDA approved drugs, to probe disease mechanism. This small molecule approach has the potential to lead directly to drug repurposing and optimal drug combination strategies that maximize efficacy and minimize toxicity, as well as to serve as a starting point for selecting targeted libraries for additional discovery efforts. Thus, this approach plays an increasingly important role in mechanistic studies and drug development efforts to address many of the 7,000 rare diseases that exist worldwide. In the case of HD, screening identified several drugs having well-defined canonical modes of action that partially protected against mutant HTT-induced neuronal cell death. Many combinations exhibited significant synergy, indicating a functional network association among them involving PKA (PKG) signaling.

The analysis reported here indicated that cAMP/PKA signaling was involved in the protection of neuronal cells from mHTT-induced toxicity in the STHdh$^{Q111}$ model. Several lines of evidence from the literature indicate that altered activity of the PKA (PKG) signaling is directly pathogenic and does not simply represent a beneficial compensatory mechanism for averting mHTT-induced cell death. Single cell analysis employing an optical pulse-chase method has demonstrated that neuron-to-neuron variation in protein homeostasis capacity (i.e., proteasome activity) contributes substantially to a given cell's susceptibility to the effects of misfolded proteins. Specifically pertinent to HD, striatal neurons were, on average, more vulnerable to disease-causing misfolded mHTT and cleared a corresponding -mHTT reporter more slowly than cortical and cerebellar neurons. Statistical modeling linked intrinsic protein homeostasis capacity in striatal, cortical, and cerebellar neurons to their vulnerability to mHTT-induced degeneration. Furthermore, animal models of HD show that mHTT stress-induced impairment of the proteasomal capacity in the striatum is associated with lowered PKA activity. This reduced PKA activity is caused by the accumulation of negative regulatory PKA subunits that are normally controlled by proteasomal degradation. Since it has also been shown that full proteasomal activity depends upon PKA phosphorylation, a feed-forward loop of diminished PKA and proteasomal activity has been indicated as an important component of HD pathogenesis. Consistent with the results presented here, pharmacologic intervention corroborated this hypothesis, as agents that increase cAMP and activate PKA restored proteasomal activity and ameliorated motor impairment. By analogy, very recent results indicate a similar feed-forward loop operative in other tauopathies. The results show a lower level of cytosolic pPKA in the mHTT cells relative to the wt cells under stress conditions, and the association of increasing pPKA with increasing recovery from cell death is consistent with the observations in the literature. However, the fact that the PKA recovery curves were different among the compounds indicates that factors in addition to activation of PKA per se can also contribute to neuronal cell protection.

Forskolin also increased pPKA to levels that were associated with protection by the other compounds yet itself was not protective, further indicating that additional factors are important for protection. Since forskolin was unable to induce protection from cell death in STHdh$^{Q111}$ cells, it appears that regulatory nuances beyond simply a global and robust stimulation of cAMP downstream of specific GPCR machinery are necessary to elicit a protective response.

The canonical targets of a number of compounds converge on a plausible mechanism for neuroprotection from mHTT toxicity, and that the literature supports the role of this mechanism in HD. However, this mechanism alone neither explains all of the results nor provides a clear path to an HD therapeutic. Given the pleiotropic nature of mHTT, and evidenced by the synergistic results that do not involve cAMP/PKA signaling, other protective mechanisms exist. In addition, the canonical mechanisms are not the only mechanisms through which compounds protect from mHTT toxicity, as exemplified by the activity of the ethoxzolamide analog. Although mHTT is pleiotropic, small molecule compounds can also interact with multiple targets; it has been estimated that most drugs bind to on average 6 targets.

The work presented here represents the first two iterations of the QSP approach starting with mechanism-annotated probe compounds and a clinically relevant phenotypic assay, and leading to the identification of disease-relevant pathways. An integrated chemogenomic strategy using information about probes that modulate a clinical phenotype can lead to testable hypotheses and provide insights to targetable biological mechanisms for disease treatment. This is the first report of such an approach applied to HD. This initial chemogenomics analysis can be extended to include medium spiny neurons derived from human iPSC in the context of human neuronal microphysiological systems that recapitulate critical cell intrinsic and extrinsic microenvironments.

c) Materials and Methods (1) Cells

Conditionally immortalized mutant Huntingtin (mHTT) homozygous knock-in mouse STHdh$^{Q111}$ cells and the isogenic wild type STHdh$^{Q7}$ cells were a gift from Marcy MacDonald and are described in Trettel et al. Cells were cultured in DMEM (25 mM glucose, 4 mM L-glutamine) supplemented with 10% FBS, 5 mM sodium pyruvate and 0.3% Pen-Strep at 33° C. and 5% $CO_2$. The stress conditions for testing compounds involved incubation of the cells in serum-free medium at 37° C. and 5% $CO_2$.

Compound Preparations

The LOPAC library and individual test compounds were from Sigma-Aldrich (St. Louis, Mo.) except for meclizine, prednisolone, and ethoxzolamide which were from Santa Cruz (Dallas, Tex.), and U83836E which was from Abcam (Cambridge, Mass.). Compounds were dissolved in DMSO (Alpha Aesar, Fisher Scientific) to 10 mM stocks. For screening, the LOPAC library was first diluted in medium containing 5% DMSO and then 5 µl were added to 45 µl of cells. For concentration response curves, 2- or 3-step serial dilutions in DMSO were prepared, a 20-fold intermediate dilution was made in medium, and 5 µl of this solution were added to cells in 45 µl medium. For combination treatments, compounds were mixed together in DMSO before being diluted in medium as above for addition to the cells.

Synthesis of 6-ethoxy-2-(methylsulfonyl) benzo[d]thiazole (3) Reagents for the synthesis of the methylsulfonyl analog of ethoxzolamide were purchased from Sigma-Aldrich (St. Louis, Mo.). The synthesis was performed in two steps as follows:

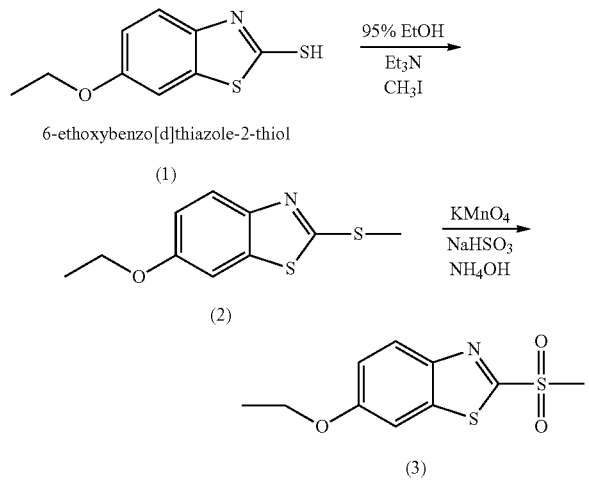

Synthesis of 6-ethoxy-2-(methylthio) benzo[d]thiazole (2)

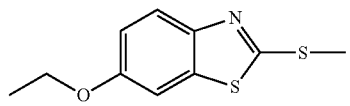

(2)

Starting with (1) from Sigma-Aldrich, the protocol described by Rosen et al. was followed to synthesize (2).

Synthesis of 6-ethoxy-2-(methyl sulfonyl) benzo[d]thiazole (3)

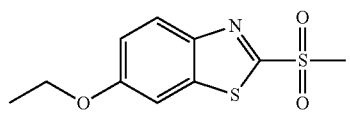

(3)

To a solution of 6-ethoxy-2-(methylthio) benzo[d]thiazole (2) (0.5 g, 2.219 mmoles) dissolved in acetic acid (6 mL) was added KMnO4 (0.596 g, 3.772 mmoles) in water (8 mL). The resulting mixture is stirred at room temp for 5 days. The reaction mixture was quenched with NaHSO3 (0.346 g, 3.33 mmoles) and the pH of the solution adjusted to 8 with NH$_4$OH. The reaction mixture was then extracted with EtOAC. Organic solvents washed with water, brine, dried over sodium sulfate. Solvents evaporated to give 0.5 g (87%) of (3) as a white solid. (1HNMR (400 MHz, DMSO-d6) δ 1.39 (t, 3H, J=7.2 Hz), 3.54 (s, 3H), 4.15 (q, 2H, J=7.2 Hz), 7.29 (dd, 1H, J=8.8 Hz &2.4 Hz), 7.87 (d, 1H, J=2.4 Hz), 8.13 (dd, 1H, J=8.8 Hz & 0.4 Hz) AT-IR cm-1 2981, 2920, 1597, 1553, 1486, 1471, 1402, 1312, 1250, 1228, 1139, 1116, 1068, 1037, 1018, 963, 935, 883, 858, 816, 760, 690, 610. HRMS (TOF MS Ap+) m/z calcd for C10H12NO3 S2 (258.0259). Found (258.0265)).

(2) 384-Well PI Assay

Cells were cultured for 4 days in complete medium at 33° C. and 5% $CO_2$ before plating in Greiner Bio-One TC, clear bottom, black walled 384-well plates (50 µl) at 3,000 cells per well. Cells were allowed to attach in complete medium at 33° C. and 5% $CO_2$ for 24 hr. Prior to compound treatment, medium was removed and the cells washed once with PBS (pH=7.4) after which 45 µl of complete medium was added. Compounds in 5 µl complete medium were added to cells. Cells were incubated at 33° C. and 5% $CO_2$ for 2 hrs after which they were washed twice with PBS and 45 µl of serum free medium was added. Compounds in serum free medium (5 µl) were added and cells were incubated at 37° C. and 5% CO2. After 24 hrs, 25 µl of PBS containing 15 µg/ml Hoechst 33342 and 12 µg/ml propidium iodide (PI) were added and cells were incubated for 30 min at room temperature on a rocker protected from light.

(3) 384-Well High Content Screening (HCS) and Analysis

Images were collected on the ImageXpress Ultra (IXU) sequentially acquiring Hoechst (Ch1, 405/447 nm) and Texas Red (Ch2, 561/685 nm) using a 10× Plan Fluor objective. Image analysis was carried out using the Multi-wavelength Cell Scoring application in the MetaXpress software. The nuclear compartment was identified in Ch1 with a threshold intensity of 2,000 above background and the Texas Red compartment was identified in Ch2 with a threshold intensity of 20,000 above background.

Heterogeneity analysis of the distribution of PI labeling in the STHdh$^{Q111}$ cell population was done using the heterogeneity indices. The combined assessment of the population diversity (quadratic entropy (QE), non-normality (Kolmogorov-Smirnov (KS) and percent outliers classified the control populations as having macro-heterogeneity, and review of the HistoBox plot indicated a bimodal distribution. Thus, all subsequent analysis of the images was performed at the cell level and population average measurements were not used.

For the analyses presented here the Percent Recovery was calculated from the Percent PI positive cells by:

$$\left\{1 - \frac{(\text{Percent } PI \text{ Positive cells for } Cpd) - (\text{Percent } PI \text{ Positive cells for Positive } Ctrl)}{(\text{Percent } PI \text{ Positive cells for Negative } Ctrl) - (\text{Percent } PI \text{ Positive cells for Positive } Ctrl)}\right\} \times 100 \quad (1)$$

where positive controls are the STHdh$^{Q7}$ cells, and negative controls are the STHdh$^{Q111}$ cells treated with DMSO (4) 384-Well LOPAC Library Screen The LOPAC library was screened in the 384-well PI assay at 30, 10, and 3 µM. Compounds that showed increased percent recovery at least 3 SD above the mean of the STHdh$^{Q111}$ DMSO control and were not toxic, having a total cell number that was not less than 3 SD below the total cell number of the STHdh$^{Q111}$ DMSO control, were picked for confirmation in a concentration response assay.

(5) cAMP Assay cAMP measurements were performed using the cAMP Enzyme Immunoassay kit (CA-200, Sigma-Aldrich, St Louis, Mo., USA), following the acetylated version of protocol supplied by the vendor. Cells were plated in 96-well plates at 9,000 cells per well and allowed to attach in complete medium at 33° C. and 5% $CO_2$ for 24 hr. Cells were treated with 10 µl DMSO or compounds and incubated in complete medium at 33° C. and 5% $CO_2$ for 15, 30, and 120 minutes at which time the medium was removed and the cells were lysed with 250 µl of 0.1N HCl for 20 minutes. Equivalent amounts of samples were used in the ELISA assay as determined by protein concentration. Protein concentrations were determined using the Bradford protein assay (Bio Rad).

(6) PKA Activation Assay

Cells were treated as described for testing in the 384-well PI assay. At 24 hr the cells were fixed with 3.7% formaldehyde in PBS with 4 µg/ml Hoechst 33342 and permeabilized with 95% MeOH. Plates were blocked with 3% BSA in PBS and were incubated with rabbit anti-PKA (αβγ catalytic subunit; EP2606Y; phospho-T197, abcam, Cambridge Mass.) mAb overnight at 4° C. Plates were wash three times with 1×PBS and incubated with Alexa-Fluor 488-conjugated Goat anti-Rabbit IgG (H+L) (Jackson ImmunoResearch, West Grove, Pa.) for 1 hr at room temperature, washed three times with 1×PBS, and imaged. Images were collected on the IXU sequentially acquiring Hoechst (Ch1, 405/447 nm) and Alexa 488 (Ch2, 488/514 nm) using a 20× (0.45-NA) ELWD objective. Image analysis was carried out using the Multiwavelength Translocation application in the MetaExpress software. The nuclear compartment was identified in Ch1 with a threshold intensity of 5,000 above background (the nuclear mask). The nuclear mask was eroded 1 µm to create the Inner region mask in Ch2. The nuclear pPKA in each cell was measured as the Mean Inner Intensity Ch2 of the Alexa 488 label within the Inner region mask in Ch2. The cytoplasmic pKA was measured in a 3 µM wide ring around the nuclear mask.

(7) 1536-Well PI Assay.

STHdh$^{Q111}$ or STHdh$^{Q7}$ mouse striatal cells were plated in black wall, clear bottom 1536-well cyclic olefin polymer-type imaging plates (Edition Eight; Whitefish, Mont.) at 1.2×103 cells per well in 5 µl volume using a Multidrop Combi Reagent Dispenser (ThermoFisher). Growth medium was DMEM (25 mM D-glucose; ThermoFisher) supplemented with 1% fetal bovine serum (Hyclone), 5 mM sodium pyruvate (ThermoFisher), and 0.3× penicillin/streptomycin (ThermoFisher). Cells were incubated for 16 h in a humidified incubator maintained at 33° C. and 5% $CO_2$. 46 nl of compounds (NCATS Pharmaceutical Collection or vehicle control; qHTS format; 5 concentrations spanning 30 nM-50 µM) were transferred using a Kalypsis pin tool and plates were returned to 33° C. for 2 h. Cells were moved to a humidified incubator maintained at 37° C. and 5% $CO_2$ for 24 h. Hoechst 33342 (ThermoFisher) and propidium iodide (PI, Sigma-Aldrich) were prepared in PBS and 1 µl was added to each well, yielding a final concentration of 4 µg/ml and 5 µg/ml, respectively. Plates were incubated at room temperature for 30 min prior to imaging.

(8) 1536-Well Imaging and Analysis

Plates were imaged on an IN Cell 2200 widefield automated microscope (GE Healthcare) using a 10× 0.45 NA air objective and standard DAPI (390/18×, 432/48m) and Cy3 (542/27×, 587/45m) filter sets, both at 30 milliseconds of exposure. One field of view per well, encompassing the entire well was chosen for imaging. Digital images were analyzed using IN Cell Analyzer Workstation Software v3.7.3 (GE Healthcare) with the Multi Target Analysis canned analysis protocol. Briefly, Hoechst nuclei were identified using top hat segmentation (objects with minimum area of 75 µm and a sensitivity setting of 87). All available data parameters were captured on a cell by cell basis for both nuclei and PI objects. A mean PI intensity of more than 3 STDEV above the background mean was classified as PI positive. Data were normalized to controls on a per-plate basis (Q7+vehicle and Q111+vehicle), with or percent recovery calculated as above (equation 1). Concentration-response curves were generated using NCATS software and active compounds had curve-class designations of 1.1, 1.2, 2.1, and 2.237.

(9) Drug Combination Analysis

For single concentration combination experiments, compounds were mixed together in pairs using concentrations that were at or near the plateau of the respective concentration curves for the individual compounds. Activity of the combinations was assessed in the 384-well assay described above. The Bliss combination index was calculated using the Bliss Independence Model:

$$\text{Bliss Combination Index} = RF12/((RF1+RF2) - (RF1*RF2)) \quad (2)$$

where RF12 is the percent recovery of the combination of compounds 1 and 2, RF1=the percent recovery of compound 1, and RF2 is the percent recovery of compound 2.

For selected compounds, the effect of compounds paired in a concentration response curve was assessed by mixing compounds at four concentrations each. Two concentrations used were on the respective plateaus of the single compounds, and two were on the slope before the plateau. The combination index was calculated using the method of Chou and Talalay and isobolograms were drawn in Spotfire (Tibco, Boston, Mass.). The Chou-Talalay Median-Effect model accounts for the dose response of drugs to determine the combination effect. The resultant equation for the model is as follows:

$$CI = \frac{D_1}{D_{x1}} + \frac{D_2}{D_{x2}} \quad (3)$$

where D1 and D2 denote the doses of compound 1 and compound 2 required to reach an effect of x % as single treatment, while Dx1 and Dx2 are the doses needed in combination to inhibit x %, respectively. Combinations were examined for induction of antagonism (CI>1.1), additivity (0.9<CI<1.1), synergy (CI<0.9) and strong synergy (CI<0.3).

(10) Computational Predictions of Drug-Target Binding 83 compounds were identified as potentially neuroprotective using a latent factor model (LFM) combined with structural similarity. The LFM approach, Balestra, is based on probabilistic factorization of the incomplete drug-target interaction matrix. Given a binary matrix, R, of interactions between N drugs and M targets, Balestra decomposes it into the product of two matrices, U and V, that express the drugs and targets in terms of D latent variables, $$R_{N \times M} = U_{N \times D}^T V_{D \times M}. \quad (4)$$

This decomposition assigns values—loosely comparable to interaction probabilities—to the previously undetermined elements of R. The LFM was trained on chemical-target interaction data from DrugBank (version 4.0.0, approved drug subset) and STITCH (version 3.0, experimental data only) databases. Identified from the same databases were all canonical targets of 15 hit compounds from an earlier mitochondrial screen 6 and 9 compounds that are in clinical trials for neuroprotection in HD. Compounds that the LFM predicted to have interaction values greater than 0.9 were selected as potentially neuroprotective. In addition to the LFM, the ROCS module in OpenEye software was used to predict neuroprotective compounds based on 3D structural similarity. A separate query was built based on the 3D shape and heavy atom properties of each of the 15 compounds from the mitochondrial screen. Each query was used to search compounds in DrugBank, and the top ranked compounds were selected based on the OpenEye ComboScore measure of shape and atom properties. The final set of predicted neuroprotective compounds was generated by merging the results from LFM prediction and 3D structural similarity search.

(11) Pathway Analysis

All canonical targets for the probes that showed cell protection were identified in DrugBank (version 4.5.0, approved drug subset) and STITCH ligand-protein interaction database (version 4.0, human subset with an experimental confidence score greater than 0.7), as well as data mining from the literature. These 23 probes were mapped to 78 targets and detailed drug-target interaction mapping was shown in detail in Table 1. Each target, and each probe by association, was then mapped to one or more pathways in the KEGG pathway database (*Homo sapiens*), ending up with 35 pathways as shown in Table 2. Also identified were all synergistic pairs of compounds in which the two compounds had different targets on the same pathway.

Over-representation of pathways among synergistic pairs in the screen is quantified using the enrichment factor $$EF_i = \frac{\frac{N_{pairs_i}}{N_{pairs}}}{\left(\frac{N_{compounds_i}}{N_{compounds}}\right)^2}, \quad (5)$$

where $N_{pairs_i}$ is the number of synergistic pairs mapped into pathway i, $N_{pairs}$=61 is the total number of synergistic pairs identified in the combination screen, $N_{compounds_i}$ is the number of compounds from DrugBank and STITCH that mapped into pathway i, and $N_{compounds}$ is the total number of compounds used from DrugBank and STITCH. The enrichment factor of a pathway is its propensity to be targeted by synergistic compound pairs in the screen.

2. Example 2: Rationale for New Combinations of Small Molecules Protecting Against Mutant HTT-Induced Cytotoxicity The initial identification of small molecule combinations was extended by screening a larger mechanistically diverse chemical library and analyzing for individual compounds that engender protection from mutant huntingtin (mHTT)-induced cytotoxicity and whose canonical protein targets have independently been associated with Huntington's Disease (HD)(Table 6). For example, the screen identified the fatty acid amide hydrolase (FAAH) inhibitor, SA 57, and the cannabinoid receptor 2 (CBR2) agonist, JWH-015, as two compounds demonstrating protection and having protein targets associated with HD. Inhibition of FAAH is known to increase endogenous cannabinoid levels and thus increase signaling through CBR2. Therefore, a combination of an FAAH inhibitor and a CBR2 agonist can demonstrate synergistic enhancement of cannabinoid signaling that in turn will protect cells expressing mHTT from stress-induced cytotoxicity.

TABLE 6

Combination Pairs

| Combination No. | Target 1 | Compound 1 | Compound 2 | Target 2 |
|---|---|---|---|---|
| 1 | CB2 agonists | JWH-015 | SA-57 | FAAH inhibitors |
| 2 | CB2 agonists | JWH-015 | SA-47 | FAAH inhibitors |
| 3 | CB2 agonists | JWH-133 | SA-57 | FAAH inhibitors |
| 4 | CB2 agonists | JWH-015 | JNJ 1661010 | FAAH inhibitors |
| 5 | CB2 agonists | JWH-133 | SA-47 | FAAH inhibitors |
| 6 | CB2 agonists | HU-308 | SA-57 | FAAH inhibitors |
| 7 | CB2 agonists | JWH-015 | URB-597 | FAAH inhibitors |
| 8 | CB2 agonists | JWH-133 | JNJ 1661010 | FAAH inhibitors |
| 9 | CB2 agonists | HU-308 | SA-47 | FAAH inhibitors |
| 10 | CB2 agonists | L-759,656 | SA-57 | FAAH inhibitors |

TABLE 6-continued

| Combination Pairs | | | | |
|---|---|---|---|---|
| Combination No. | Target 1 | Compound 1 | Compound 2 | Target 2 |
| 11 | CB2 agonists | JWH-015 | TAK 21d | FAAH inhibitors |
| 12 | CB2 agonists | JWH-133 | URB-597 | FAAH inhibitors |
| 13 | CB2 agonists | HU-308 | JNJ 1661010 | FAAH inhibitors |
| 14 | CB2 agonists | L-759,656 | SA-47 | FAAH inhibitors |
| 15 | ADORA2A agonists | CGS 21680 | SA-57 | FAAH inhibitors |
| 16 | CB2 agonists | JWH-015 | JZL 195 | FAAH inhibitors |
| 17 | CB2 agonists | JWH-133 | TAK 21d | FAAH inhibitors |
| 18 | CB2 agonists | HU-308 | URB-597 | FAAH inhibitors |
| 19 | CB2 agonists | L-759,656 | JNJ 1661010 | FAAH inhibitors |
| 20 | ADORA2A agonists | CGS 21680 | SA-47 | FAAH inhibitors |
| 21 | ADORA2A agonists | ATL 146e | SA-57 | FAAH inhibitors |
| 22 | CB2 agonists | JWH-015 | PF 750 | FAAH inhibitors |
| 23 | CB2 agonists | JWH-133 | JZL 195 | FAAH inhibitors |
| 24 | CB2 agonists | HU-308 | TAK 21d | FAAH inhibitors |
| 25 | CB2 agonists | L-759,656 | URB-597 | FAAH inhibitors |
| 26 | ADORA2A agonists | CGS 21680 | JNJ 1661010 | FAAH inhibitors |
| 27 | ADORA2A agonists | ATL 146e | SA-47 | FAAH inhibitors |
| 28 | ADORA2A agonists | ATL 313 | SA-57 | FAAH inhibitors |
| 29 | CB2 agonists | JWH-133 | PF 750 | FAAH inhibitors |
| 30 | CB2 agonists | HU-308 | JZL 195 | FAAH inhibitors |
| 31 | CB2 agonists | L-759,656 | TAK 21d | FAAH inhibitors |
| 32 | ADORA2A agonists | CGS 21680 | URB-597 | FAAH inhibitors |
| 33 | ADORA2A agonists | ATL 146e | JNJ 1661010 | FAAH inhibitors |
| 34 | ADORA2A agonists | ATL 313 | SA-47 | FAAH inhibitors |
| 35 | ADORA2A agonists | UK-432,097 | SA-57 | FAAH inhibitors |
| 36 | CB2 agonists | HU-308 | PF 750 | FAAH inhibitors |
| 37 | CB2 agonists | L-759,656 | JZL 195 | FAAH inhibitors |
| 38 | ADORA2A agonists | CGS 21680 | TAK 21d | FAAH inhibitors |
| 39 | ADORA2A agonists | ATL 146e | URB-597 | FAAH inhibitors |
| 40 | ADORA2A agonists | ATL 313 | JNJ 1661010 | FAAH inhibitors |
| 41 | ADORA2A agonists | UK-432,097 | SA-47 | FAAH inhibitors |
| 42 | PDE10a inhibitors | TC-E 5005 | SA-57 | FAAH inhibitors |
| 43 | CB2 agonists | L-759,656 | PF 750 | FAAH inhibitors |
| 44 | ADORA2A agonists | CGS 21680 | JZL 195 | FAAH inhibitors |
| 45 | ADORA2A agonists | ATL 146e | TAK 21d | FAAH inhibitors |
| 46 | ADORA2A agonists | ATL 313 | URB-597 | FAAH inhibitors |
| 47 | ADORA2A agonists | UK-432,097 | JNJ 1661010 | FAAH inhibitors |
| 48 | PDE10a inhibitors | TC-E 5005 | SA-47 | FAAH inhibitors |
| 49 | PDE10a inhibitors | PF-2545920 hydrochloride | SA-57 | FAAH inhibitors |
| 50 | ADORA2A agonists | CGS 21680 | PF 750 | FAAH inhibitors |
| 51 | ADORA2A agonists | ATL 146e | JZL 195 | FAAH inhibitors |
| 52 | ADORA2A agonists | ATL 313 | TAK 21d | FAAH inhibitors |
| 53 | ADORA2A agonists | UK-432,097 | URB-597 | FAAH inhibitors |
| 54 | PDE10a inhibitors | TC-E 5005 | JNJ 1661010 | FAAH inhibitors |
| 55 | PDE10a inhibitors | PF-2545920 hydrochloride | SA-47 | FAAH inhibitors |
| 56 | PDE10a inhibitors | TAK-063 | SA-57 | FAAH inhibitors |
| 57 | ADORA2A agonists | ATL 313 | JZL 195 | FAAH inhibitors |
| 58 | ADORA2A agonists | UK-432,097 | TAK 21d | FAAH inhibitors |
| 59 | PDE10a inhibitors | TC-E 5005 | URB-597 | FAAH inhibitors |
| 60 | PDE10a inhibitors | PF-2545920 hydrochloride | JNJ 1661010 | FAAH inhibitors |
| 61 | PDE10a inhibitors | TAK-063 | SA-47 | FAAH inhibitors |
| 62 | PDE10a inhibitors | AMG 579 | SA-57 | FAAH inhibitors |
| 63 | ADORA2A agonists | UK-432,097 | JZL 195 | FAAH inhibitors |
| 64 | PDE10a inhibitors | TC-E 5005 | TAK 21d | FAAH inhibitors |
| 65 | PDE10a inhibitors | PF-2545920 hydrochloride | URB-597 | FAAH inhibitors |
| 66 | PDE10a inhibitors | TAK-063 | JNJ 1661010 | FAAH inhibitors |
| 67 | PDE10a inhibitors | AMG 579 | SA-47 | FAAH inhibitors |
| 68 | DRD2 antagonists | L-741,626 | SA-57 | FAAH inhibitors |
| 69 | PDE10a inhibitors | TC-E 5005 | JZL 195 | FAAH inhibitors |
| 70 | PDE10a inhibitors | PF-2545920 hydrochloride | TAK 21d | FAAH inhibitors |
| 71 | PDE10a inhibitors | TAK-063 | URB-597 | FAAH inhibitors |
| 72 | PDE10a inhibitors | AMG 579 | JNJ 1661010 | FAAH inhibitors |
| 73 | DRD2 antagonists | L-741,626 | SA-47 | FAAH inhibitors |
| 74 | DRD2 antagonists | Remoxipride | SA-57 | FAAH inhibitors |
| 75 | PDE10a inhibitors | PF-2545920 hydrochloride | JZL 195 | FAAH inhibitors |
| 76 | PDE10a inhibitors | TAK-063 | TAK 21d | FAAH inhibitors |
| 77 | PDE10a inhibitors | AMG 579 | URB-597 | FAAH inhibitors |
| 78 | DRD2 antagonists | L-741,626 | JNJ 1661010 | FAAH inhibitors |
| 79 | DRD2 antagonists | Remoxipride | SA-47 | FAAH inhibitors |
| 80 | DRD2 antagonists | Raclopride | SA-57 | FAAH inhibitors |

TABLE 6-continued

Combination Pairs

| Combination No. | Target 1 | Compound 1 | Compound 2 | Target 2 |
|---|---|---|---|---|
| 81 | PDE10a inhibitors | TAK-063 | JZL 195 | FAAH inhibitors |
| 82 | PDE10a inhibitors | AMG 579 | TAK 21d | FAAH inhibitors |
| 83 | DRD2 antagonists | L-741,626 | URB-597 | FAAH inhibitors |
| 84 | DRD2 antagonists | Remoxipride | JNJ 1661010 | FAAH inhibitors |
| 85 | DRD2 antagonists | Raclopride | SA-47 | FAAH inhibitors |
| 86 | DRD2 antagonists | Nemonapride | SA-57 | FAAH inhibitors |
| 87 | PDE10a inhibitors | AMG 579 | JZL 195 | FAAH inhibitors |
| 88 | DRD2 antagonists | L-741,626 | TAK 21d | FAAH inhibitors |
| 89 | DRD2 antagonists | Remoxipride | URB-597 | FAAH inhibitors |
| 90 | DRD2 antagonists | Raclopride | JNJ 1661010 | FAAH inhibitors |
| 91 | DRD2 antagonists | Nemonapride | SA-47 | FAAH inhibitors |
| 92 | GR selective modulators | Fluticasone | SA-57 | FAAH inhibitors |
| 93 | DRD2 antagonists | L-741,626 | JZL 195 | FAAH inhibitors |
| 94 | DRD2 antagonists | Remoxipride | TAK 21d | FAAH inhibitors |
| 95 | DRD2 antagonists | Raclopride | URB-597 | FAAH inhibitors |
| 96 | DRD2 antagonists | Nemonapride | JNJ 1661010 | FAAH inhibitors |
| 97 | GR selective modulators | Fluticasone | SA-47 | FAAH inhibitors |
| 98 | GR selective modulators | AZD 9567 | SA-57 | FAAH inhibitors |
| 99 | DRD2 antagonists | Remoxipride | JZL 195 | FAAH inhibitors |
| 100 | DRD2 antagonists | Raclopride | TAK 21d | FAAH inhibitors |
| 101 | DRD2 antagonists | Nemonapride | URB-597 | FAAH inhibitors |
| 102 | GR selective modulators | Fluticasone | JNJ 1661010 | FAAH inhibitors |
| 103 | GR selective modulators | AZD 9567 | SA-47 | FAAH inhibitors |
| 104 | GR selective modulators | AL-438 | SA-57 | FAAH inhibitors |
| 105 | DRD2 antagonists | Raclopride | JZL 195 | FAAH inhibitors |
| 106 | DRD2 antagonists | Nemonapride | TAK 21d | FAAH inhibitors |
| 107 | GR selective modulators | Fluticasone | URB-597 | FAAH inhibitors |
| 108 | GR selective modulators | AZD 9567 | JNJ 1661010 | FAAH inhibitors |
| 109 | GR selective modulators | AL-438 | SA-47 | FAAH inhibitors |
| 110 | GR selective modulators | Mapracorat | SA-57 | FAAH inhibitors |
| 111 | DRD2 antagonists | Nemonapride | JZL 195 | FAAH inhibitors |
| 112 | GR selective modulators | Fluticasone | TAK 21d | FAAH inhibitors |
| 113 | GR selective modulators | AZD 9567 | URB-597 | FAAH inhibitors |
| 114 | GR selective modulators | AL-438 | JNJ 1661010 | FAAH inhibitors |
| 115 | GR selective modulators | Mapracorat | SA-47 | FAAH inhibitors |
| 116 | GR selective modulators | LGD-5552 | SA-57 | FAAH inhibitors |
| 117 | GR selective modulators | Fluticasone | JZL 195 | FAAH inhibitors |
| 118 | GR selective modulators | AZD 9567 | TAK 21d | FAAH inhibitors |
| 119 | GR selective modulators | AL-438 | URB-597 | FAAH inhibitors |
| 120 | GR selective modulators | Mapracorat | JNJ 1661010 | FAAH inhibitors |
| 121 | GR selective modulators | LGD-5552 | SA-47 | FAAH inhibitors |
| 122 | GR selective modulators | AZD 9567 | JZL 195 | FAAH inhibitors |
| 123 | GR selective modulators | AL-438 | TAK 21d | FAAH inhibitors |
| 124 | GR selective modulators | Mapracorat | URB-597 | FAAH inhibitors |
| 125 | GR selective modulators | LGD-5552 | JNJ 1661010 | FAAH inhibitors |
| 126 | GR selective modulators | AZD 9567 | PF 750 | FAAH inhibitors |
| 127 | GR selective modulators | AL-438 | JZL 195 | FAAH inhibitors |
| 128 | GR selective modulators | Mapracorat | TAK 21d | FAAH inhibitors |
| 129 | GR selective modulators | LGD-5552 | URB-597 | FAAH inhibitors |
| 130 | GR selective modulators | AL-438 | PF 750 | FAAH inhibitors |
| 131 | GR selective modulators | AZD 9567 | JWH-015 | CB2 agonists |
| 132 | GR selective modulators | LGD-5552 | TAK 21d | FAAH inhibitors |
| 133 | GR selective modulators | Mapracorat | PF 750 | FAAH inhibitors |
| 134 | GR selective modulators | AL-438 | JWH-015 | CB2 agonists |
| 135 | GR selective modulators | LGD-5552 | PF 750 | FAAH inhibitors |
| 136 | GR selective modulators | Mapracorat | JWH-015 | CB2 agonists |
| 137 | GR selective modulators | AL-438 | JWH-133 | CB2 agonists |
| 138 | GR selective modulators | AZD 9567 | HU-308 | CB2 agonists |
| 139 | GR selective modulators | LGD-5552 | JWH-015 | CB2 agonists |
| 140 | GR selective modulators | Mapracorat | JWH-133 | CB2 agonists |
| 141 | GR selective modulators | AL-438 | HU-308 | CB2 agonists |
| 142 | GR selective modulators | AZD 9567 | L-759,656 | CB2 agonists |
| 143 | GR selective modulators | LGD-5552 | JWH-133 | CB2 agonists |
| 144 | GR selective modulators | Mapracorat | HU-308 | CB2 agonists |
| 145 | GR selective modulators | AL-438 | L-759,656 | CB2 agonists |
| 146 | GR selective modulators | AZD 9567 | CGS 21680 | ADORA2A agonists |
| 147 | GR selective modulators | LGD-5552 | HU-308 | CB2 agonists |
| 148 | GR selective modulators | Mapracorat | L-759,656 | CB2 agonists |
| 149 | GR selective modulators | AL-438 | CGS 21680 | ADORA2A agonists |
| 150 | GR selective modulators | AZD 9567 | ATL 146e | ADORA2A agonists |
| 151 | GR selective modulators | LGD-5552 | L-759,656 | CB2 agonists |
| 152 | GR selective modulators | Mapracorat | CGS 21680 | ADORA2A agonists |
| 153 | GR selective modulators | AL-438 | ATL 146e | ADORA2A agonists |
| 154 | GR selective modulators | AZD 9567 | ATL 313 | ADORA2A agonists |
| 155 | GR selective modulators | LGD-5552 | CGS 21680 | ADORA2A agonists |
| 156 | GR selective modulators | Mapracorat | ATL 146e | ADORA2A agonists |

TABLE 6-continued

Combination Pairs

| Combination No. | Target 1 | Compound 1 | Compound 2 | Target 2 |
|---|---|---|---|---|
| 157 | GR selective modulators | AL-438 | ATL 313 | ADORA2A agonists |
| 158 | GR selective modulators | AZD 9567 | UK-432,097 | ADORA2A agonists |
| 159 | GR selective modulators | LGD-5552 | ATL 146e | ADORA2A agonists |
| 160 | GR selective modulators | Mapracorat | ATL 313 | ADORA2A agonists |
| 161 | GR selective modulators | AL-438 | UK-432,097 | ADORA2A agonists |
| 162 | GR selective modulators | AZD 9567 | TC-E 5005 | PDE10a inhibitors |
| 163 | GR selective modulators | LGD-5552 | ATL 313 | ADORA2A agonists |
| 164 | GR selective modulators | Mapracorat | UK-432,097 | ADORA2A agonists |
| 165 | GR selective modulators | AL-438 | TC-E 5005 | PDE10a inhibitors |
| 166 | GR selective modulators | AZD 9567 | PF-2545920 hydrochloride | PDE10a inhibitors |
| 167 | GR selective modulators | LGD-5552 | UK-432,097 | ADORA2A agonists |
| 168 | GR selective modulators | Mapracorat | TC-E 5005 | PDE10a inhibitors |
| 169 | GR selective modulators | AL-438 | PF-2545920 hydrochloride | PDE10a inhibitors |
| 170 | GR selective modulators | AZD 9567 | TAK-063 | PDE10a inhibitors |
| 171 | GR selective modulators | Fluticasone | AMG 579 | PDE10a inhibitors |
| 172 | GR selective modulators | LGD-5552 | TC-E 5005 | PDE10a inhibitors |
| 173 | GR selective modulators | Mapracorat | PF-2545920 hydrochloride | PDE10a inhibitors |
| 174 | GR selective modulators | AL-438 | TAK-063 | PDE10a inhibitors |
| 175 | GR selective modulators | AZD 9567 | AMG 579 | PDE10a inhibitors |
| 176 | GR selective modulators | Fluticasone | L-741,626 | DRD2 antagonists |
| 177 | GR selective modulators | LGD-5552 | PF-2545920 hydrochloride | PDE10a inhibitors |
| 178 | GR selective modulators | Mapracorat | TAK-063 | PDE10a inhibitors |
| 179 | GR selective modulators | AL-438 | AMG 579 | PDE10a inhibitors |
| 180 | GR selective modulators | AZD 9567 | L-741,626 | DRD2 antagonists |
| 181 | GR selective modulators | Fluticasone | Remoxipride | DRD2 antagonists |
| 182 | GR selective modulators | LGD-5552 | TAK-063 | PDE10a inhibitors |
| 183 | GR selective modulators | Mapracorat | AMG 579 | PDE10a inhibitors |
| 184 | GR selective modulators | AL-438 | L-741,626 | DRD2 antagonists |
| 185 | GR selective modulators | AZD 9567 | Remoxipride | DRD2 antagonists |
| 186 | GR selective modulators | Fluticasone | Raclopride | DRD2 antagonists |
| 187 | GR selective modulators | LGD-5552 | AMG 579 | PDE10a inhibitors |
| 188 | GR selective modulators | Mapracorat | L-741,626 | DRD2 antagonists |
| 189 | GR selective modulators | AL-438 | Remoxipride | DRD2 antagonists |
| 190 | GR selective modulators | AZD 9567 | Raclopride | DRD2 antagonists |
| 191 | GR selective modulators | Fluticasone | Nemonapride | DRD2 antagonists |
| 192 | GR selective modulators | LGD-5552 | L-741,626 | DRD2 antagonists |
| 193 | GR selective modulators | Mapracorat | Remoxipride | DRD2 antagonists |
| 194 | GR selective modulators | AL-438 | Raclopride | DRD2 antagonists |
| 195 | GR selective modulators | AZD 9567 | Nemonapride | DRD2 antagonists |
| 196 | GR selective modulators | LGD-5552 | Remoxipride | DRD2 antagonists |
| 197 | GR selective modulators | Mapracorat | Raclopride | DRD2 antagonists |
| 198 | GR selective modulators | AL-438 | Nemonapride | DRD2 antagonists |
| 199 | GR selective modulators | LGD-5552 | Raclopride | DRD2 antagonists |
| 200 | GR selective modulators | Mapracorat | Nemonapride | DRD2 antagonists |
| 201 | GR selective modulators | LGD-5552 | Nemonapride | DRD2 antagonists |
| 202 | ADORA2A agonists | ATL 146e | PF 750 | FAAH inhibitors |
| 203 | ADORA2A agonists | CGS 21680 | JWH-015 | CB2 agonists |
| 204 | GR selective modulators | LGD-5552 | JZL 195 | FAAH inhibitors |
| 205 | GR selective modulators | AZD 9567 | JWH-133 | CB2 agonists |
| 206 | GR selective modulators | Fluticasone | TAK-063 | PDE10a inhibitors |
| 207 | DRD2 antagonists | Nemonapride | AMG 579 | PDE10a inhibitors |
| 208 | ADORA2A agonists | ATL 313 | PF 750 | FAAH inhibitors |
| 209 | ADORA2A agonists | ATL 146e | JWH-015 | CB2 agonists |
| 210 | ADORA2A agonists | CGS 21680 | JWH-133 | CB2 agonists |
| 211 | GR selective modulators | Fluticasone | PF-2545920 hydrochloride | PDE10a inhibitors |
| 212 | DRD2 antagonists | Nemonapride | TAK-063 | PDE10a inhibitors |
| 213 | DRD2 antagonists | Raclopride | AMG 579 | PDE10a inhibitors |
| 214 | ADORA2A agonists | UK-432,097 | PF 750 | FAAH inhibitors |
| 215 | ADORA2A agonists | ATL 313 | JWH-015 | CB2 agonists |
| 216 | ADORA2A agonists | ATL 146e | JWH-133 | CB2 agonists |
| 217 | ADORA2A agonists | CGS 21680 | HU-308 | CB2 agonists |
| 218 | GR selective modulators | Fluticasone | TC-E 5005 | PDE10a inhibitors |
| 219 | DRD2 antagonists | Nemonapride | PF-2545920 hydrochloride | PDE10a inhibitors |
| 220 | DRD2 antagonists | Raclopride | TAK-063 | PDE10a inhibitors |
| 221 | DRD2 antagonists | Remoxipride | AMG 579 | PDE10a inhibitors |
| 222 | PDE10a inhibitors | TC-E 5005 | PF 750 | FAAH inhibitors |
| 223 | ADORA2A agonists | UK-432,097 | JWH-015 | CB2 agonists |
| 224 | ADORA2A agonists | ATL 313 | JWH-133 | CB2 agonists |
| 225 | ADORA2A agonists | ATL 146e | HU-308 | CB2 agonists |
| 226 | ADORA2A agonists | CGS 21680 | L-759,656 | CB2 agonists |

TABLE 6-continued

| | Combination Pairs | | | |
|---|---|---|---|---|
| Combination No. | Target 1 | Compound 1 | Compound 2 | Target 2 |
| 227 | PDE10a inhibitors | PF-2545920 hydrochloride | PF 750 | FAAH inhibitors |
| 228 | PDE10a inhibitors | TC-E 5005 | JWH-015 | CB2 agonists |
| 229 | ADORA2A agonists | UK-432,097 | JWH-133 | CB2 agonists |
| 230 | ADORA2A agonists | ATL 313 | HU-308 | CB2 agonists |
| 231 | ADORA2A agonists | ATL 146e | L-759,656 | CB2 agonists |
| 232 | PDE10a inhibitors | TAK-063 | PF 750 | FAAH inhibitors |
| 233 | PDE10a inhibitors | PF-2545920 hydrochloride | JWH-015 | CB2 agonists |
| 234 | PDE10a inhibitors | TC-E 5005 | JWH-133 | CB2 agonists |
| 235 | ADORA2A agonists | UK-432,097 | HU-308 | CB2 agonists |
| 236 | ADORA2A agonists | ATL 313 | L-759,656 | CB2 agonists |
| 237 | PDE10a inhibitors | AMG 579 | PF 750 | FAAH inhibitors |
| 238 | PDE10a inhibitors | TAK-063 | JWH-015 | CB2 agonists |
| 239 | PDE10a inhibitors | PF-2545920 hydrochloride | JWH-133 | CB2 agonists |
| 240 | PDE10a inhibitors | TC-E 5005 | HU-308 | CB2 agonists |
| 241 | ADORA2A agonists | UK-432,097 | L-759,656 | CB2 agonists |
| 242 | DRD2 antagonists | L-741,626 | PF 750 | FAAH inhibitors |
| 243 | PDE10a inhibitors | AMG 579 | JWH-015 | CB2 agonists |
| 244 | PDE10a inhibitors | TAK-063 | JWH-133 | CB2 agonists |
| 245 | PDE10a inhibitors | PF-2545920 hydrochloride | HU-308 | CB2 agonists |
| 246 | PDE10a inhibitors | TC-E 5005 | L-759,656 | CB2 agonists |
| 247 | GR selective modulators | Fluticasone | L-759,656 | CB2 agonists |
| 248 | DRD2 antagonists | Nemonapride | CGS 21680 | ADORA2A agonists |
| 249 | DRD2 antagonists | Raclopride | ATL 146e | ADORA2A agonists |
| 250 | DRD2 antagonists | Remoxipride | ATL 313 | ADORA2A agonists |
| 251 | DRD2 antagonists | L-741,626 | UK-432,097 | ADORA2A agonists |
| 252 | GR selective modulators | Fluticasone | CGS 21680 | ADORA2A agonists |
| 253 | DRD2 antagonists | Nemonapride | ATL 146e | ADORA2A agonists |
| 254 | DRD2 antagonists | Raclopride | ATL 313 | ADORA2A agonists |
| 255 | DRD2 antagonists | Remoxipride | UK-432,097 | ADORA2A agonists |
| 256 | DRD2 antagonists | L-741,626 | TC-E 5005 | PDE10a inhibitors |
| 257 | GR selective modulators | Fluticasone | ATL 146e | ADORA2A agonists |
| 258 | DRD2 antagonists | Nemonapride | ATL 313 | ADORA2A agonists |
| 259 | DRD2 antagonists | Raclopride | UK-432,097 | ADORA2A agonists |
| 260 | DRD2 antagonists | Remoxipride | TC-E 5005 | PDE10a inhibitors |
| 261 | DRD2 antagonists | L-741,626 | PF-2545920 hydrochloride | PDE10a inhibitors |
| 262 | GR selective modulators | Fluticasone | ATL 313 | ADORA2A agonists |
| 263 | DRD2 antagonists | Nemonapride | UK-432,097 | ADORA2A agonists |
| 264 | DRD2 antagonists | Raclopride | TC-E 5005 | PDE10a inhibitors |
| 265 | DRD2 antagonists | Remoxipride | PF-2545920 hydrochloride | PDE10a inhibitors |
| 266 | DRD2 antagonists | L-741,626 | TAK-063 | PDE10a inhibitors |
| 267 | GR selective modulators | Fluticasone | UK-432,097 | ADORA2A agonists |
| 268 | DRD2 antagonists | Nemonapride | TC-E 5005 | PDE10a inhibitors |
| 269 | DRD2 antagonists | Raclopride | PF-2545920 hydrochloride | PDE10a inhibitors |
| 270 | DRD2 antagonists | Remoxipride | TAK-063 | PDE10a inhibitors |
| 271 | DRD2 antagonists | L-741,626 | AMG 579 | PDE10a inhibitors |
| 272 | DRD2 antagonists | Remoxipride | PF 750 | FAAH inhibitors |
| 273 | DRD2 antagonists | L-741,626 | JWH-015 | CB2 agonists |
| 274 | PDE10a inhibitors | AMG 579 | JWH-133 | CB2 agonists |
| 275 | PDE10a inhibitors | TAK-063 | HU-308 | CB2 agonists |
| 276 | PDE10a inhibitors | PF-2545920 hydrochloride | L-759,656 | CB2 agonists |
| 277 | PDE10a inhibitors | TC-E 5005 | CGS 21680 | ADORA2A agonists |
| 278 | GR selective modulators | Fluticasone | HU-308 | CB2 agonists |
| 279 | DRD2 antagonists | Nemonapride | L-759,656 | CB2 agonists |
| 280 | DRD2 antagonists | Raclopride | CGS 21680 | ADORA2A agonists |
| 281 | DRD2 antagonists | Remoxipride | ATL 146e | ADORA2A agonists |
| 282 | DRD2 antagonists | L-741,626 | ATL 313 | ADORA2A agonists |
| 283 | PDE10a inhibitors | AMG 579 | UK-432,097 | ADORA2A agonists |
| 284 | DRD2 antagonists | Raclopride | PF 750 | FAAH inhibitors |
| 285 | DRD2 antagonists | Remoxipride | JWH-015 | CB2 agonists |
| 286 | DRD2 antagonists | L-741,626 | JWH-133 | CB2 agonists |
| 287 | PDE10a inhibitors | AMG 579 | HU-308 | CB2 agonists |
| 288 | PDE10a inhibitors | TAK-063 | L-759,656 | CB2 agonists |
| 289 | PDE10a inhibitors | PF-2545920 hydrochloride | CGS 21680 | ADORA2A agonists |
| 290 | PDE10a inhibitors | TC-E 5005 | ATL 146e | ADORA2A agonists |
| 291 | DRD2 antagonists | Nemonapride | PF 750 | FAAH inhibitors |
| 292 | DRD2 antagonists | Raclopride | JWH-015 | CB2 agonists |
| 293 | DRD2 antagonists | Remoxipride | JWH-133 | CB2 agonists |

TABLE 6-continued

Combination Pairs

| Combination No. | Target 1 | Compound 1 | Compound 2 | Target 2 |
|---|---|---|---|---|
| 294 | DRD2 antagonists | L-741,626 | HU-308 | CB2 agonists |
| 295 | PDE10a inhibitors | AMG 579 | L-759,656 | CB2 agonists |
| 296 | PDE10a inhibitors | TAK-063 | CGS 21680 | ADORA2A agonists |
| 297 | PDE10a inhibitors | PF-2545920 hydrochloride | ATL 146e | ADORA2A agonists |
| 298 | PDE10a inhibitors | TC-E 5005 | ATL 313 | ADORA2A agonists |
| 299 | GR selective modulators | Fluticasone | JWH-015 | CB2 agonists |
| 300 | DRD2 antagonists | Nemonapride | JWH-133 | CB2 agonists |
| 301 | DRD2 antagonists | Raclopride | HU-308 | CB2 agonists |
| 302 | DRD2 antagonists | Remoxipride | L-759,656 | CB2 agonists |
| 303 | DRD2 antagonists | L-741,626 | CGS 21680 | ADORA2A agonists |
| 304 | PDE10a inhibitors | AMG 579 | ATL 146e | ADORA2A agonists |
| 305 | PDE10a inhibitors | TAK-063 | ATL 313 | ADORA2A agonists |
| 306 | PDE10a inhibitors | PF-2545920 hydrochloride | UK-432,097 | ADORA2A agonists |
| 307 | GR selective modulators | Mapracorat | JZL 195 | FAAH inhibitors |
| 308 | GR selective modulators | Fluticasone | JWH-133 | CB2 agonists |
| 309 | DRD2 antagonists | Nemonapride | HU-308 | CB2 agonists |
| 310 | DRD2 antagonists | Raclopride | L-759,656 | CB2 agonists |
| 311 | DRD2 antagonists | Remoxipride | CGS 21680 | ADORA2A agonists |
| 312 | DRD2 antagonists | L-741,626 | ATL 146e | ADORA2A agonists |
| 313 | PDE10a inhibitors | AMG 579 | ATL 313 | ADORA2A agonists |
| 314 | PDE10a inhibitors | TAK-063 | UK-432,097 | ADORA2A agonists |
| 315 | GR selective modulators | Fluticasone | PF 750 | FAAH inhibitors |
| 316 | DRD2 antagonists | Nemonapride | JWH-015 | CB2 agonists |
| 317 | DRD2 antagonists | Raclopride | JWH-133 | CB2 agonists |
| 318 | DRD2 antagonists | Remoxipride | HU-308 | CB2 agonists |
| 319 | DRD2 antagonists | L-741,626 | L-759,656 | CB2 agonists |
| 320 | PDE10a inhibitors | AMG 579 | CGS 21680 | ADORA2A agonists |
| 321 | PDE10a inhibitors | TAK-063 | ATL 146e | ADORA2A agonists |
| 322 | PDE10a inhibitors | PF-2545920 hydrochloride | ATL 313 | ADORA2A agonists |
| 323 | PDE10a inhibitors | TC-E 5005 | UK-432,097 | ADORA2A agonists |

The screen also identified several G-protein coupled receptor (GPCR) ligands demonstrating protection and whose targets have been independently associated with HD. These GPCRs include CBR2, DRD2, and ADORA2A. Interestingly, these GPCRs are known to form heterodimers and heterotrimers selectively in the brain and GPCR associated sorting proteins (GASP) such as GASP 2 have been shown to directly interact with mHTT. Therefore we hypothesize that GPCR ligands that individually show partial protection will demonstrate enhanced protection in combination. Furthermore, since cAMP is a major second messenger of these GPCRs and since it has been shown herein that protection involves elevation to normal levels of cAMP-activated PKA kinase activity, a phosphodiesterase 10a inhibitor that increase cAMP levels (for example increasing cAMP levels 10-fold), 2) show partial protection in the screen, and 3) has been independently associated with HD can be effective in combination with individual GPCR ligands that also demonstrate partial protection.

Since the glucocorticoid receptor has been implicated in HD and since it has been demonstrated herein that glucocorticoid receptor (GR) agonists demonstrate protection, steroidal and particularly non-steroidal selective GR modulators (devoid of unwanted steroid-mediated side effects) can be effective in combinations with other classes of small molecules showing partial protection. The basis for synergy can result from the established crosstalk between GR and GPCRs.

D. REFERENCES

Allen, M. D. & Zhang, J. Subcellular dynamics of protein kinase A activity visualized by FRET-based reporters. *Biochemical and biophysical research communications* 348, 716-721, doi:10.1016/j.bbrc.2006.07.136 (2006).

Barone, J. A. Domperidone: a peripherally acting dopamine2-receptor antagonist. *The Annals of pharmacotherapy* 33, 429-440 (1999).

Bliss, C. The toxicity of poisons applied jointly. *Ann Appl Biol* 26, 585-615 (1939).

Chakravarti, A., Clark, A. G. & Mootha, V. K. Distilling Pathophysiology from Complex Disease Genetics. *Cell* 155, 21-26, doi:10.1016/j.cell.2013.09.001 (2013).

ChEMBL—Benztropine, (2016).

ChEMBL—Isoetarine, (2016).

Chen, M. et al. Minocycline inhibits caspase-1 and caspase-3 expression and delays mortality in a transgenic mouse model of Huntington disease. *Nature medicine* 6, 797-801, doi:10.1038/77528 (2000).

Chou, T. C. & Talalay, P. Generalized equations for the analysis of inhibitions of Michaelis-Menten and higher-order kinetic systems with two or more mutually exclusive and nonexclusive inhibitors. *European journal of biochemistry/FEBS* 115, 207-216 (1981).

Chou, T. C. & Talalay, P. Quantitative analysis of dose-effect relationships: the combined effects of multiple drugs or enzyme inhibitors. *Advances in enzyme regulation* 22, 27-55 (1984).

Clabough, E. B. Huntington's disease: the past, present, and future search for disease modifiers. *Yale J Biol Med* 86, 217-233 (2013).

Cobanoglu, M. C., Liu, C., Hu, F., Oltvai, Z. N. & Bahar, I. Predicting drug-target interactions using probabilistic matrix factorization. *Journal of chemical information and modeling* 53, 3399-3409, doi:10.1021/ci400219z (2013).

Cobanoglu, M. C., Oltvai, Z. N., Taylor, D. L. & Bahar, I. BalestraWeb: efficient online evaluation of drug-target interactions. *Bioinformatics* 31, 131-133, doi:DOI 10.1093/bioinformatics/btu599 (2015).

DiPilato, L. M., Cheng, X. & Zhang, J. Fluorescent indicators of cAMP and Epac activation reveal differential dynamics of cAMP signaling within discrete subcellular compartments. *Proceedings of the National Academy of Sciences of the United States of America* 101, 16513-16518, doi:10.1073/pnas.0405973101 (2004).

Gough, A. et al. Biologically Relevant Heterogeneity: Metrics and Practical Insights. *J. Biomol Screen* In Press (2016).

Gough, A. H. et al. Identifying and quantifying heterogeneity in high content analysis: application of heterogeneity indices to drug discovery. *PLoS One* 9, e102678, doi:10.1371/journal.pone.0102678 (2014).

Gough, A., Shun, T. Y., Taylor, D. L. & Schurdak, M. A metric and workflow for quality control in the analysis of heterogeneity in phenotypic profiles and screens. *Methods* 96, 12-26, doi:10.1016/j.ymeth.2015.10.007 (2016).

Greco, W. R., Bravo, G. & Parsons, J. C. The search for synergy: a critical review from a response surface perspective. *Pharmacological reviews* 47, 331-385 (1995).

Hawkins, P. C., Skillman, A. G. & Nicholls, A. Comparison of shape-matching and docking as virtual screening tools. *Journal of medicinal chemistry* 50, 74-82 (2007).

Huang, R. et al. The NCGC pharmaceutical collection: a comprehensive resource of clinically approved drugs enabling repurposing and chemical genomics. *Sci Transl Med* 3, 80ps16, doi:10.1126/scitranslmed.3001862 (2011).

Inglese, J. et al. Quantitative high-throughput screening: a titration-based approach that efficiently identifies biological activities in large chemical libraries. *Proceedings of the National Academy of Sciences of the United States of America* 103, 11473-11478, doi:10.1073/pnas.0604348103 (2006).

Kell, D. B., Dobson, P. D., Bilsland, E. & Oliver, S. G. The promiscuous binding of pharmaceutical drugs and their transporter-mediated uptake into cells: what we (need to) know and how we can do so. *Drug discovery today* 18, 218-239, doi:10.1016/j.drudis.2012.11.008 (2013).

Kroemer, G. et al. Classification of cell death: recommendations of the Nomenclature Committee on Cell Death 2009. *Cell death and differentiation* 16, 3-11, doi:10.1038/cdd.2008.150 (2009).

Lin, J. T. et al. Regulation of feedback between protein kinase A and the proteasome system worsens Hunting-ton's disease. *Molecular and cellular biology* 33, 1073-1084, doi:10.1128/MCB.01434-12 (2013).

Lu, B. et al. Identification of NUB1 as a suppressor of mutant Huntington toxicity via enhanced protein clearance. *Nature neuroscience* 16, 562-570, doi:10.1038/nn.3367 (2013).

Martz, C. A. et al. Systematic identification of signaling pathways with potential to confer anticancer drug resistance. *Sci Signal* 7, ra121, doi:10.1126/scisignal.aaa1877 (2014).

Morris, D. I., Robbins, J. D., Ruoho, A. E., Sutkowski, E. M. & Seamon, K. B. Forskolin photoaffinity labels with specificity for adenylyl cyclase and the glucose transporter. *The Journal of biological chemistry* 266, 13377-13384 (1991).

Myeku, N. et al. Tau-driven 26S proteasome impairment and cognitive dysfunction can be prevented early in disease by activating cAMP-PKA signaling. *Nat Med* 22, 46-53, doi:10.1038/nm.4011 (2016).

Ona, V. O. et al. Inhibition of caspase-1 slows disease progression in a mouse model of Huntington's disease. *Nature* 399, 263-267 (1999).

Pamies, D. et al. A human brain microphysiological system derived from induced pluripotent stem cells to study neurological diseases and toxicity. *Altex*, doi:10.14573/altex.1609122 (2016).

Poch, G. & Kukovetz, W. R. Papaverine-induced inhibition of phosphodiesterase activity in various mammalian tissues. *Life sciences. Pt. 1: Physiology and pharmacology* 10, 133-144 (1971).

Rosen, D. S. et al. Pesticidal Cyanine Dye Derivatives. (2003).

Sample, V. et al. Regulation of nuclear PKA revealed by spatiotemporal manipulation of cyclic AMP. *Nat Chem Biol* 8, 375-382, doi:10.1038/nchembio.799 (2012).

Stern, A. M., Schurdak, M. E., Bahar, I., Berg, J. M. & Taylor, D. L. A Perspective on Implementing a Quantitative Systems Pharmacology Platform for Drug Discovery and the Advancement of Personalized Medicine. *J Biomol Screen* 21, 521-534, doi:10.1177/1087057116635818 (2016).

Supuran, C. T., Scozzafava, A. & Casini, A. Carbonic anhydrase inhibitors. *Medicinal research reviews* 23, 146-189, doi:10.1002/med.10025 (2003).

Trettel, F. Dominant phenotypes produced by the HD mutation in STHdh$^{Q111}$ striatal cells. *Human molecular genetics* 9, 2799-2809, doi:10.1093/hmg/9.19.2799 (2000).

Tsvetkov, A. S. et al. Proteostasis of polyglutamine varies among neurons and predicts neurodegeneration. *Nature Chemical Biology* 9, 586-592, doi:10.1038/nchembio.1308 (2013).

Wagner, B. K. & Schreiber, S. L. The Power of Sophisticated Phenotypic Screening and Modern Mechanism-of-Action Methods. *Cell chemical biology* 23, 3-9, doi:10.1016/j.chembiol.2015.11.008 (2016).

Wang, X. et al. Inhibitors of Cytochrome c Release with Therapeutic Potential for Huntington's Disease. *Journal of Neuroscience* 28, 9473-9485, doi:10.1523/jneurosci.1867-08.2008 (2008).

Wang, X. et al. Minocycline inhibits caspase-independent and -dependent mitochondrial cell death pathways in models of Huntington's disease. *Proceedings of the National Academy of Sciences* 100, 10483-10487, doi:10.1073/pnas.1832501100 (2003).

Yano, H. et al. Inhibition of mitochondrial protein import by mutant huntingtin. *Nature neuroscience* 17, 822-831, doi:10.1038/nn.3721 (2014).

Zhao, W. et al. A New Bliss Independence Model to Analyze Drug Combination Data. *J Biomol Screen* 19, 817-821, doi:10.1177/1087057114521867 (2014).

Zuccato, C., Valenza, M. & Cattaneo, E. Molecular mechanisms and potential therapeutical targets in Huntington's disease. *Physiological reviews* 90, 905-981, doi:10.1152/physrev.00041.2009 (2010).

What is claimed is:

1. A method of treating a neurodegenerative disorder in a subject comprising administering to the subject a first therapeutic agent and a second therapeutic agent;
   wherein the first therapeutic agent and the second therapeutic agent each binds to one or more targets thereby modulating the activity of at least one target pathway;
   wherein at least one of the one or more targets bound by the first therapeutic agent is different than the one or more targets bound by the second therapeutic agent;

wherein the combination of therapeutic agents has a synergistic protective effect on the neurodegenerative disorder; and wherein the first therapeutic agent and second therapeutic agent modulate one or more of the combination of target pathways selected from the group consisting of Calcium signaling pathway, cGMP-PKG signaling pathway, cAMP signaling pathway, 5-hydroxytryptamine receptor pathway, muscarinic acetylcholine receptor pathway, Rap1 signaling pathway, Serotonergic synapse, Dopaminergic pathway, Cholinergic pathway, alpha adrenergic receptor pathway, PI3K-Akt signaling pathway, Ras signaling pathway, and AMPK signaling pathway.

2. The method of claim 1, wherein the neurodegenerative disorder is selected from the group consisting of Huntington's disease, Alzheimer's disease, Parkinson's disease, Sinocerebellar ataxia, prion disease, age related dementia, Amyotrophic lateral sclerosis, and Batten disease.

3. The method of claim 1, wherein the method further comprises one or more additional therapeutic agents.

4. The method of claim 1, the first therapeutic agent modulates the activity of a target pathway different than the second therapeutic agent.

5. The method of claim 1, wherein the first and second therapeutic agents are administered concurrently or sequentially.

6. The method of claim 1, wherein the first and second therapeutic agents are administered simultaneously as single composition.

7. The method of claim 1, wherein at least two target pathways are modulated by the targets bound by the first and second therapeutic agents.

8. The method of claim 1, wherein the first and second therapeutic agents bind to two or more targets selected from the group consisting of 5-hydroxytryptamine receptor 2A, Glucocorticoid receptor, Alpha-2C adrenergic receptor, D(3) dopamine receptor, D(2) dopamine receptor, 5-hydroxytryptamine receptor 2C, Muscarinic acetylcholine receptor M2, Muscarinic acetylcholine receptor M4, Muscarinic acetylcholine receptor M1, Alpha-2A adrenergic receptor, Alpha-2B adrenergic receptor, 5-hydroxytryptamine receptor 2B, Muscarinic acetylcholine receptor M5, Muscarinic acetylcholine receptor M3, 5-hydroxytryptamine receptor 7, Sodium-dependent dopamine transporter, D(1A) dopamine receptor, Alpha-1D adrenergic receptor, 5-hydroxytryptamine receptor 6, 5-hydroxytryptamine receptor 1A, Sodium-dependent serotonin transporter, 5-hydroxytryptamine receptor 1D, Alpha-1B adrenergic receptor, D(1B) dopamine receptor, Alpha-1A adrenergic receptor, 5-hydroxytryptamine receptor 5A, 5-hydroxytryptamine receptor 3A, 5-hydroxytryptamine receptor 1E, 5-hydroxytryptamine receptor 1F, cGMP-inhibited 3',5'-cyclic phosphodiesterase A, 5-hydroxytryptamine receptor 1B, D(4) dopamine receptor, cAMP and cAMP-inhibited cGMP 3',5'-cyclic phosphodiesterase 10A, and cAMP-specific 3',5'-cyclic phosphodiesterase 4B.

9. The method of claim 1, wherein the first therapeutic agent and second therapeutic agent comprise Betamethasone and Lonidamine; Sodium Nitroprusside and Triamcinolone; Sodium Nitroprusside and Betamethasone; Sodium Nitroprusside and Beclomethasone; Ethoxzolamide and Beclomethasone; Triprolidine hydrochloride and Betamethasone; Domperidone and Isotharine mesylate; Sodium Nitroprusside and Budesonide; Isotharine mesylate and m-lodobenzylguanidine hemisulfate; Sodium Nitroprusside and Isotharine mesylate; Sodium Nitroprusside and Lansoprazole; Ethoxzolamide and Betamethasone; Sodium Nitroprusside and Mianserin hydrochloride; Beclomethasone and Quipazine,N-methyl-,dimaleate; Sodium Nitroprusside and Loxapine succinate; Ethoxzolamide and Loxapine succinate; Ethoxzolamide and Domperidone; Ruthenium red and Betamethasone; 3 tropanyl-indole-3-carboxylate hydrochloride and Isotharine mesylate; Benztropine mesylate and Isotharine mesylate; Isotharine mesylate and Loxapine succinate; Domperidone and m-lodobenzylguanidine hemisulfate; Sodium Nitroprusside and U-83836 dihydrochloride; Tetradecylthioacetic acid and Budesonide; Betamethasone and Quipazine,N-methyl-,dimaleate; Tetradecylthioacetic acid and Betamethasone; Tetradecylthioacetic acid and Isotharine mesylate; Isotharine mesylate and Mianserin hydrochloride; Isotharine mesylate and Papaverine hydrochloride; Betamethasone and Isotharine mesylate; Triamcinolone and Benztropine mesylate; Domperidone and Lansoprazole; Beclomethasone and Isotharine mesylate; Sodium Nitroprusside and Lonidamine; Triprolidine hydrochloride and Beclomethasone; Triamcinolone and Lonidamine; Beclomethasone and 3-tropanyl-indole-3-carboxylate hydrochloride; Betamethasone and 3-tropanyl-indole-3-carboxylate hydrochloride; Beclomethasone and Domperidone; Tetradecylthioacetic acid and Triamcinolone; Sodium Nitroprusside and Triprolidine hydrochloride; Triamcinolone and Domperidone; Ethoxzolamide and Budesonide; Domperidone and Papaverine hydrochloride; Isotharine mesylate and PD168,077 maleate; Ethoxzolamide and Triamcinolone; Sodium Nitroprusside and 3-tropanyl-indole-3-carboxylate hydrochloride; Betamethasone and Benztropine mesylate; Ethoxzolamide and Lonidamine; Triamcinolone and Isotharine mesylate; Domperidone and PD168,077 maleate; Ethoxzolamide and Triprolidine hydrochloride; Loxapine succinate and m-lodobenzylguanidine hemisulfate; Budesonide and Quipazine,N-methyl-,dimaleate; Beclomethasone and Lonidamine; Sodium Nitroprusside and Domperidone; Ethoxzolamide and Benztropine mesylate; Ruthenium red and Domperidone; Ethoxzolamide and Quipazine,N-methyl-,dimaleate; Loxapine succinate and PD168,077 maleate; 3 tropanyl-indole-3-carboxylate hydrochloride and m-lodobenzylguanidine hemisulfate.

10. The method of claim 9, wherein the neurodegenerative disorder is Huntington's disease.

11. A method of screening for a synergistic combination therapy to a neurodegenerative disease comprising, assaying two or more prospective therapeutic agents for the ability to modulate a disease phenotype using a clinically relevant phenotypic assay; populating from a database targets known to bind the prospective therapeutic agents; selecting at least two prospective therapeutic agents, a first therapeutic agent and a second therapeutic agent; wherein at least one target bound by the first therapeutic agent is different than the targets bound by the second therapeutic agent; wherein the first therapeutic agent and second therapeutic agent modulate one or more of the target pathways selected from the group consisting of Calcium signaling pathway, cGMP-PKG signaling pathway, cAMP signaling pathway, 5-hydroxytryptamine receptor pathway, muscarinic acetylcholine receptor pathway, Rap1 signaling pathway, Serotonergic synapse, Dopaminergic pathway, Cholinergic pathway, alpha adrenergic receptor pathway, PI3K-Akt signaling pathway, Ras signaling pathway, and AMPK signaling pathway.

12. The method of claim 11, further comprising pairing prospective therapeutic agents by selecting the optimal modulating pathways/networks based on the activity of the respective therapeutic agents.

13. The method of claim 11, wherein the neurodegenerative disease is selected from the group consisting of Huntington's disease, Creutzfeldt-Jakob disease; Primary progressive aphasia; Frontotemporal lobar degeneration; Progressive supranuclear palsy; Friedreich's Ataxia, Alzheimer's disease, Parkinson's disease, Sinocerebellar ataxia, prion disease, age related dementia, Amyotrophic lateral sclerosis, and Batten disease.

14. The method of claim 13, wherein the neurodegenerative disease is Huntington's disease.

15. The method of claim 11, wherein the clinically relevant assay is a propidium iodide assay comprising contacting serum deprived STHdh$^{111}$ cells with a compound and staining the cells for viability with propidium iodide; wherein in viable cells indicate a protective compound.

* * * * *